US010544468B2

(12) United States Patent
Gilsinger et al.

(10) Patent No.: US 10,544,468 B2
(45) Date of Patent: Jan. 28, 2020

(54) MOLECULAR MARKERS AND PHENOTYPIC SCREENING FOR METRIBUZIN TOLERANCE

(71) Applicant: Monsanto Technology LLC, St. Louis, MO (US)

(72) Inventors: Jesse Gilsinger, St. Louis, MO (US); Brad LaValle, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 873 days.

(21) Appl. No.: 14/422,908

(22) PCT Filed: Aug. 29, 2013

(86) PCT No.: PCT/US2013/057241
§ 371 (c)(1),
(2) Date: Feb. 20, 2015

(87) PCT Pub. No.: WO2014/036231
PCT Pub. Date: Mar. 6, 2014

(65) Prior Publication Data
US 2015/0216135 A1    Aug. 6, 2015

Related U.S. Application Data

(60) Provisional application No. 61/694,990, filed on Aug. 30, 2012.

(51) Int. Cl.
| | |
|---|---|
| *C12Q 1/6827* | (2018.01) |
| *C12Q 1/6895* | (2018.01) |
| *A01N 43/707* | (2006.01) |
| *A01H 1/04* | (2006.01) |

(52) U.S. Cl.
CPC .............. *C12Q 1/6895* (2013.01); *A01H 1/04* (2013.01); *A01N 43/707* (2013.01)

(58) Field of Classification Search
CPC ................................................ C12Q 1/6827
See application file for complete search history.

(56) References Cited

U.S. PATENT DOCUMENTS

| | | |
|---|---|---|
| 8,115,076 B2 | 2/2012 | Narvel et al. |
| 2006/0288444 A1 | 12/2006 | McCarroll et al. |
| 2011/0185444 A1 | 7/2011 | Li et al. |
| 2012/0030820 A1 | 2/2012 | Gilsinger |
| 2012/0047596 A1 | 2/2012 | Narvel et al. |

FOREIGN PATENT DOCUMENTS

| | | |
|---|---|---|
| WO | 2009/085982 A1 | 7/2009 |
| WO | 2012/082548 A2 | 6/2012 |

OTHER PUBLICATIONS

Cregan (Crop Sci. 39:1464-1490 (1999)).*
www.soybase.org accessed on Jun. 12, 2017.*
Kilen 1986 The Journal of Heredity 77: 275-277.*
Cregan et al 1999 Crop Science 39(5): 1464-1490.*
Weng et al 2001 The Jornal of Heredity 92(5): 442-446<br>.*
Xia et al 2007 DNA Research 14: 257-269.*
Hardcastle 1974 Weed Research 14: 181-184.*
Mian et al., "RFLP Analysis of Chlorimuron Ethyl Sensitivity in Soybean", The Journal of Heredity, 1997, pp. 38-41, vol. 88, No. 1.
Grimwood, "Genomic Sequence for Glycine Max" May 31, 2012, Genbank [database online]. Accession: AC235896.2 [retrieved on Feb. 19, 2014] <URL: http://www.ncbi.nlm.nih.gov/nuccore/AC235896.2>.
Zhu et al., "Single-Nucleotide Polymorphisms in Soybean", Genetics Society of America, Mar. 2003, pp. 1123-1134, vol. 163.
Hyten et al., "A High Density Integrated Genetic Linkage Map of Soybean and the Development of a 1536 Universal Soy Linkage Panel for Quantitative Traits Locus Mapping", Crop Science, May-Jun. 2010, pp. 960-968, vol. 50.
Kilen, T.C., "A Favorable Linkage Combination in the Soybean", Journal of Heredity, Jul. 1986, pp. 275-277, vol. 77, Issue 4.
Choi et al., "A Soybean Transcript Map: Gene Distribution, Haplotype and Single-Nucleotide Polymorphism Analysis", Genetics Society of America, May 2007, pp. 685-696, vol. 176.
Wax et al., "Differential Response of Soybean Cultivars to Metribuzin", Agronomy Journal, May-Jun. 1976, pp. 484-486, vol. 68.
Yoon et al., "BARCSoySNP23: A Panel of 23 Selected SNPs for Soybean Cultivar Identification", Theor Appl Genet, Mar. 2007, pp. 885-899, vol. 114.
Hyten et al., "High-throughout SNP Discovery Through Deep Resequencing of a Reduced Representation Library to Anchor and Orient Scaffolds in the Soybean Whole Genome Sequence", BMC Genomics, 2010, pp. 1-8, vol. 11 No. 38.
Kilen et al., "Identification and Inheritance of Metribuzin Tolerance in Wild Soybean", Crop Science, May 1992, pp. 684-685, vol. 32, No. 3.

* cited by examiner

*Primary Examiner* — David H Kruse
(74) *Attorney, Agent, or Firm* — Thompson Coburn LLP; William A. Holtz; Lawrence M. Lavin, Jr.

(57) ABSTRACT

The present invention provides methods and compositions for the identification and selection of loci modulating metribuzin herbicide tolerance in plant breeding. In addition, methods are provided for screening germplasm entries for the performance and expression of the metribuzin tolerance trait.

21 Claims, No Drawings

Specification includes a Sequence Listing.

MOLECULAR MARKERS AND PHENOTYPIC SCREENING FOR METRIBUZIN TOLERANCE

CROSS-REFERENCE TO RELATED APPLICATIONS

This application is a 35 U.S.C. § 371 National Phase of International Patent Application No. PCT/US2013/057241, filed Aug. 29, 2013 and incorporated herein by reference in its entirety, which claims the benefit of U.S. Provisional Application Ser. No. 61/694,990 filed Aug. 30, 2012, which is incorporated herein by reference in its entirety.

INCORPORATION OF SEQUENCE LISTING

A sequence listing containing the file named "46_21_59410.txt" which is 21,685 bytes (measured in MS-Windows®) and created on Aug. 26, 2013, contains 42 nucleotide sequences, is provided herewith via the USPTO's EFS system, and is incorporated herein by reference in its entirety.

INCORPORATION OF TABLE 2

A listing of various soybean linkage group N (chromosome 3) markers is provided herewith in the Specification as Table 2. Table 2 is provided at the end of the specification following the Examples and is incorporated herein in its entirety.

BACKGROUND

Distinct soybean varieties have been shown to exhibit different degrees of tolerance to the herbicide metribuzin (Wax et al. *Agron. Journal.* 68:484-486, 1976). Genetic linkage between soybean loci associated with *Phytophora* resistance and loci associated with metribuzin tolerance have also been reported (Kilen, *Journal of Heredity*, 77(4): 275-277, 1986).

SUMMARY

"Metribuzin sensitivity" is an undesirable phenotype observed in certain soybean varieties. It has been discovered that after application of metribuzin, the leaves of certain soybean plant varieties can exhibit a "metribuzin sensitivity phenotype" ranging from mild leaf chlorosis and/or necrosis to severe leaf chlorosis and/or necrosis upon exposure to metribuzin. In the most extreme cases, application of metribuzin to certain sensitive soybean varieties that exhibit severe leaf chlorosis and/or necrosis can result in plant death. However, other tolerant soybean varieties that are exposed to metribuzin in parallel with the sensitive soybean varieties will exhibit little to no leaf chlorosis and/or necrosis and will complete their life cycle. The metribuzin sensitivity phenotype can be observed within about 7 to about 21 days after herbicide application in certain soybean varieties that are sensitive to metribuzin. The metribuzin sensitivity phenotype is undesirable as it can lead to reduced yield in certain soybean plant varieties exposed to metribuzin.

Provided herein are soybean plants comprising an introgressed genomic region associated with a metribuzin tolerance phenotype. Also provided herein are markers that reside outside of a genomic region associated with a metribuzin tolerance phenotype and that facilitate breeding activities that include, but are not limited to, introgression of this genomic region. Markers and specific alleles thereof that are associated with a metribuzin tolerance phenotype are also provided. Methods of obtaining a soybean plant that exhibits a metribuzin tolerance phenotype and methods of obtaining a soybean plant comprising in its genome at least one metribuzin tolerance locus are also provided. Methods that provide for the introgression of a genomic region associated with a metribuzin tolerance phenotype into soybean germplasm that has a genomic region associated with a metribuzin sensitivity phenotype are also provided. Identification of molecular markers associated with loci that confer the metribuzin tolerance phenotype has significant economic value. By using markers associated with the metribuzin tolerance trait, breeders can select soybean varieties with the favorable alleles (i.e. alleles that are not associated with the metribuzin sensitivity trait) for use in trait integration. They can also use the markers to help them eliminate unfavorable alleles (i.e. alleles that are associated with the metribuzin sensitivity trait) in soybeans. In certain embodiments, commercially desirable soybean lines that carry a genomic region that is associated with a "metribuzin tolerance" phenotype and tolerate dosages of metribuzin sufficient to provide for control of undesirable weeds are thus provided.

Methods for selecting a metribuzin tolerant plant from a population of plants comprising both metribuzin sensitive and metribuzin tolerant plants are provided. In certain embodiments, the plurality of soybean plants comprises a population that is obtained by: i) crossing a parent plant comprising at least one metribuzin tolerance locus with a parent plant comprising at least one metribuzin sensitivity locus; or, ii) obtaining seed or progeny from a parental plant segregating for at least one metribuzin tolerance locus. In certain embodiments, the aforementioned methods can further comprise the step of assaying for the presence of at least one additional marker, where the additional marker is either linked or unlinked to the linkage group N genomic region. In certain embodiments of the aforementioned methods, the plurality of soybean plants, the soybean plant, and/or progeny thereof are exposed to a dosage of metribuzin sufficient to cause metribuzin sensitivity in a sensitive variety. In certain embodiments of the aforementioned methods, a plant that exhibits a metribuzin tolerance phenotype is selected.

Also provided herewith are methods for producing a soybean plant comprising in its genome at least one introgressed metribuzin tolerance locus. Also provided herewith are soybean plants comprising an introgressed metribuzin tolerance locus made by the aforementioned methods. In certain embodiments, a soybean plant comprising an introgressed metribuzin tolerance locus and one or more polymorphic loci comprising alleles or combinations of alleles that are not found in a metribuzin tolerant soybean variety and that are linked to the introgressed metribuzin tolerance locus, where the plant is produced by the aforementioned methods are provided.

Also provided are soybean plants comprising an introgressed metribuzin tolerance locus and one or more polymorphic loci comprising alleles or combinations of alleles that are not found in a metribuzin tolerant soybean variety and that are linked to the introgressed metribuzin tolerance locus.

Methods for obtaining a soybean plant comprising in its genome at least one metribuzin tolerance locus, compromising the steps of: genotyping a plurality of soybean plants with respect to at least one genetic locus in a linkage group N genomic region flanked by loci NGMAX006077640 (SEQ ID NO: 3) and NS0138011 (SEQ ID NO: 9); and selecting a soybean plant comprising in its genome at least one genetic locus comprising a genotype associated with metribuzin tolerance are provided herein. In certain embodiments, the genotype associated with metribuzin tolerance comprises at least one polymorphic allele of at least one marker in a sub-region of the linkage group N region flanked by loci NGMAX006077928 (SEQ ID NO: 4) and NGMAX006080885 (SEQ ID NO: 8). In certain embodiments of the aforementioned methods, the genotype associated with metribuzin tolerance comprises at least one polymorphic allele of at least one marker in the first linkage group N region or the sub-region, wherein the marker comprises a TT allele of NGMAX006079502 (SEQ ID NO:7). In certain embodiments, the plurality of soybean plants comprises a population that is obtained by: i) crossing a parent plant comprising at least one metribuzin tolerance locus with a parent plant comprising at least one metribuzin sensitivity locus; or, ii) obtaining seed or progeny from a parental plant segregating for at least one metribuzin tolerance locus. In certain embodiments, the population contains plants that contain a transgene that confers resistance to dicamba and/or a transgene that confers resistance to glyphosate. In certain embodiments, the methods can further comprise the step of assaying for the presence of at least one additional marker, wherein the additional marker is either linked or unlinked to the linkage group N genomic region. In certain embodiments, the methods can comprise exposing the selected soybean plant or progeny thereof comprising the genetic locus to a dosage of metribuzin sufficient to cause a deleterious effect in a variety that is moderately sensitive or sensitive to metribuzin and isolating a metribuzin tolerant plant therefrom. In certain embodiments, the selection comprises exposing a genotyped soybean plant comprising the genetic locus to a dosage of metribuzin sufficient to cause a deleterious effect in a variety that is moderately sensitive or sensitive to metribuzin and isolating a metribuzin tolerant plant therefrom.

Methods for producing a soybean plant comprising in its genome at least one introgressed metribuzin tolerance locus comprising the steps of: crossing a first soybean plant with a metribuzin tolerance locus with a second soybean plant comprising: a metribuzin sensitivity locus in a first linkage group N genomic region flanked by loci NGMAX006077640 (SEQ ID NO: 3) and NS0138011 (SEQ ID NO: 9) and at least one linked polymorphic locus not present in the first soybean plant to obtain a population segregating for the metribuzin tolerance loci and the linked polymorphic locus; detecting at least two polymorphic nucleic acids in at least one soybean plant from the population, wherein at least one of the polymorphic nucleic acids is located in the linkage group N region and wherein at least one of the polymorphic amino acids is a linked polymorphic locus not present in the first soybean plant; and selecting a soybean plant comprising a genotype associated with metribuzin tolerance and at least one linked marker found in the second soybean plant comprising a metribuzin sensitivity locus but not found in the first soybean plant, thereby obtaining a soybean plant comprising in its genome an introgressed metribuzin tolerance locus are also provided. In certain embodiments, at least one of the first or the second soybean plants comprises a transgene that confers resistance to dicamba and/or a transgene that confers resistance to glyphosate. In certain embodiments of the methods, the population, the selected soybean plant, and/or progeny of the selected soybean plant is exposed to a dosage of metribuzin sufficient to cause a deleterious effect in a metribuzin sensitive variety. In certain embodiments of the methods, the polymorphic nucleic acid detected in step (b) is detected with marker NGMAX006079502 (SEQ ID NO: 7). In certain embodiments of the methods, the polymorphic nucleic acid detected in step (b) comprises a TT allele of NGMAX006079502 (SEQ ID NO: 7). In certain embodiments of any of the aforementioned methods, the linked polymorphic locus is detected with a genotypic marker, a phenotypic marker, or both. In certain embodiments of any of the aforementioned methods, the linked polymorphic locus is detected with a marker that is located within about 1000, 500, 100, 40, 20, 10, or 5 kilobases (Kb) of the metribuzin tolerance locus. In certain embodiments of any of the aforementioned methods, the linked polymorphic locus is detected with at least one marker selected from the group consisting of NGMAX006083631 (SEQ ID NO: 10), NS0202926 (SEQ ID NO: 11), NGMAX006084289 (SEQ ID NO: 12), and NGMAX006088354 (SEQ ID NO: 13).

Also provided herein are soybean plants made any of the aforementioned methods, wherein the soybean plant comprises an introgressed metribuzin tolerance locus.

Also provided herein are soybean plants comprising an introgressed metribuzin tolerance locus, wherein at least one linked marker found in the soybean plant is characteristic of germplasm comprising a metribuzin sensitivity locus and is not associated with germplasm comprising the metribuzin tolerance locus. In certain embodiments, the introgressed metribuzin tolerance locus comprises a TT allele of NGMAX006079502 (SEQ ID NO: 7).

Also provided herein are soybean plants comprising an introgressed metribuzin tolerance locus, wherein at least one linked marker found in the soybean plant is characteristic of parental germplasm comprising a metribuzin sensitivity locus but is not associated with germplasm comprising the metribuzin tolerance locus. In certain embodiments, the introgressed metribuzin tolerance locus comprises a TT allele of NGMAX006079502 (SEQ ID NO: 7). In certain embodiments, the linked marker is selected from the group consisting of NGMAX006083631 (SEQ ID NO: 10), NS0202926 (SEQ ID NO: 11), NGMAX006084289 (SEQ ID NO: 12), and NGMAX006088354 (SEQ ID NO: 13). In certain embodiments, the linked marker comprises at least one of: a TT or a CT allele of NGMAX006083631 (SEQ ID NO: 10), an AC allele of NS0202926 (SEQ ID NO: 11), a GG allele of NGMAX006084289 (SEQ ID NO: 12), or a GG allele of NGMAX006088354 (SEQ ID NO: 13).

Methods of identifying a soybean plant that comprises a genotype associated with metribuzin tolerance, comprising: detecting in a soybean plant an allele in at least one genetic locus associated with metribuzin tolerance, wherein the genetic locus is in a linkage group N genomic region flanked by loci NGMAX006077640 (SEQ ID NO: 3) and NS0138011 (SEQ ID NO: 9), and denoting that the plant comprises a genotype associated with metribuzin tolerance are also provided. In certain embodiments, the methods can further comprise the step of selecting the denoted plant from a population of plants. In certain embodiments, the methods can further comprise the steps of exposing the denoted soybean plant or progeny thereof to a dosage of metribuzin sufficient to cause a deleterious effect in a variety that is moderately sensitive or sensitive to metribuzin and scoring the exposed plants for metribuzin tolerance. In certain embodiments, the selection comprises exposing the denoted soybean plant or progeny thereof comprising the genetic locus to a dosage of metribuzin sufficient to cause a deleterious effect in a variety that is moderately sensitive or sensitive to metribuzin and isolating a metribuzin tolerant plant therefrom. In certain embodiments, the genotype associated with a metribuzin tolerance comprises at least one polymorphic allele of at least one marker in a sub-region of the linkage group N region that is flanked by loci NGMAX006077928 (SEQ ID NO: 4) and NGMAX006080885 (SEQ ID NO: 8). In certain embodiments, the genotype associated with metribuzin tolerance comprises at least one polymorphic allele of at least one marker in the linkage group N region or sub-region that comprises a TT allele of NGMAX006079502 (SEQ ID NO: 7).

Methods of producing a population of soybean plants with a metribuzin tolerance phenotype are also provided. In certain embodiments, these methods of producing a population of soybean plants comprising a genotype associated with a metribuzin tolerance phenotype can comprise: providing a first population of soybean plants, detecting in the soybean plants of the first population an allele in at least one metribuzin tolerance marker locus associated with a metribuzin tolerance phenotype wherein the metribuzin tolerance marker locus is in a linkage group N genomic region flanked by or including: a) NGMAX006077640 (SEQ ID NO: 3) and NS0138011 (SEQ ID NO: 9); or b) NGMAX006077928 (SEQ ID NO: 4) and NGMAX006080885 (SEQ ID NO: 8); selecting one or more soybean plants exhibiting an allele in the at least one metribuzin tolerance locus from the first population of soybean plants; and producing offspring from the one or more selected soybean plants. In certain embodiments, the genotype associated with metribuzin tolerance comprises at least one polymorphic allele of at least one marker in the first linkage group N region or the sub-region, wherein the marker comprises a TT allele of NGMAX006079502 (SEQ ID NO:7). In certain embodiments, the genotype associated with metribuzin tolerance comprises at least one polymorphic allele of at least one marker in the linkage group N region or sub-region that comprises a TT allele of NGMAX006079502 (SEQ ID NO: 7).

Further areas of applicability will become apparent from the description provided herein. It should be understood that the description and specific examples are intended for purposes of illustration only and are not intended to limit the scope of the present disclosure.

DETAILED DESCRIPTION

Definitions

As used herein, an "allele" refers to one of two or more alternative forms of a genomic sequence at a given locus on a chromosome. When all the alleles present at a given locus on a chromosome are the same, that plant is homozygous at that locus. If the alleles present at a given locus on a chromosome differ, that plant is heterozygous at that locus.

As used herein, the term "denoting" when used in reference to a plant genotype refers to any method whereby a plant is indicated to have a certain genotype. Such indications of a certain genotype include, but are not limited to, any method where a plant is physically marked or tagged. Physical markings or tags that can be used include, but not limited to, a barcode, a radio-frequency identification (RFID) tag, a label, or the like. Indications of a certain genotype also include, but are not limited to, any entry into any type of written or electronic database whereby the plant's genotype is provided.

A "locus" is a position on a genomic sequence that is usually found by a point of reference; e.g., a short DNA sequence that is a gene, or part of a gene or intergenic region. A locus may refer to a nucleotide position at a reference point on a chromosome, such as a position from the end of the chromosome.

As used herein, "linkage group N" corresponds to the soybean linkage group N described in Choi, et al., *Genetics*. 2007 May; 176(1): 685-696. Linkage group N, as used herein, also corresponds to soybean chromosome 3 (as described on the World Wide Web at soybase.org/LG2Xsome.php). As used herein, "polymorphism" means the presence of one or more variations of a nucleic acid sequence at one or more loci in a population of at least two members. The variation can comprise but is not limited to one or more nucleotide base substitutions, the insertion of one or more nucleotides, a nucleotide sequence inversion, and/or the deletion of one or more nucleotides.

As used herein, the term "single nucleotide polymorphism," also referred to by the abbreviation "SNP," means a polymorphism at a single site wherein the polymorphism constitutes any or all of a single base pair change, an insertion of one or more base pairs, and/or a deletion of one or more base pairs.

As used herein, "marker" means a detectable characteristic that can be used to discriminate between organisms. Examples of such characteristics include, but are not limited to, genetic markers, biochemical markers, fermentation yield, fermentation efficiency, energy yield, secondary compounds, metabolites, morphological characteristics, and agronomic characteristics.

As used herein, "marker assay" means a method for detecting a polymorphism at a particular locus using a particular method. Marker assays thus include, but are not limited to, measurement of at least one phenotype (such as seed color, flower color, or other visually detectable trait as well as any biochemical trait), restriction fragment length polymorphism (RFLP), single base extension, electrophoresis, sequence alignment, allelic specific oligonucleotide hybridization (ASO), random amplified polymorphic DNA (RAPD), microarray-based polymorphism detection technologies, and the like.

As used herein, "genotype" means the genetic component of the phenotype and it can be indirectly characterized using markers or directly characterized by nucleic acid sequencing.

As used herein, the term "introgressed", when used in reference to a genetic locus, refers to a genetic locus that has been introduced into a new genetic background. Introgression of a genetic locus can thus be achieved through both plant breeding methods or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion. In certain embodiments, introgression could thus be achieved by substitution of a metribuzin sensitivity locus with a corresponding metribuzin tolerance locus or by conversion of a locus from a metribuzin sensitivity genotype to a metribuzin tolerance genotype.

As used herein, "phenotype" means the detectable characteristics of a cell or organism which can be influenced by gene expression.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into a genotypes differing from ¼ are attributed to linkage.

As used herein, the termed "linked", when used in the context of markers and/or genomic regions, means that the markers and/or genomic regions are located on the same linkage group or chromosome.

As used herein, a "nucleic acid molecule," be it a naturally occurring molecule or otherwise may be "substantially purified", if desired, referring to a molecule separated from substantially all other molecules normally associated with it in its native state. More preferably, a substantially purified molecule is the predominant species present in a preparation. A substantially purified molecule may be at least about 60% free, preferably at least about 75% free, more preferably at least about 90% free, and most preferably at least about 95% free from the other molecules (exclusive of solvent) present in the natural mixture. The term "substantially purified" is not intended to encompass molecules present in their native state.

As used herein, "quantitative trait locus (QTL)" means a locus that controls to some degree numerically representable traits that are usually continuously distributed. As used herein, the term "transgene" means nucleic acid molecules in the form of DNA, such as cDNA or genomic DNA, and RNA, such as mRNA or microRNA, which may be single or double stranded.

As used herein, the term "event", when used in the context of describing a transgenic plant, refers to a particular transformed plant line. In a typical transgenic breeding program, a transformation construct responsible for a trait is introduced into the genome via a transformation method. Numerous independent transformants (events) are usually generated for each construct. These events are evaluated to select those with superior performance.

As used herein, the term "soybean" means *Glycine max* and includes all plant varieties that can be bred with soybean, including wild soybean species. In certain embodiments, soybean plants from the species *Glycine max* and the subspecies *Glycine max* L. ssp. max or *Glycine max* ssp. *formosana* can be genotyped using the compositions and methods of the present invention. In an additional aspect, the soybean plant is from the species *Glycine soja*, otherwise known as wild soybean, can be genotyped using these compositions and methods. Alternatively, soybean germplasm derived from any of *Glycine max, Glycine max* L. ssp. max, *Glycine max* ssp. *Formosana*, and/or *Glycine soja* can be genotyped using compositions and methods provided herein.

As used herein, the term "bulk" refers to a method of managing a segregating population during inbreeding that involves growing the population in a bulk plot, harvesting the self-pollinated seed of plants in bulk, and using a sample of the bulk to plant the next generation.

As used herein, the phrase "metribuzin sensitivity" refers to undesirable phenotypic traits observed in certain soybean germplasms after exposure to metribuzin at a rate of about 0.25 pounds per acre of metribuzin acid to about 0.75 pounds per acre of metribuzin. Such undesirable phenotypic traits include, but are not limited to, leaf chlorosis, leaf necrosis, and plant death.

As used herein, the phrase "metribuzin tolerant" refers to either the absence or reduction of undesirable phenotypic traits observed after exposure to metribuzin in "metribuzin sensitive" soybean germplasms.

As used herein, the term "comprising" means "including but not limited to."

Description

In accordance with the present invention, Applicants have discovered genomic regions, associated markers, and associated methods for identifying and associating genotypes that effect the levels of metribuzin tolerance observed in soybean plants. Metribuzin (4-Amino-6-(1,1-dimethylethyl)-3-(methylthio)-1,2,4-triazin-5(4H)-one) is a useful broad spectrum herbicide for controlling weeds. For example, in one embodiment, a method of the invention comprises screening a plurality of germplasm entries displaying a heritable variation for at least one metribuzin tolerance trait wherein the heritable variation is linked to at least one genotype; and associating at least one genotype from the germplasm entries to at least one metribuzin tolerance trait. In another embodiment, a method of the invention comprises crossing at least two germplasm entries with a test germplasm entry for the evaluation of performance of at least one metribuzin tolerance trait in order to determine preferred crossing schemes. The methods of the present invention can be used with traditional breeding techniques as described below to more efficiently screen and identify genotypes affecting a metribuzin tolerance trait.

The use of markers to infer a phenotype of interest results in the economization of a breeding program by substituting costly, time-intensive phenotyping assays with genotyping assays. Further, breeding programs can be designed to explicitly drive the frequency of specific, favorable phenotypes by targeting particular genotypes (U.S. Pat. No. 6,399,855). Fidelity of these associations may be monitored continuously to ensure maintained predictive ability and, thus, informed breeding decisions (US Patent Application 2005/0015827). In this case, costly, time-intensive phenotyping assays required for determining if a plant or plants contains a genomic region associated with a "metribuzin tolerance" or "metribuzin sensitivity" phenotype can be supplanted by genotypic assays that provide for identification of a plant or plants that contain the desired genomic region that confers metribuzin tolerance.

A Genomic Region Associated with a Metribuzin Tolerance Phenotype

Provided herewith is a soybean genomic region that is shown herein to be associated with a desirable metribuzin tolerance phenotype when present in certain allelic forms.

A soybean genomic region provided that can be associated with a desirable metribuzin tolerance phenotype when present in certain allelic forms is located on the telomere proximal end of the short arm of soybean linkage group N (chromosome 3). A series of markers useful in practicing the methods of this invention are provided herewith in Table 1. Additional markers useful in the practice of the invention are provided herewith in Table 2 of the Specification, which is incorporated herewith by reference in its entirety. Table 2 provides the Table 1 markers, additional nucleic acid markers or loci that have been disclosed in various databases, the relative positions of the markers on a physical map of linkage group N (soybean chromosome 3), and sources for the markers.

TABLE 1

Markers spanning a genomic region associated with a desirable metribuzin tolerance phenotype

| Marker or Locus Name | SEQ ID NO: | Map Position[1] | Allelic form(s) Associated with Metribuzin Tolerance[2] |
|---|---|---|---|
| NS0206337 | 1 | 2,994,090 | |
| NGMAX006077074 | 2 | 3,087,800 | |
| NGMAX006077640 | 3 | 3,209,380 | |
| NGMAX006077928 | 4 | 3239140 | |
| NGMAX006078838 | 5 | 3,336,045 | |
| NGMAX006079484 | 6 | 3,389,797 | |
| NGMAX006079502 | 7 | 3,391,112 | TT[3] |
| NGMAX006080885 | 8 | 3,562,064 | |
| NS0138011 | 9 | 3,801,236 | |
| NGMAX006083631 | 10 | 3,901,416 | |
| NS0202926 | 11 | 3,964,709 | |
| NGMAX006084289 | 12 | 3,979,613 | |
| NGMAX006088354 | 13 | 4,817,793 | |

[1]The relative positions of the approximate middle position of the listed markers or loci based on nucleotide positions on a physical map of soybean linkage group N (chromosome 3) of Table 2 are provided where nucleotide position 2,987,781 is telomere proximal and nucleotide position 4,075,437 is centromere proximal. Polymorphic nucleotide bases are designated in the sequence listing provided herewith according to the WIPO Standard ST.25 (1998), Table 1, as follows: r = g or a (purine); y = t/u or c (pyrimidine); m = a or c; (amino); k = g or t/u (keto); s = g or c (strong interactions 3 H-bonds); w = a or t/u (weak interactions 2H-bonds); b = g or c or t/u (not a); d = a or g or t/u (not c); h = a or c or t/u (not g); v = a or g or c (not t, not u); and n = a or g or c or t/u (unknown, or other; any.)
[2]Both the maternal and paternal alleles of the single nucleotide polymorphisms that can be associated with a metribuzin tolerance phenotype are shown.
[3]The identified polymorphic allele of marker is located at nucleotide 201 of SEQ ID NO: 7.

Also provided herein are sub-regions of the linkage group N region that is flanked by loci NGMAX006077640 (SEQ ID NO: 3) and NS0138011 (SEQ ID NO: 9) that are associated with a metribuzin tolerance phenotype. These loci flank a region that spans telomere proximal nucleotide 3,209,230 to centromere proximal nucleotide 3,801,607 in the physical map of linkage group N provided in Table 2 of the specification. A first sub-region of the linkage group N region associated with a metribuzin tolerance phenotype is flanked by loci NGMAX006077928 (SEQ ID NO: 4) and NGMAX006080885 (SEQ ID NO: 8). These loci flank a sub-region that spans telomere proximal nucleotide 3,238, 990 to centromere proximal nucleotide 3,562,215 in the physical map of linkage group N provided in Table 2 of the specification. Polymorphisms located in this first sub-region that are associated with a metribuzin tolerance phenotype can be detected with markers that include, but are not limited to, NGMAX006079502 (SEQ ID NO: 7). In certain embodiments, a polymorphism in the region or the sub-region is detected with marker NGMAX006079502 (SEQ ID NO: 7). In certain embodiments, the alleles of this marker associated with metribuzin tolerance are a TT allele of NGMAX006079502 (SEQ ID NO: 7).

Additional genetic markers can be used either in conjunction with the markers provided in Table 1 and/or Table 2 or independently of the markers provided in Table 1 and/or Table 2 to practice the methods of the instant invention. Publicly available marker databases from which useful markers can be obtained include, but are not limited to, the soybase.org website on the internet (World Wide Web) that is administered by the United States Agricultural Research Service, the United States Department of Agriculture, and Iowa State University. Additional soybean markers that can be used and that have been described in the literature include, but are not limited to, Hyten et al., *BMC Genomics*. 11:38, 2010; Choi et al., *Genetics*. 176(1):685-96, 2007; Yoon et al., *Theor Appl Genet*. 2007 March; 114(5):885-99; and Hyten et al. *Crop Sci*. 2010 50: 960-968. Given the provision herein of a genomic region on linkage group N (chromosome 3) delimited or flanked by the telomere proximal locus NGMAX006077640 (SEQ ID NO: 3) of Table 2 and the centromere proximal locus and NS0138011 (SEQ ID NO: 9) of Table 2 as well as an assortment of soybean germplasms exhibiting either a "metribuzin sensitivity" or "metribuzin tolerant" phenotype, additional markers located either within or near this genomic region that are associated with these phenotypes can be obtained by merely typing the new markers in the various germplasms provided herewith. The genomic region on linkage group N (chromosome 3) delimited or flanked by the telomere proximal locus NGMAX006077640 (SEQ ID NO: 3) of Table 2 and the centromere proximal locus NS0138011 (SEQ ID NO: 9) of Table 2 can also be mapped relative to markers provided in any publicly available or other soybean physical or genetic map to place this genetic locus on that map. In this regard, publicly available markers SAT_86, SATT152, SATT641, SATT009, and SATT149 can be used to place the linkage group N (chromosome 3) delimited or flanked by the telomere proximal locus NGMAX006077640 (SEQ ID NO: 3) of Table 2 and the centromere proximal locus NS0138011 (SEQ ID NO: 9) on publically available soybean genetic maps.

Identification of Plants Exhibiting the "Metribuzin Sensitivity" or "Metribuzin Tolerance" Phenotype To observe the presence or absence of the "metribuzin sensitivity" or metribuzin tolerance phenotypes, soybean plants are typically exposed in early to mid-vegetative growth stages to one or more doses of metribuzin. Typical doses of metribuzin that can elicit a metribuzin sensitivity phenotype can range from about a 1-fold label application rate of a commercially available metribuzin formulation (i.e. about 0.25 pounds per acre) to about a 3-fold label application rate (i.e. about 0.75 pounds per acre) of a commercially available metribuzin formulation. Commercially available formulations containing metribuzin that can be used include, but are not limited to, Authority®MTZ (FMC Corporation, Philadelphia, Pa., USA); Boundary® (Syngenta, Wilmington, Del., USA); Canopy® or Lexone® (Dupont, Wilmington, Del., USA); Sencor® (Bayer Crop Science, Research Triangle Park, N.C., USA); or TriCor® DF (United Phosphorus, Inc., King of Prussia, Pa., USA. In certain embodiments, the commercially available metribuzin formulation used is TriCor® 75DF. In certain embodiments, doses of metribuzin that can elicit a metribuzin sensitivity phenotype can range from about a 1 fold application rate of about 0.25 pounds per acre to about a three fold application rate of 0.75 pounds per acre.

The metribuzin sensitivity phenotype can be observed approximately one week to three weeks after herbicide application in certain soybean varieties that are sensitive to metribuzin. Metribuzin is typically applied during pre and post-emergent vegetative growth stages. In certain embodiments of these methods, metribuzin can be applied to the soil about 2 days prior to soybean seed planting and activated by irrigation of the planted seed to score for the presence of the metribuzin sensitivity phenotype. Genotypes provided herein are especially useful for providing metribuzin tolerance to plants exposed to metribuzin by a pre-emergence soil drench. As discussed herein, the vegetative stages of soybean are as follows: VE (emergence), VC (cotyledon stage), V1 (first trifoliate leaf), V2 (second trifoliate leaf), V3 (third trifoliate leaf), V(n) (nth trifoliate leaf), and V6 (flowering will soon start). As discussed herein, the reproductive stages of soybean are as follows: R1 (beginning bloom), R2 (full bloom), R3 (beginning pod), R4 (full pod), R5 (beginning seed), R6 (full seed), R7 (beginning maturity) and R8 (full maturity). A description of the soybean vegetative and reproductive stages can be found on the World Wide Web (internet) at ag.ndsu.edu/pubs/plantsci/rowcrops/a1174/a1174w.htm (North Dakota State University publication A-1174, June 1999, Reviewed and Reprinted August 2004).

A rating scale that evaluates the degree of metribuzin sensitivity can also be employed to identify "metribuzin sensitive" and "metribuzin tolerant" plants. An exemplary and non-limiting scale for evaluating the Metribuzin sensitivity phenotype is as follows, where a low number corresponds to a "metribuzin tolerance" phenotype and the a high number correlates to a "metribuzin sensitivity" phenotype:
A rating of 1: Little to no leaf chlorosis/necrosis
A rating of 3: Mild leaf chlorosis/necrosis; plants survive and make full recovery
A rating of 4: Moderate leaf chlorosis/necrosis; plants survive and make full recovery
A rating of 6: Moderate leaf chlorosis/necrosis; plants survive and typically recover
A rating of 7: Severe leaf chlorosis/necrosis; plants survive and typically recover;
A rating of 9: Severe chlorosis/necrosis; plants survive leading to plant death Introgression of a Genomic Region Associated with a Metribuzin Tolerance Phenotype Also provided herewith is unique soybean germplasm comprising an introgressed genomic region that is associated with a metribuzin tolerance phenotype and methods of obtaining the same. Marker-assisted introgression involves the transfer of a chromosomal region, defined by one or more markers, from one germplasm to a second germplasm. Offspring of a cross that contain the introgressed genomic region can be identified by the combination of markers characteristic of the desired introgressed genomic region from a first germplasm (i.e. such as a metribuzin tolerance germplasm) and both linked and unlinked markers characteristic of the desired genetic background of a second germplasm (i.e. a metribuzin sensitivity germplasm). In addition to the markers provided herewith that identify alleles of genomic region that is associated with a metribuzin tolerance phenotype, flanking markers that fall on both the telomere proximal end of the genomic region on linkage group N (chromosome 3) and the centromere proximal end of the linkage group N (chromosome 3) genomic region are also provided in Tables 1 and 2. Table 2 is provided at the end of the specification immediately before the claims. Such flanking markers are useful in a variety of breeding efforts that include, but are not limited to, introgression of the genomic region associated with a metribuzin tolerance phenotype into a genetic background comprising markers associated with germplasm that ordinarily contains the allelic forms of the genomic region that is associated with a "Metribuzin sensitivity" phenotype. Telomere proximal flanking markers that can be used in these methods include, but are not limited to, NS0206337 (SEQ ID NO: 1), NS0262835 (SEQ ID NO: 21), NGMAX006076547 (SEQ ID NO: 18), NGMAX006076962 (SEQ ID NO: 22), NGMAX006077074 (SEQ ID NO: 2), NGMAX006077513 (SEQ ID NO: 23), SAT_186, and NGMAX006077555 (SEQ ID NO: 24), and/or polymorphisms in any of the loci listed in Table 2 of the Specification located between starting base 2,994,256 (the telomere proximal base) of locus NS0206337 (SEQ ID NO: 1) and starting base 3389647 of centromere proximal locus NGMAX006079484 (SEQ ID NO: 6). Centromere proximal flanking markers that can be used in these methods include, but are not limited to, NGMAX006082782 (SEQ ID NO: 25), NGMAX006083256 (SEQ ID NO: 26), NGMAX006083447 (SEQ ID NO: 27), NGMAX006083554 (SEQ ID NO: 28), NGMAX006083631 (SEQ ID NO: 10), NS0202926 (SEQ ID NO: 11), NGMAX006084289 (SEQ ID NO: 12), and NGMAX006088354 (SEQ ID NO: 13) and/or polymorphisms in any of the other loci listed in Table 2 that are centromere proximal to NS0138011 (SEQ ID NO: 9). Soybean plants wherein the sub regions that is flanked by loci NGMAX006077928 (SEQ ID NO: 4) and NGMAX006080885 (SEQ ID NO: 8) is introgressed can be obtained by using the NGMAX006077878 (SEQ ID NO: 19), NGMAX006078122 (SEQ ID NO: 29), NGMAX006078495 (SEQ ID NO: 30), NS0262836 (SEQ ID NO: 31), NGMAX006078838 (SEQ ID NO: 5), NGMAX006079484 (SEQ ID NO: 6), SATT152, SATT641, NGMAX006081942 (SEQ ID NO: 32), NGMAX006081999 (SEQ ID NO: 33), NGMAX006082115 (SEQ ID NO: 34), NGMAX006082688 (SEQ ID NO: 35), NGMAX006082778 (SEQ ID NO: 36), NS0118425 (SEQ ID NO: 37), NGMAX006080509 (SEQ ID NO: 38), or NGMAX006079911 (SEQ ID NO: 20) markers, or by using any of the markers located between this subregions and the telomere and/or centromere proximal portions of the genome that are provided in Table 2. Any of the aforementioned polymorphisms can be identified by sequencing loci from metribuzin sensitivity and metribuzin tolerance germplasms. Additional markers located on linkage group N (chromosome 3) and other chromosomes are disclosed in US Patent Application Publication 2009/0208964. Publicly available marker databases from which additional useful markers located on linkage group N (chromosome 3) and other chromosomes can be obtained include, but are not limited to, the soybase.org website on the internet that is administered by the United States Agricultural Research Service, the United States Department of Agriculture, and Iowa State University. Soybean plants or germplasm comprising an introgressed genomic region that is associated with a metribuzin tolerance phenotype wherein at least 10%, 25%, 50%, 75%, 90%, or 99% of the remain genomic sequences carry markers characteristic of soybean plants or germplasm that are otherwise or ordinarily comprise a genomic region associated with the Metribuzin sensitivity phenotype are thus provided.

In certain embodiments, metribuzin tolerant soybean plant are provided that comprise an introgressed linkage group N region comprising a metribuzin tolerance locus where adjacent or linked genomic regions comprise markers that are not typically linked or associated with the metribuzin tolerance locus in metribuzin tolerant strains. Non-limiting examples of alleles of linked markers that can be used to detect such introgressed metribuzin tolerance regions can include, but are not limited to, a "TT" or a "CT" allele of NGMAX006083631 (SEQ ID NO: 10), an "AC" allele of NS0202926 (SEQ ID NO: 11), a "GG" allele of NGMAX006084289 (SEQ ID NO: 12), and/or a "GG" allele of NGMAX006088354 (SEQ ID NO: 13).

Soybean Plants Comprising Genomic Region Associated with the Metribuzin Sensitivity and Metribuzin Tolerance Phenotypes A non-limiting and exemplary list of soybean plants that comprise genomic regions associated with either a metribuzin sensitivity or a metribuzin tolerance phenotype are provided herewith in Table 3.

TABLE 3

Soybean varieties comprising a genomic region associated with a metribuzin tolerance or metribuzin sensitivity phenotype.

| Branded Name[1] | Metribuzin Phenotype | U.S. Pat. No. | Variety Name in Patent | ATCC Depository Accession Number[2] | Date of Patent Issue |
|---|---|---|---|---|---|
| TRACY | Sensitive | | | | |
| BURLISON (from TRACY) | Sensitive | | | | |
| H7550 | Sensitive | | | | |
| AG6730 | Sensitive | 8,203,040 | A1016332 | PTA-12644 | 19-Jun-12 |
| AG6130 | Sensitive | 8,207,410 | A1016317 | PTA-12643 | 26-Jun-12 |
| PAGODA | Sensitive | | | | |
| DASSEL (from PAGODA) | Sensitive | | | | |
| AG6931 | Tolerant | 2012/0030820 | A1024631 | | |
| AG4730 | Tolerant | 8,115,076 | A1016279 | PTA-12275 | 14-Feb-12 |
| AG4531 | Tolerant | 2012/0047596 | A1024751 | | |
| Tracy-M | Tolerant | | | | |

[1]Branded names of Asgrow ® (designated "AG") and DEKALB ® soybean varieties from Monsanto Co. 800 N. Lindbergh Blvd., St. Louis, MO, USA.
[2]Deposit numbers of seed available through the American Type Culture Collection (ATCC), 10801 University Blvd., Manassas, Va., USA, 20110-2209.
[3]Metribuzin phenotype is the phenotype observed in the indicated germplasm containing a metribuzin sensitivity or metribuzin tolerance locus when exposed to metribuzin.

Also provided herewith are additional soybean plants that comprising a genomic region associated with a metribuzin sensitivity or metribuzin tolerance phenotype that are identified by use of the markers provided in Table 1 and/or Table 2 and/or methods provided herein. Any of the soybean plants identified in Table 3 or other soybean plants that are otherwise identified using the markers or methods provided herein can be used in methods that include, but are not limited to, methods of obtaining soybean plants with an introgressed metribuzin tolerance locus, obtaining a soybean plant that exhibits a metribuzin tolerance phenotype, or obtaining a soybean plant comprising in its genome a genetic region associated with a metribuzin tolerance phenotype.

In certain embodiments, the soybean plants provided herein or used in the methods provided herein can comprise a transgene that confers resistance to dicamba. In certain embodiments, the dicamba tolerant soybean plants can comprise a transgene encoding a dicamba-degrading dicamba monoxygenase (DMO) enzyme that catalyzes the conversion of herbicidal dicamba (3,6-dichloro-o-anisic acid) to a non-toxic 3,6-dichlorosalicylic acid. In certain embodiments, the dicamba-degrading dicamba monoxygenase (DMOw) comprise a DMO enzyme disclosed in U.S. Pat. Nos. 7,022,896, 7,105,724, and 7,812,224, each incorporated herein by reference in their entireties. In certain embodiments, the metribuzin tolerant soybean plants can comprise a dicamba monoxygenase variant which exhibits improved catalytic parameters such as increased turnover number and/or a lower km for the substrate, improved catalysis at lower pH values, and/or improved catalysis at higher temperatures relative to an unaltered dicamba monooxygenase. In certain embodiments, the dicamba monoxygenase variant comprises a DMOc variant enzyme disclosed in U.S. Pat. No. 7,884,262, incorporated herein by reference in its entirety. In certain embodiments, a dicamba monooxygenase is operably linked to a chloroplast transit peptide (CTP). Operable linkage of certain CTPs to DMO is disclosed in U.S. Pat. No. 8,084,666, which is incorporated herein by reference in its entirety. In certain embodiments, it is contemplated that the soybean plants used herein can comprise one or more specific genomic insertion(s) of a dicamba tolerant transgene including, but not limited to, as those found in MON87708 soybean (deposited under ATCC accession number PTA-9670 and described in US Patent Application Publication Number 20110067134).

In certain embodiments, the soybean plants provided herein or used in the methods provided herein can comprise a transgene that confers tolerance to glyphosate. Transgenes that can confer tolerance to glyphosate include, but are not limited to, transgenes that encode glyphosate tolerant Class I EPSPS (5-enolpyruvylshikimate-3-phosphate synthases) enzymes or glyphosate tolerant Class II EPSPS (5-enolpyruvylshikimate-3-phosphate synthases) enzymes. Useful glyphosate tolerant EPSPS enzymes provided herein are disclosed in U.S. Pat. Nos. 6,803,501, RE39,247, 6,225,114, 5,188,642, and 4,971,908. In certain embodiments, the glyphosate tolerant soybean plants can comprise a transgene encoding a glyphosate oxidoreductase or other enzyme which degrades glyphosate. Glyphosate oxidoreductase enzymes had been described in U.S. Pat. No. 5,776,760 and U.S. Reissue Pat. RE38,825. In certain embodiments the soybean plant can comprise a transgene encoding a glyphosate N-acetyltransferase gene that confers tolerance to glyphosate. In certain embodiments, the soybean plant can comprise a glyphosate n-acetyltransferase encoding transgene such as those described in U.S. Pat. No. 7,666,644. In still other embodiments, soybean plants comprising combinations of transgenes that confer glyphosate tolerance are provided. Soybean plants comprising both a glyphosate resistant EPSPS and a glyphosate N-acetyltransferase are also provided herewith. In certain embodiments, it is contemplated that the soybean plants used herein can comprise one or more specific genomic insertion(s) of a glyphosate tolerant transgene including, but not limited to, as those found in: i) MON89788 soybean (deposited under ATCC accession number PTA-6708 and described in US Patent Application Publication Number 2010/0099859), ii) GTS 40-3-2 soybean (Padgette et al., Crop Sci. 35: 1451-1461, 1995), iii) event 3560.4.3.5 soybean (seed deposited under ATCC accession number PTA-8287 and described in US Patent Publication 2009/0036308), or any combination of i (MON89788 soybean), ii (GTS 40-3-2 soybean), and iii (event 3560.4.3.5 soybean).

In certain embodiments, metribuzin tolerant soybean provided herein can further comprise transgenes that confer resistance to both dicamba and glyphosate.

In certain embodiments, it is contemplated that genotypic assays that provide for non-destructive identification of the plant or plants can be performed either in seed, the emergence stage, the "VC" stage (i.e. cotyledons unfolded), the V1 stage (appearance of first node and unifoliate leaves), the V2 stage (appearance of the first trifoliate leaf), and thereafter. In certain embodiments, non-destructive genotypic assays are performed in seed using apparati and associated methods as described in U.S. Pat. Nos. 6,959,617; 7,134,351; 7,454,989; 7,502,113; 7,591,101; 7,611,842; and 7,685,768, which are incorporated herein by reference in their entireties. In certain embodiments, non-destructive genotypic assays are performed in seed using apparati and associated methods as described in US Patent Application Publications 2010/0086963, 2009/0215060, and 2009/0025288, which are incorporated herein by reference in their entireties. Published US Patent Applications US 2006/0042527, US 2006/0046244, US 2006/0046264, US 2006/0048247, US 2006/0048248, US 2007/0204366, and US 2007/0207485, which are each incorporated herein by reference in their entirety, also disclose apparatus and systems for the automated sampling of seeds as well as methods of sampling, testing and bulking seeds. Thus, in a certain embodiments, any of the methods provided herein can comprise screening for markers in individual seeds of a population wherein only seed with at least one genotype of interest is advanced.

Molecular Assisted Breeding Techniques

Genetic markers that can be used in the practice of the instant invention include, but are not limited to, are Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (US Patent Applications 2005/0204780, 2005/0216545, 2005/0218305, and 2006/00504538). The resulting "genetic map" is the representation of the relative position of characterized loci (DNA markers or any other locus for which alleles can be identified) along the chromosomes. The measure of distance on this map is relative to the frequency of crossover events between sister chromatids at meiosis.

As a set, polymorphic markers serve as a useful tool for fingerprinting plants to inform the degree of identity of lines or varieties (U.S. Pat. No. 6,207,367). These markers form the basis for determining associations with phenotype and can be used to drive genetic gain. The implementation of marker-assisted selection is dependent on the ability to detect underlying genetic differences between individuals.

Certain genetic markers for use in the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers that include. but are not limited, to single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 *Gen. Res.* 13:513-523), microarray transcription profiles, DNA-derived sequences, and RNA-derived sequences that are genetically linked to or correlated with metribuzin tolerance loci, regions flanking metribuzin tolerance loci, regions linked to metribuzin tolerance loci, and/or regions that are unlinked to metribuzin tolerance loci can be used in certain embodiments of the instant invention.

In one embodiment, nucleic acid-based analyses for determining the presence or absence of the genetic polymorphism (i.e. for genotyping) can be used for the selection of seeds in a breeding population. A wide variety of genetic markers for the analysis of genetic polymorphisms are available and known to those of skill in the art. The analysis may be used to select for genes, portions of genes, QTL, alleles, or genomic regions (genotypes) that comprise or are linked to a genetic marker that is linked to or correlated with metribuzin tolerance loci, regions flanking metribuzin tolerance loci, regions linked to metribuzin tolerance loci, and/or regions that are unlinked to metribuzin tolerance loci can be used in certain embodiments of the instant invention.

Nucleic acid analysis methods provided herein include, but are not limited to, PCR-based detection methods (for example, TaqMan assays), microarray methods, mass spectrometry-based methods and/or nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 *Cold Spring Harbor Symp. Quant. Biol.* 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form.

Methods for typing DNA based on mass spectrometry can also be used. Such methods are disclosed in U.S. Pat. Nos. 6,613,509 and 6,503,710, and references found therein. Polymorphisms in DNA sequences can be detected or typed by a variety of effective methods well known in the art including, but not limited to, those disclosed in U.S. Pat.

Nos. 5,468,613; 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R. F. Service *Science* 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs, particularly in the case of genotypes.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Metribuzin Phenotyping: Field Screening and Greenhouse Screening

Field screening for metribuzin tolerance in soybeans was performed at the Monsanto Company Soybean Research Station near Mount Olive, N.C. in 2010 and 2011. Metribuzin application rate was 0.5 lbs/acre metribuzin (Sencor®, Bayer Crop Science, Research Triangle Park, N.C., USA) one day prior to planting. Rows were planted as single 6' row plots with 9 seed per foot. Multiple repetitions were grown per row. Within 24 hours after planting, the trial was irrigated with 0.5" of water to help incorporate and activate the herbicide. Injury ratings were taken fourteen to twenty one (14-21) days after planting using a 1-9 scale (for example, 1=no damage, 9=completely killed).

Greenhouse screening for metribuzin tolerance in soybeans was performed using 10 seeds per entry planted in a pot filled with a sandy soil. Pots were then sprayed with 0.25 lbs/acre metribuzin then lightly soaked with water to incorporate herbicide. Metribuzin ratings were then taken seven (7), fourteen (14), and twenty one (21) days after spraying using a 1-9 scale as in the field.

Example 2: Mapping Populations to Screen for Metribuzin Tolerance

A mapping population from a cross between a metribuzin sensitive and a metribuzin tolerant plant (AG6730× AG4531) generated 232 F2:3 rows. Tissue was sampled and genotyped with 127 SNP markers. Then, F2:4 seed from all 232 plant rows were phenotyped in the greenhouse using the method described in Example 1. A major locus was mapped using R/qtl software (located on the world wide web at rqtl.org).

Example 3: Marker-Trait Association for Metribuzin Tolerance

After identifying the target region through the mapping population described in Example 2, a molecular marker was identified. An association study was done using a soybean molecular marker database. Over 200 commercial and breeding lines were characterized for metribuzin tolerance in field and greenhouse screening, as described in Example 1. The marker NGMAX006079502 was found to be tightly linked to the metribuzin tolerance trait and could be useful for marker assisted selection (MAS) to select for metribuzin tolerance and sensitivity in pre-commercial lines. Field studies demonstrate that a line containing the TT allele of NGMAX006079502 (SEQ ID NO:7) has a "metribuzin sensitivity" rating ranging from about 1.0 to about 3.7, indicating tolerance or moderate tolerance to metribuzin 10 days after spray herbicide application, whereas a line containing the CC allele of NGMAX006079502 (SEQ ID NO:7) has a "metribuzin sensitivity" rating ranging from about 7.0 to about 8.0, indicating sensitivity to metribuzin 10 days after spray herbicide application. Lines containing a heterozygous (CT) allele of NGMAX006079502 (SEQ ID NO:7) display a mixed phenotype of both tolerance and sensitivity in the field.

Example 4: Exemplary Marker Assays for Detecting Polymorphisms

In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means. Exemplary primers and probes for amplifying and detecting genomic regions associated with a metribuzin tolerance phenotype are given in Table 4.

TABLE 4

Exemplary Assays for Detecting Polymorphisms

| Marker or Locus Name | Marker SEQ NO ID: | SNP Position | SEQ ID NO Forward Primer | SEQ ID NO Reverse Primer | SEQ ID NO Probe 1 | SEQ ID NO Probe 2 |
| --- | --- | --- | --- | --- | --- | --- |
| NS0138011 | 9 | 385 | 14 | 15 | 16 | 17 |
| NS0118425 | 37 | 303 | 39 | 40 | 41 | 42 |

Example 5: Oligonucleotide Probes Useful for Detecting Polymorphisms by Single Base Extension Methods Oligonucleotides can also be used to detect or type the polymorphisms disclosed herein by single base extension (SBE)-based SNP detection methods. Exemplary oligonucleotides for use in SBE-based SNP detection are provided in Table 5. SBE methods are based on extension of a nucleotide primer that is hybridized to sequences adjacent to a polymorphism to incorporate a detectable nucleotide residue upon extension of the primer. It is also anticipated that the SBE method can use three synthetic oligonucleotides. Two of the oligonucleotides serve as PCR primers and are complementary to the sequence of the locus which flanks a region containing the polymorphism to be assayed. Exemplary PCR primers that can be used to type polymorphisms disclosed in this invention are provided in Table 4 in the columns labeled "Forward Primer SEQ ID" and "Reverse Primer SEQ ID". Following amplification of the region containing the polymorphism, the PCR product is hybridized with an extension primer which anneals to the amplified DNA adjacent to the polymorphism. DNA polymerase and two differentially labeled dideoxynucleoside triphosphates are then provided. If the polymorphism is present on the template, one of the labeled dideoxynucleoside triphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected. Exemplary forward and reverse SBE probes are provided in Table 5.

TABLE 5

Exemplary SBE Probes for Detecting Polymorphisms

| Marker or Locus Name | Marker (SEQ ID NO) | SNP Position | Probe (SBE) | Probe (SEQ ID NO) |
|---|---|---|---|---|
| NS0138011 | 9 | 385 | AGTAGATTTTTCATTCACAG | 16 |
|  |  |  | AGATTTGTCATTCACAG | 17 |
| NS0118425 | 37 | 303 | AGGTACATGGCTTATT | 41 |
|  |  |  | AGGTACAGGGCTTAT | 42 |

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

Table 2 of the Specification.

| Locus/Display Name (1) | SEQ ID NO: | Source (3) | Start Base (4) | End Base (5) | Additional Locus Information (6) |
|---|---|---|---|---|---|
| TA41246_3847 |  | Glycine_max_release_2 | 2987781 | 2990873 | EPSP synthase [*Phaseolus vulgaris* (Kidney bean) (French bean)] |
| TC25280 |  | LJGI.070108 | 2987966 | 2990818 | similar to UniRef100_Q30CZ8 Cluster: 3-phoshoshikimate 1-carboxyvinyltransferase, n = 1, *Fagus sylvatica*|Rep: 3-phoshoshikimate 1-carboxyvinyltransferase - *Fagus sylvatica* (Beechnut), partial (61%) |
| TA4400_34305 |  | Lotus_japonicus_release_1 | 2987966 | 2990821 | Putative 5-enolpyruvylshikimate 3-phosphate synthase [*Fagus sylvatica* (Beechnut)] |
| EE124475 |  | Arachis_hypogaea_release_5 | 2988836 | 2990821 | Cluster: 3-phoshoshikimate 1-carboxyvinyltransferase, n = 1, *Medicago truncatula*|Rep: 3-phoshoshikimate 1-carboxyvinyltransferase - *Medicago truncatula* (Barrel medic) |
| TC351295 |  | GMGI.042210 | 2988873 | 2990872 | similar to UniRef100_Q946U9 3-phoshoshikimate 1-carboxyvinyltransferase - *Dicliptera chinensis*, partial (31%) |
| 364540_3303_3443_primers |  | cajanus_cajan | 2989514 | 2990455 | NA |
| 364540_3303_3443 |  | cajanus_cajan | 2989473 | 2990556 | NA |
| TC396920 |  | GMGI.042210 | 2990455 | 2990911 | similar to UniRef100_Q30CZ8 3-phoshoshikimate 1-carboxyvinyltransferase - *Fagus sylvatica* (Beechnut), partial (12%) |
| BARCSOYSSR_03_0169 |  | Wm82_potential_SSR | 2992305 | 2992342 | NA |
| BG726324 |  | Glycine_max_release_2 | 2993161 | 2993597 | Transketolase 7 [*Craterostigma plantagineum*] |
| Contig5194 |  | cajanus_cajan | 2993322 | 2993456 | NA |
| 420200_3495_3356 |  | cajanus_cajan | 2993449 | 2993647 | NA |
| 321475_2492_2114 |  | cajanus_cajan | 2993543 | 2993598 | NA |
| TA47385_3847 |  | Glycine_max_release_2 | 2993258 | 2993936 | Transketolase = C-terminal-like [*Medicago truncatula* (Barrel medic)] |
| 283539_1537_3517 |  | cajanus_cajan | 2993575 | 2993647 | NA |
| BARC-028645-05979 |  | Wm82xPI468916 | 2993383 | 2993935 | NA |

Table 2 of the Specification.

| Locus/Display Name (1) | SEQ ID NO: | Source (3) | Start Base (4) | End Base (5) | Additional Locus Information (6) |
|---|---|---|---|---|---|
| CA901097 | | Phaseolus_coccineus_release_2 | 2993660 | 2993887 | Transketolase, chloroplast [*Zea mays* (Maize)] |
| 419871__3332__0838 | | cajanus_cajan | 2993675 | 2993950 | NA |
| 076083__1270__3130 | | cajanus_cajan | 2993778 | 2993858 | NA |
| CB543460 | | Phaseolus_vulgaris | 2993758 | 2994188 | UniRef100_Q7SIC9 Transketolase, chloroplastic n = 1 Tax = *Zea mays* RepID = TKTC_MAIZE 8.00E−72 |
| NS0206337 | 1 | | 2994256 | 2993925 | |
| NS0262835 | 21 | | | | |
| TC350652 | | GMGI.042210 | 2993763 | 2994578 | homologue to UniRef100_A7QGQ5 Chromosome chr16 scaffold_94, whole genome shotgun sequence - *Vitis vinifera* (Grape), partial (36%) |
| Contig47295 | | cajanus_cajan | 2994121 | 2994425 | NA |
| TC415391 | | GMGI.042210 | 2993161 | 2995388 | homologue to UniRef100_A7QGQ5 Chromosome chr16 scaffold_94, whole genome shotgun sequence - *Vitis vinifera* (Grape), partial (75%) |
| TA47387__3847 | | Glycine_max_release_2 | 2993421 | 2995388 | Transketolase = C-terminal-like [*Medicago truncatula* (Barrel medic)] |
| 086553__2836__0981 | | cajanus_cajan | 2994220 | 2994625 | NA |
| TA3218__3886 | | Phaseolus_coccineus_release_2 | 2993945 | 2994914 | Putative transketolase [*Oryza sativa (japonica* cultivar-group)] |
| asmbl__1387 | | Vigna_unguiculata | 2993464 | 2995403 | NA |
| TA389__3870 | | Lupinus_albus_release_2 | 2994040 | 2994941 | Hypothetical protein [*Arabidopsis thaliana* (Mouse-ear cress)] |
| TA4041__34305 | | Lotus_japonicus_release_1 | 2993956 | 2995456 | Transketolase [*Polygonum tinctorium*] |
| TC32586 | | LJGI.070108 | 2993956 | 2995456 | homologue to UniRef100_A7QGQ5 Cluster: Chromosome chr16 scaffold_94, whole genome shotgun sequence, n = 1, *Vitis vinifera*|Rep: Chromosome chr16 scaffold_94, whole genome shotgun sequence - *Vitis vinifera* (Grape), partial (52%) |
| EG030594 | | Arachis_hypogaea_release_5 | 2994096 | 2995502 | Cluster: Transketolase, C-terminal-like, n = 1, *Medicago truncatula*|Rep: Transketolase, C-terminal-like - *Medicago truncatula* (Barrel medic) |
| 327358__3627__1811 | | cajanus_cajan | 2994925 | 2995342 | NA |
| Gm_W82_CR03.G17750 | | Gm_W82_CR03 | 2993068 | 2997229 | Average Cons Position = LG06 29.4 cM: Q7SIC9 Transketolase, chloroplast 0; Q43848 Transketolase, chloroplast precursor 0 |

Table 2 of the Specification.

| Locus/Display Name (1) | SEQ ID NO: | Source (3) | Start Base (4) | End Base (5) | Additional Locus Information (6) |
|---|---|---|---|---|---|
| Glyma03g03200 | | Glyma1 | 2993113 | 2997229 | ID: 2.2.1.1 (EC) = Transketolase.; ID: CALVIN-PWY (SoyCyc) = Activity = transketolase; Pathway = Calvin-Benson-Bassham cycle; ID: GO: 0003824 (GO) = catalytic activity; ID: GO: 0008152 (GO) = metabolism; ID: K00615 (KO) = E2.2.1.1, tktA, tktB; transketolase [EC: 2.2.1.1] [COG: COG0021] [GO: 0004802]; ID: KOG0523 (KOG) = Transketolase; ID: P21-PWY (SoyCyc) = Activity = transketolase; Pathway = pentose phosphate pathway partial; ID: PF02780 (PFAM) = Transketolase, C-terminal domain; ID: PTHR11624 (Panther) = DEHYDROGENASE RELATED; ID: PWY-5723 (SoyCyc) = Activity = transketolase; Pathway = Rubisco shunt |
| CB540475 | | Phaseolus_vulgaris | 2994918 | 2995549 | UniRef100_A9P7Z7 Putative uncharacterized protein n = 1 Tax = *Populus trichocarpa* RepID = A9P7Z7_POPTR 7.00E−66 |
| CB540475 | | Phaseolus_vulgaris_release_2 | 2994932 | 2995549 | Transketolase [*Polygonum tinctorium*] |
| TC127321 | | MTGI.071708 | 2994911 | 2995908 | homologue to UniRef100_A7QGQ5 Cluster: Chromosome chr16 scaffold_94, whole genome shotgun sequence, n = 1, *Vitis vinifera*|Rep: Chromosome chr16 scaffold_94, whole genome shotgun sequence - *Vitis vinifera* (Grape), partial (30%) |
| 162536_1790_1692 | | cajanus_cajan | 2995327 | 2995533 | NA |
| Cf14551d | | Chafa1_1clean | 2995413 | 2995523 | NA |
| BE660224 | | GMGI.042210 | 2995327 | 2997132 | similar to UniRef100_Q7SIC9 Transketolase, chloroplast - *Zea mays* (Maize), partial (28%) |
| TA74539_3847 | | Glycine_max_release_2 | 2995336 | 2997165 | Putative transketolase [*Oryza sativa (japonica* cultivar-group)] |
| TC356209 | | GMGI.042210 | 2995467 | 2997215 | homologue to UniRef100_Q7SIC9 Transketolase, chloroplast - *Zea mays* (Maize), partial (25%) |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| Cf18959d | | Chafa1__1clean | 2996710 | 2996972 | NA |
| 017718__3891__1341 | | cajanus__cajan | 3001808 | 3001894 | NA |
| asmbl__1388 | | Vigna__unguiculata | 3001905 | 3002039 | NA |
| TC363195 | | GMGI.042210 | 3001739 | 3003321 | similar to UniRef100__Q2HS72 RecA bacterial DNA recombination protein - *Medicago truncatula* (Barrel medic), partial (73%) |
| TA72645__3847 | | Glycine__max__release__2 | 3001802 | 3003321 | RecA bacterial DNA recombination protein; Rad51 = N-terminal [*Medicago truncatula* (Barrel medic)] |
| TC118321 | | MTGI.071708 | 3001993 | 3003907 | homologue to UniRef100__Q2HS72 Cluster: RecA bacterial DNA recombination protein, n = 1, *Medicago truncatula*|Rep: RecA bacterial DNA recombination protein - *Medicago truncatula* (Barrel medic), complete |
| Glyma03g03210 | | Glyma1 | 3001993 | 3005606 | ID: KOG1434 (KOG) = Meiotic recombination protein Dmc1; ID: PF08423 (PFAM) = Rad51; ID: PTHR22942 (Panther) = RECA/RAD51/RADA DNA STRAND-PAIRING FAMILY MEMBER |
| Gm__W82__CR03.G17760 | | Gm__W82__CR03 | 3001993 | 3005606 | Average Cons Position = LG06 29.5 cM: Q2HS72 RecA bacterial DNA recombination protein 1E−115 |
| TC376154 | | GMGI.042210 | 3002839 | 3005687 | homologue to UniRef100__Q2HS72 RecA bacterial DNA recombination protein - *Medicago truncatula* (Barrel medic), partial (55%) |
| AW203630 | | Glycine__max__release__2 | 3003133 | 3005645 | RecA bacterial DNA recombination protein; Rad51 = N-terminal [*Medicago truncatula* (Barrel medic)] |
| asmbl__1389 | | Vigna__unguiculata | 3003153 | 3005658 | NA |
| TC397626 | | GMGI.042210 | 3003192 | 3005712 | similar to UniRef100__A7PYE0 Chromosome chr15 scaffold__37, whole genome shotgun sequence - *Vitis vinifera* (Grape), partial (41%) |
| GD956184 | | GMGI.042210 | 3008221 | 3008344 | NA |
| AI988137 | | Glycine__max__release__2 | 3008222 | 3008482 | NA |
| TC372542 | | GMGI.042210 | 3008222 | 3008967 | similar to UniRef100__Q2HS71 SAM (And some other nucleotide) binding motif, Methyltransferase small, Tetratricopeptide-like helical - *Medicago truncatula* (Barrel medic), partial (19%) |
| Cf3692d | | Chafa1__1clean | 3008508 | 3009020 | NA |
| Cf18146d | | Chafa1__1clean | 3011112 | 3011259 | NA |

Table 2 of the Specification.

| Locus/Display Name (1) | SEQ ID NO: | Source (3) | Start Base (4) | End Base (5) | Additional Locus Information (6) |
|---|---|---|---|---|---|
| Glyma03g03230 | | Glyma1 | 3008222 | 3014755 | ID: KOG3191 (KOG) = Predicted N6-DNA-methyltransferase; ID: PF08242 (PFAM) = Methyltransferase domain; ID: PTHR18895 (Panther) = METHYLTRANSFERASE |
| Gm_W82_CR03.G17770 | | Gm_W82_CR03 | 3008221 | 3014755 | Average Cons Position = LG06 29.5 cM: Q2HS71 SAM (And some other nucleotide) binding motif; Methyltransferase small; Tetratricopeptide-like helical 1E−120 |
| Glyma03g03240 | | Glyma1 | 3011139 | 3012212 | ID: PTHR10483 (Panther) = PENTATRICOPEPTIDE REPEAT-CONTAINING PROTEIN |
| Gm_W82_CR03.G17780 | | Gm_W82_CR03 | 3011139 | 3012212 | Average Cons Position = LG06 29.5 cM: Q2HS71 SAM (And some other nucleotide) binding motif; Methyltransferase small; Tetratricopeptide-like helical 1E−162 |
| TA4527_3886 | | Phaseolus_coccineus_release_2 | 3008884 | 3014665 | Methyltransferase small domain, putative [*Medicago truncatula* (Barrel medic)] |
| TC354042 | | GMGI.042210 | 3008857 | 3014753 | similar to UniRef100_Q2HS71 SAM (And some other nucleotide) binding motif, Methyltransferase small, Tetratricopeptide-like helical - *Medicago truncatula* (Barrel medic), partial (11%) |
| BARC-056039-14002 | | marker_map4 | 3017669 | 3018289 | NA |
| BARC-056115-14110 | | marker_map4 | 3017705 | 3018289 | NA |
| asmbl_1390 | | Vigna_unguiculata | 3021474 | 3022546 | NA |
| BI970682 | | Glycine_max_release_2 | 3021390 | 3024499 | Glycoprotease family = putative [*Medicago truncatula* (Barrel medic)] |
| CB542218 | | Phaseolus_vulgaris_release_2 | 3021591 | 3024498 | Glycoprotease family = putative [*Medicago truncatula* (Barrel medic)] |
| TA63194_3847 | | Glycine_max_release_2 | 3021411 | 3024685 | Glycoprotease family = putative [*Medicago truncatula* (Barrel medic)] |
| NGMAX006076547 | 18 | | 3023578 | 3023879 | |
| TC405131 | | GMGI.042210 | 3021335 | 3030119 | homologue to UniRef100_Q2HS64 Peptidase M22, glycoprotease - *Medicago truncatula* (Barrel medic), partial (67%) |
| TA63193_3847 | | Glycine_max_release_2 | 3021718 | 3030109 | Glycoprotease family = putative [*Medicago truncatula* (Barrel medic)] |
| TC125199 | | MTGI.071708 | 3021786 | 3032333 | UniRef100_Q2HS64 Cluster: Peptidase M22, glycoprotease, n = 1, *Medicago truncatula*\|Rep: Peptidase M22, glycoprotease - *Medicago truncatula* (Barrel medic), complete |

Table 2 of the Specification.

| Locus/Display Name (1) | SEQ ID NO: | Source (3) | Start Base (4) | End Base (5) | Additional Locus Information (6) |
|---|---|---|---|---|---|
| Glyma03g03250 | | Glyma1 | 3021324 | 3034049 | ID: GO: 0004222 (GO) = metalloendopeptidase activity; ID: GO: 0006508 (GO) = proteolysis and peptidolysis; ID: KOG2707 (KOG) = Predicted metalloprotease with chaperone activity (RNAse H/HSP70 fold); ID: PF00814 (PFAM) = Glycoprotease family; ID: PTHR11735 (Panther) = O-SIALOGLYCOPROTEIN ENDOPEPTIDASE |
| Gm_W82_CR03.G17790 | | Gm_W82_CR03 | 3021323 | 3034105 | Average Cons Position = LG06 29.6 cM: O22145 Putative O-sialoglycoprotein endopeptidase 0 |
| Cf13676d | | Chafa1_1clean | 3024476 | 3031407 | NA |
| TC137301 | | MTGI.071708 | 3029622 | 3033990 | similar to UniRef100_A7PYD9 Cluster: Chromosome chr15 scaffold_37, whole genome shotgun sequence, n = 1, *Vitis vinifera*|Rep: Chromosome chr15 scaffold_37, whole genome shotgun sequence - *Vitis vinifera* (Grape), partial (54%) |
| TA63618_3847 | | Glycine_max_release_2 | 3029959 | 3034049 | Glycoprotease family protein = expressed [*Oryza sativa* (*japonica* cultivar-group)] |
| TC382576 | | GMGI.042210 | 3029959 | 3034049 | similar to UniRef100_A7PYD9 Chromosome chr15 scaffold_37, whole genome shotgun sequence - *Vitis vinifera* (Grape), partial (37%) |
| BG363097 | | Glycine_max_release_2 | 3031745 | 3033870 | Putative O-sialoglycoprotein endopeptidase [*Arabidopsis thaliana* (Mouse-ear cress)] |
| Cf633d | | Chafa1_1clean | 3042871 | 3043868 | NA |
| Contig37404 | | cajanus_cajan | 3043758 | 3044495 | NA |
| AW780582 | | Glycine_max_release_2 | 3043770 | 3045739 | Arginase [*Glycine max* (Soybean)] |
| BM524551 | | Glycine_soja_release_2 | 3043778 | 3047793 | Arginase [*Glycine max* (Soybean)] |
| Glyma03g03270 | | Glyma1 | 3042599 | 3050225 | ID: ARG-PRO-PWY (SoyCyc) = Activity = arginase; Pathway = arginine degradation VI arginase 2 pathway; ID: ARGASEDEG-PWY (SoyCyc) = Activity = arginase; Pathway = arginine degradation I arginase pathway; ID: GO: 0016813 (GO) = hydrolase activity, acting on carbon-nitrogen (but not peptide) bonds, in linear amidines; |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| | | | | | ID: GO: 0046872 (GO) = metal ion binding; ID: KOG2964 (KOG) = Arginase family protein; ID: PF00491 (PFAM) = Arginase family; ID: PTHR11358 (Panther) = ARGINASE/AGMATINASE-RELATED; ID: PWY-31 (SoyCyc) = Activity = arginase; Pathway = canavanine degradation; ID: PWY-4984 (SoyCyc) = Activity = arginase; Pathway = urea cycle |
| TA47821_3847 | | Glycine_max_release_2 | 3042608 | 3050217 | Arginase [*Glycine max* (Soybean)] |
| TC349067 | | GMGI.042210 | 3042608 | 3050222 | homologue to UniRef100_O49046 Arginase - *Glycine max* (Soybean), complete |
| Gm_W82_CR03.G17800 | | Gm_W82_CR03 | 3042608 | 3050226 | Average Cons Position = LG06 29.7 cM: O49046 Arginase 0; Q9ZPF5 Probable arginase 1E−149 |
| AF035671.1 | | GenBank | 3042649 | 3050212 | arginase (pAG1) mRNA |
| TA2587_3848 | | Glycine_soja_release_2 | 3042694 | 3050217 | Arginase [*Glycine max* (Soybean)] |
| AW201630 | | Glycine_max_release_2 | 3044392 | 3050203 | Arginase [*Glycine max* (Soybean)] |
| TA47820_3847 | | Glycine_max_release_2 | 3044443 | 3050217 | Arginase [*Glycine max* (Soybean)] |
| BE555381 | | Glycine_max_release_2 | 3044476 | 3050215 | Arginase [*Glycine max* (Soybean)] |
| AW760224 | | Glycine_max_release_2 | 3045393 | 3050217 | Arginase [*Glycine max* (Soybean)] |
| BARCSOYSSR_03_0170 | | Wm82_potential_SSR | 3049488 | 3049513 | NA |
| 087411_2830_1033 | | cajanus_cajan | 3057794 | 3057947 | NA |
| BARCSOYSSR_03_0171 | | Wm82_potential_SSR | 3060741 | 3060796 | NA |
| CB829372 | | LJGI.070108 | 3064721 | 3066034 | similar to UniRef100_A7PYD6 Cluster: Chromosome chr15 scaffold_37, whole genome shotgun sequence, n = 1, *Vitis vinifera*|Rep: Chromosome chr15 scaffold_37, whole genome shotgun sequence - *Vitis vinifera* (Grape), partial (25%) |
| CB829372 | | Lotus_japonicus_release_1 | 3064721 | 3066048 | Protein At1g02020 [*Arabidopsis thaliana* (Mouse-ear cress)] |
| Cf9076d | | Chafa1_1clean | 3065839 | 3066273 | NA |
| Glyma03g03280 | | Glyma1 | 3064341 | 3068565 | NA |
| Gm_W82_CR03.G18410 | | Gm_W82_CR03 | 3064341 | 3068565 | Average Cons Position = LG06 29.7 cM: O23673 T7I23.2 protein 0 |
| Cf9022d | | Chafa1_1clean | 3067253 | 3068192 | NA |
| TC359066 | | GMGI.042210 | 3067284 | 3068559 | similar to UniRef100_A7PYD6 Chromosome chr15 scaffold_37, whole genome shotgun sequence - *Vitis vinifera* (Grape), partial (12%) |

Table 2 of the Specification.

| Locus/Display Name (1) | SEQ ID NO: | Source (3) | Start Base (4) | End Base (5) | Additional Locus Information (6) |
|---|---|---|---|---|---|
| TC372531 | | GMGI.042210 | 3068073 | 3068531 | homologue to UniRef100_A7PYD6 Chromosome chr15 scaffold_37, whole genome shotgun sequence - *Vitis vinifera* (Grape), partial (6%) |
| TA75426_3847 | | Glycine_max_release_2 | 3068073 | 3068565 | Hypothetical protein OSJNBa0040E17.29 [*Oryza sativa* (*japonica* cultivar-group)] |
| 087411_2830_1033 | | cajanus_cajan | 3068301 | 3068451 | NA |
| TC415540 | | GMGI.042210 | 3070549 | 3071117 | NA |
| TA70620_3847 | | Glycine_max_release_2 | 3070549 | 3071597 | NA |
| NGMAX006076962 | 22 | | 3071027 | 3071328 | |
| BI786980 | | GMGI.042210 | 3071177 | 3071597 | weakly similar to UniRef100_A7PYD5 Chromosome chr15 scaffold_37, whole genome shotgun sequence - *Vitis vinifera* (Grape), partial (22%) |
| Glyma03g03290 | | Glyma1 | 3070549 | 3072650 | ID: PF04483 (PFAM) = Protein of unknown function (DUF565) |
| Gm_W82_CR03.G18420 | | Gm_W82_CR03 | 3070422 | 3073399 | Average Cons Position = LG06 29.8 cM: Q0DLP9 Os03g0852600 protein 1E-34 |
| TC418355 | | GMGI.042210 | 3075339 | 3075497 | NA |
| Contig18691 | | cajanus_cajan | 3075406 | 3075624 | NA |
| TA55073_3847 | | Glycine_max_release_2 | 3075408 | 3076254 | Hypothetical protein P0450A04.130 [*Oryza sativa* (*japonica* cultivar-group)] |
| CV543227 | | Phaseolus_vulgaris | 3075585 | 3076188 | UniRef100_A5ASW2 Putative uncharacterized protein (Chromosome chr14 scaffold_54, whole genome shotgun sequence) n = 1 Tax = *Vitis vinifera* RepID = A5ASW2_VITVI 3.00E−53 |
| 238610_1965_0511 | | cajanus_cajan | 3076032 | 3076243 | NA |
| asmbl_1391 | | Vigna_unguiculata | 3075856 | 3076521 | NA |
| Cf9860d | | Chafa1_1clean | 3075867 | 3077453 | NA |
| TA4520_3886 | | Phaseolus_coccineus_release_2 | 3076094 | 3077495 | T12H1.6 protein [*Arabidopsis thaliana* (Mouse-ear cress)] |
| Glyma03g03300 | | Glyma1 | 3075339 | 3078303 | ID: GO: 0008152 (GO) = metabolism; ID: GO: 0008168 (GO) = methyltransferase activity; ID: PF08241 (PFAM) = Methyltransferase domain |
| Gm_W82_CR03.G18430 | | Gm_W82_CR03 | 3075339 | 3078304 | Average Cons Position = LG06 29.8 cM: Q9MAA9 T12H1.6 protein 1E-122 |
| TA55075_3847 | | Glycine_max_release_2 | 3076131 | 3077516 | T12H1.6 protein [*Arabidopsis thaliana* (Mouse-ear cress)] |
| TC354860 | | GMGI.042210 | 3075416 | 3078301 | NA |
| CA853858 | | Glycine_max_release_2 | 3076316 | 3077605 | T12H1.6 protein [*Arabidopsis thaliana* (Mouse-ear cress)] |
| 185290_3395_2875 | | cajanus_cajan | 3079604 | 3079688 | NA |
| 444994_2753_3644 | | cajanus_cajan | 3079467 | 3079945 | NA |
| Contig2609_primers | | cajanus_cajan | 3079569 | 3079914 | NA |
| 444994_2753_3644_primers | | cajanus_cajan | 3079569 | 3079932 | NA |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| 291757_0504_1157 | | cajanus_cajan | 3079486 | 3080310 | NA |
| Contig37450 | | cajanus_cajan | 3079464 | 3081239 | NA |
| Contig37450_primers | | cajanus_cajan | 3079563 | 3081184 | NA |
| Contig2609 | | cajanus_cajan | 3079433 | 3081345 | NA |
| Contig15720_primers | | cajanus_cajan | 3079543 | 3081269 | NA |
| Contig15720 | | cajanus_cajan | 3079444 | 3081466 | NA |
| Contig15959 | | cajanus_cajan | 3079586 | 3081351 | NA |
| Contig10545 | | cajanus_cajan | 3079604 | 3081484 | NA |
| 297476_1912_2252_primers | | cajanus_cajan | 3079917 | 3081197 | NA |
| 134435_3488_1714 | | cajanus_cajan | 3079885 | 3081264 | NA |
| 297476_1912_2252 | | cajanus_cajan | 3079885 | 3081282 | NA |
| 354427_2886_2074 | | cajanus_cajan | 3079885 | 3081283 | NA |
| 400685_3217_2464 | | cajanus_cajan | 3079885 | 3081302 | NA |
| 213795_0367_4002_primers | | cajanus_cajan | 3079929 | 3081272 | NA |
| Contig10545_primers | | cajanus_cajan | 3079921 | 3081281 | NA |
| 213795_0367_4002 | | cajanus_cajan | 3079850 | 3081361 | NA |
| TA50789_3847 | | Glycine_max_release_2 | 3079539 | 3081720 | Hypothetical protein At2g45260 [*Arabidopsis thaliana* (Mouse-ear cress)] |
| Contig40445 | | cajanus_cajan | 3079885 | 3081386 | NA |
| asmbl_1393 | | Vigna_unguiculata | 3079530 | 3081795 | NA |
| CA912097 | | Phaseolus_coccineus_release_2 | 3079548 | 3081861 | Hypothetical protein At2g45260 [*Arabidopsis thaliana* (Mouse-ear cress)] |
| TC352567 | | GMGI.042210 | 3079521 | 3081925 | homologue to UniRef100_A7PYD3 Chromosome chr15 scaffold_37, whole genome shotgun sequence - *Vitis vinifera* (Grape), partial (52%) |
| CV537759 | | Phaseolus_vulgaris | 3079566 | 3081984 | UniRef100_A7PYD3 Chromosome chr15 scaffold_37, whole genome shotgun sequence n = 1 Tax = *Vitis vinifera* RepID = A7PYD3_VITVI 1.00E−119 |
| asmbl_1392 | | Vigna_unguiculata | 3079530 | 3082028 | NA |
| FE898754 | | Phaseolus_vulgaris | 3079885 | 3081807 | UniRef100_A7PYD3 Chromosome chr15 scaffold_37, whole genome shotgun sequence n = 1 Tax = *Vitis vinifera* RepID = A7PYD3_VITVI 3.00E−71 |
| 314959_2658_0543 | | cajanus_cajan | 3081064 | 3081283 | NA |
| Glyma03g03310 | | Glyma1 | 3079477 | 3082885 | ID: PF04859 (PFAM) = Plant protein of unknown function (DUF641) |
| TC388566 | | GMGI.042210 | 3079495 | 3082869 | similar to UniRef100_A7PYD3 Chromosome chr15 scaffold_37, whole genome shotgun sequence - *Vitis vinifera* (Grape), complete |

Table 2 of the Specification.

| Locus/Display Name (1) | SEQ ID NO: | Source (3) | Start Base (4) | End Base (5) | Additional Locus Information (6) |
|---|---|---|---|---|---|
| 286143_2148_1171 | | cajanus_cajan | 3081239 | 3081430 | NA |
| 443764_2874_4020 | | cajanus_cajan | 3081315 | 3081484 | NA |
| 358725_3113_3723 | | cajanus_cajan | 3081352 | 3081476 | NA |
| BW631067 | | LJGI.070108 | 3081192 | 3081649 | similar to UniRef100_A7PYD3 Cluster: Chromosome chr15 scaffold_37, whole genome shotgun sequence, n = 1, *Vitis vinifera*\|Rep: Chromosome chr15 scaffold_37, whole genome shotgun sequence - *Vitis vinifera* (Grape), partial (31%) |
| Cf2278d | | Chafa1_1clean | 3081259 | 3081599 | NA |
| 020962_2290_0631 | | cajanus_cajan | 3081485 | 3081697 | NA |
| TC115824 | | MTGI.071708 | 3081192 | 3082028 | similar to UniRef100_A7PYD3 Cluster: Chromosome chr15 scaffold_37, whole genome shotgun sequence, n = 1, *Vitis vinifera*\|Rep: Chromosome chr15 scaffold_37, whole genome shotgun sequence - *Vitis vinifera* (Grape), partial (58%) |
| Cf20941d | | Chafa1_1clean | 3081615 | 3082518 | NA |
| Contig45852 | | cajanus_cajan | 3082034 | 3082358 | NA |
| BI425936 | | Glycine_max_release_2 | 3081947 | 3082470 | Expressed protein [*Oryza sativa* (*japonica* cultivar-group)] |
| BG156189 | | Glycine_soja_release_2 | 3082080 | 3082515 | Expressed protein [*Oryza sativa* (*japonica* cultivar-group)] |
| BE824427 | | Glycine_max_release_2 | 3082147 | 3082623 | Hypothetical protein At2g45260 [*Arabidopsis thaliana* (Mouse-ear cress)] |
| Pvcon6930 | | Phaseolus_vulgaris | 3082096 | 3082715 | UniRef100_A7PYD3 Chromosome chr15 scaffold_37, whole genome shotgun sequence n = 1 Tax = *Vitis vinifera* RepID = A7PYD3_VITVI 3.00E-66 |
| asmbl_1394 | | Vigna_unguiculata | 3082089 | 3082756 | NA |
| 032057_1031_0927 | | cajanus_cajan | 3082397 | 3082465 | NA |
| 113211_0242_1108 | | cajanus_cajan | 3082410 | 3082520 | NA |
| 004558_3078_0990 | | cajanus_cajan | 3082438 | 3082655 | NA |
| Contig21707 | | cajanus_cajan | 3082447 | 3082655 | NA |
| Glyma03g03320 | | Glyma1 | 3085834 | 3086493 | ID: GO: 0004857 (GO) = enzyme inhibitor activity; ID: GO: 0030599 (GO) = pectinesterase activity; ID: PF04043 (PFAM) = Plant invertase/pectin methylesterase inhibitor |
| Gm_W82_CR03.G18450 | | Gm_W82_CR03 | 3085834 | 3086493 | Average Cons Position = LG06 29.8 cM: O81309 F6N15.9 protein 2E-36 |
| NGMAX006077074 | 2 | | 3087650 | 3087951 | |
| TC352616 | | GMGI.042210 | 3091655 | 3092472 | similar to UniRef100_Q89EJ0 C4-dicarboxylate transport protein - *Bradyrhizobium japonicum*, partial (5%) |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| Glyma03g03330 | | Glyma1 | 3091658 | 3092522 | ID: GO: 0004857 (GO) = enzyme inhibitor activity; ID: GO: 0030599 (GO) = pectinesterase activity; ID: PF04043 (PFAM) = Plant invertase/pectin methylesterase inhibitor |
| Gm_W82_CR03.G18460 | | Gm_W82_CR03 | 3091658 | 3092522 | Average Cons Position = LG06 29.8 cM: O81309 F6N15.9 protein 6E−39 |
| BM139947 | | Glycine_max_release_2 | 3092245 | 3092450 | NA |
| BARCSOYSSR_03_0172 | | Wm82_potential_SSR | 3099116 | 3099163 | NA |
| Glyma03g03340 | | Glyma1 | 3100904 | 3102449 | ID: GO: 0016747 (GO) = transferase activity, transferring groups other than amino-acyl groups; ID: PF02458 (PFAM) = Transferase family |
| BARCSOYSSR_03_0173 | | Wm82_potential_SSR | 3103341 | 3103396 | NA |
| Contig9906_primers | | cajanus_cajan | 3104938 | 3105569 | NA |
| TC413526 | | GMGI.042210 | 3104626 | 3106429 | homologue to UniRef100_Q0ZPT8 Methionine aminopeptidase - *Ananas comosus* (Pineapple), partial (31%) |
| TA60719_3847 | | Glycine_max_release_2 | 3104635 | 3106432 | Methionine aminopeptidase 1 [*Ananas comosus* (Pineapple)] |
| TC374413 | | GMGI.042210 | 3104626 | 3106880 | homologue to UniRef100_Q0ZPT8 Methionine aminopeptidase - *Ananas comosus* (Pineapple), partial (33%) |
| Contig9906 | | cajanus_cajan | 3104585 | 3106940 | NA |
| CB539349 | | Phaseolus_vulgaris_release_2 | 3104890 | 3107370 | Methionine aminopeptidase 1 [*Ananas comosus* (Pineapple)] |
| 034894_1456_0080 | | cajanus_cajan | 3106877 | 3107085 | NA |
| Glyma03g03350 | | Glyma1 | 3104902 | 3109883 | ID: GO: 0009987 (GO) = cellular process; ID: KOG2738 (KOG) = Putative methionine aminopeptidase; ID: PF00557 (PFAM) = metallopeptidase family M24; ID: PTHR10804 (Panther) = PROTEASE FAMILY M24 (METHIONYL AMINOPEPTIDASE, AMINOPEPTIDASE P) |
| Cf3363d | | Chafa1_1clean | 3104911 | 3109882 | NA |
| Pvcon6396 | | Phaseolus_vulgaris | 3104890 | 3111389 | UniRef100_A7PYC9 Methionine aminopeptidase n = 1 Tax = *Vitis vinifera* RepID = A7PYC9_VITVI E-0 |
| CA906284 | | Phaseolus_coccineus_release_2 | 3106886 | 3109505 | Methionine aminopeptidase 1A [*Arabidopsis thaliana* (Mouse-ear cress)] |

Table 2 of the Specification.

| Locus/Display Name (1) | SEQ ID NO: | Source (3) | Start Base (4) | End Base (5) | Additional Locus Information (6) |
|---|---|---|---|---|---|
| Gm_W82_CR03.G18480 | | Gm_W82_CR03 | 3104558 | 3111952 | Average Cons Position = LG06 29.9 cM: Q9SLN5 Methionine aminopeptidase 1A 0; A7PYC9 Methionine aminopeptidase 0 |
| 297876_2793_1957 | | cajanus_cajan | 3108527 | 3109322 | NA |
| 316713_3644_1516 | | cajanus_cajan | 3109394 | 3109635 | NA |
| BARCSOYSSR_03_0174 | | Wm82_potential_SSR | 3120776 | 3120805 | NA |
| Glyma03g03360 | | Glyma1 | 3120992 | 3124949 | ID: GO: 0005618 (GO) = cell wall; ID: GO: 0030599 (GO) = pectinesterase activity; ID: GO: 0042545 (GO) = cell wall modification; ID: PF01095 (PFAM) = Pectinesterase; ID: PWY-1081 (SoyCyc) = Activity = pectinesterase; Pathway = homogalacturonan degradation |
| Gm_W82_CR03.G18490 | | Gm_W82_CR03 | 3120992 | 3124987 | Average Cons Position = LG06 30 cM: Q84R10 Putative pectinesterase 1E-149 |
| BARCSOYSSR_03_0175 | | Wm82_potential_SSR | 3125342 | 3125373 | NA |
| BARCSOYSSR_03_0176 | | Wm82_potential_SSR | 3125603 | 3125626 | NA |
| Glyma03g03370 | | Glyma1 | 3128348 | 3128906 | NA |
| Glyma03g03380 | | Glyma1 | 3129953 | 3130354 | ID: PTHR11615: SF7 (Panther) = gb def: putative formate dehydrogenase alpha subunit [*thermococcus litoralis*] |
| Gm_W82_CR03.G18510 | | Gm_W82_CR03 | 3129953 | 3130354 | Average Cons Position = LG06 30 cM: Q8L924 UPF0497 membrane protein At2g35760 3E-20 |
| 418082_2891_0373 | | cajanus_cajan | 3137176 | 3137447 | NA |
| 375319_2742_1938 | | cajanus_cajan | 3137533 | 3137620 | NA |
| Glyma03g03390 | | Glyma1 | 3136859 | 3138892 | ID: 3.1.1.11 (EC) = Pectinesterase.; ID: GO: 0005618 (GO) = cell wall; ID: GO: 0030599 (GO) = pectinesterase activity; ID: GO: 0042545 (GO) = cell wall modification; ID: K01051 (KO) = E3.1.1.11; pectinesterase [EC: 3.1.1.11] [GO: 0030599]; ID: PF01095 (PFAM) = Pectinesterase; ID: PWY-1081 (SoyCyc) = Activity = pectinesterase; Pathway = homogalacturonan degradation |
| Contig23415 | | cajanus_cajan | 3138247 | 3138699 | NA |
| TC388963 | | GMGI.042210 | 3138211 | 3138811 | homologue to UniRef100_A7PYC6 Chromosome chr15 scaffold_37, whole genome shotgun sequence - *Vitis vinifera* (Grape), partial (38%) |
| 418082_2891_0373 | | cajanus_cajan | 3150943 | 3151220 | NA |
| 375319_2742_1938 | | cajanus_cajan | 3151307 | 3151394 | NA |

Table 2 of the Specification.

| Locus/Display Name (1) | SEQ ID NO: | Source (3) | Start Base (4) | End Base (5) | Additional Locus Information (6) |
|---|---|---|---|---|---|
| BARCSOYSSR_03_0177 | | Wm82_potential_SSR | 3151786 | 3151827 | NA |
| Glyma03g03400 | | Glyma1 | 3150626 | 3154197 | ID: 3.1.1.11 (EC) = Pectinesterase.; ID: GO: 0005618 (GO) = cell wall; ID: GO: 0030599 (GO) = pectinesterase activity; ID: GO: 0042545 (GO) = cell wall modification; ID: K01051 (KO) = E3.1.1.11; pectinesterase [EC: 3.1.1.11] [GO: 0030599]; ID: PF01095 (PFAM) = Pectinesterase; ID: PWY-1081 (SoyCyc) = Activity = pectinesterase; Pathway = homogalacturonan degradation |
| Contig23415 | | cajanus_cajan | 3153333 | 3153797 | NA |
| TA72681_3847 | | Glycine_max_release_2 | 3158234 | 3158915 | Pectinesterase-2 precursor [*Citrus sinensis* (Sweet orange)] |
| TC388963 | | GMGI.042210 | 3158315 | 3158915 | homologue to UniRef100_A7PYC6 Chromosome chr15 scaffold_37, whole genome shotgun sequence - *Vitis vinifera* (Grape), partial (38%) |
| Contig23415 | | cajanus_cajan | 3158426 | 3158880 | NA |
| TC135041 | | MTGI.071708 | 3158575 | 3158878 | UniRef100_Q6PQ93 Cluster: Pectin methylesterase 9, n = 1, *Medicago truncatula*\|Rep: Pectin methylesterase 9 - *Medicago truncatula* (Barrel medic), complete |
| Cf16829d | | Chafa1_1clean | 3158264 | 3159610 | NA |
| Glyma03g03410 | | Glyma1 | 3158102 | 3160282 | ID: 3.1.1.11 (EC) = Pectinesterase.; ID: GO: 0005618 (GO) = cell wall; ID: GO: 0030599 (GO) = pectinesterase activity; ID: GO: 0042545 (GO) = cell wall modification; ID: K01051 (KO) = E3.1.1.11; pectinesterase [EC: 3.1.1.11] [GO: 0030599]; ID: PF01095 (PFAM) = Pectinesterase; ID: PWY-1081 (SoyCyc) = Activity = pectinesterase; Pathway = homogalacturonan degradation |
| 375319_2742_1938 | | cajanus_cajan | 3159522 | 3159607 | NA |
| 418082_2891_0373 | | cajanus_cajan | 3159695 | 3159964 | NA |
| BARCSOYSSR_03_0178 | | Wm82_potential_SSR | 3163958 | 3164025 | NA |
| Glyma03g03420 | | Glyma1 | 3166793 | 3167020 | NA |
| Gm_W82_CR03.G18550 | | Gm_W82_CR03 | 3166793 | 3167020 | Average Cons Position = LG06 30.2 cM: Q8L924 UPF0497 membrane protein At2g35760 2E-13 |
| BARCSOYSSR_03_0179 | | Wm82_potential_SSR | 3167750 | 3167781 | NA |
| SATT159 | | | 3169968 | 3170252 | |
| Satt159 | | marker_map4 | 3169968 | 3170252 | NA |
| BARCSOYSSR_03_0180 | | Wm82_potential_SSR | 3170121 | 3170162 | NA |
| 305096_0951_1070 | | cajanus_cajan | 3170506 | 3170717 | NA |

Table 2 of the Specification.

| Locus/Display Name (1) | SEQ ID NO: | Source (3) | Start Base (4) | End Base (5) | Additional Locus Information (6) |
|---|---|---|---|---|---|
| Glyma03g03430 | | Glyma1 | 3170171 | 3171595 | NA |
| Gm_W82_CR03.G18560 | | Gm_W82_CR03 | 3170171 | 3171595 | Average Cons Position = LG06 30.2 cM: Q6PQ93 Pectin methylesterase 9 1E−26; O04887 Pectinesterase-2 precursor 4E−24; Q6PQ97 Pectin methylesterase 5 2E−22; Q43143 Pectinesterase U1 precursor 2E−16; Q9FY03 Putative pectin methylesterase precursor 4E−14 |
| Contig23415 | | cajanus_cajan | 3170968 | 3171431 | NA |
| NGMAX006077513 | 23 | | 3172140 | 3172441 | |
| NGMAX006077555 | 24 | | 3181380 | 3181681 | |
| Glyma03g03440 | | Glyma1 | 3192517 | 3192801 | NA |
| Gm_W82_CR03.G18570 | | Gm_W82_CR03 | 3192517 | 3192801 | Average Cons Position = LG06 30.3 cM: Q9SM60 Phosphoglucomutase, cytoplasmic 4E−25; P93262 Phosphoglucomutase, cytoplasmic 3E−24 |
| BARCSOYSSR_03_0181 | | Wm82_potential_SSR | 3194639 | 3194700 | NA |
| Glyma03g03450 | | Glyma1 | 3193959 | 3198116 | ID: PTHR13856 (Panther) = VHS DOMAIN CONTAINING PROTEIN FAMILY |
| Gm_W82_CR03.G18580 | | Gm_W82_CR03 | 3193959 | 3198116 | Average Cons Position = LG06 30.4 cM: Q2V732 VHS and GAT domain protein 3E−12 |
| TA67921_3847 | | Glycine_max_release_2 | 3197245 | 3197763 | NA |
| TC407739 | | GMGI.042210 | 3197272 | 3197763 | similar to UniRef100_Q2HSP6 General substrate transporter - *Medicago truncatula* (Barrel medic), partial (4%) |
| BARCSOYSSR_03_0182 | | Wm82_potential_SSR | 3199583 | 3199604 | NA |
| BARCSOYSSR_03_0183 | | Wm82_potential_SSR | 3199966 | 3200010 | NA |
| Contig32455 | | cajanus_cajan | 3200657 | 3200918 | NA |
| Contig19141 | | cajanus_cajan | 3200851 | 3201091 | NA |
| Cf10417d | | Chafa1_1clean | 3200836 | 3201120 | NA |
| TC377879 | | GMGI.042210 | 3200720 | 3201287 | similar to UniRef100_A7PYC6 Chromosome chr15 scaffold_37, whole genome shotgun sequence - *Vitis vinifera* (Grape), partial (27%) |
| 418082_2891_0373 | | cajanus_cajan | 3201086 | 3201309 | NA |
| 375319_2742_1938 | | cajanus_cajan | 3201519 | 3201601 | NA |
| BQ576469 | | GMGI.042210 | 3201494 | 3201914 | similar to UniRef100_O04887 Pectinesterase-2 precursor - *Citrus sinensis* (Sweet orange), partial (10%) |
| BQ576469 | | Glycine_max_release_2 | 3201494 | 3202078 | Pectinesterase-2 precursor [*Citrus sinensis* (Sweet orange)] |
| Glyma03g03460 | | Glyma1 | 3200770 | 3204918 | ID: GO: 0005618 (GO) = cell wall; ID: GO: 0030599 (GO) = pectinesterase activity; ID: GO: 0042545 (GO) = cell wall modification; ID: PF01095 (PFAM) = Pectinesterase |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| 214452__2123__1259 | | cajanus_cajan | 3201638 | 3204052 | NA |
| Pvcon9735 | | Phaseolus_vulgaris | 3201498 | 3204566 | UniRef100__A7PYC6 Pectinesterase n = 1 Tax = *Vitis vinifera* RepID = A7PYC6__VITVI 1.00E−120 |
| TA5573_3885 | | Phaseolus_vulgaris_release_2 | 3201498 | 3204566 | Pectinesterase-2 precursor [*Citrus sinensis* (Sweet orange)] |
| TA41878_3847 | | Glycine_max_release_2 | 3201659 | 3204609 | Pectinesterase-2 precursor [*Citrus sinensis* (Sweet orange)] |
| AW706153 | | GMGI.042210 | 3203771 | 3204190 | similar to UniRef100__A7PYC6 Chromosome chr15 scaffold_37, whole genome shotgun sequence - *Vitis vinifera* (Grape), partial (14%) |
| AW706153 | | Glycine_max_release_2 | 3203769 | 3204345 | Pectinesterase-2 precursor [*Citrus sinensis* (Sweet orange)] |
| Contig23415 | | cajanus_cajan | 3204034 | 3204496 | NA |
| asmbl_1395 | | Vigna_unguiculata | 3204001 | 3204659 | NA |
| AI941403 | | Glycine_max_release_2 | 3204411 | 3204540 | Pectinesterase-2 precursor [*Citrus sinensis* (Sweet orange)] |
| TA41886_3847 | | Glycine_max_release_2 | 3204278 | 3204684 | Pectinesterase-2 precursor [*Citrus sinensis* (Sweet orange)] |
| BQ453360 | | Glycine_max_release_2 | 3204384 | 3204908 | Pectinesterase-2 precursor [*Citrus sinensis* (Sweet orange)] |
| NGMAX006077640 | 3 | | 3209230 | 3209531 | |
| 188924__1171__4036 | | cajanus_cajan | 3211646 | 3211879 | NA |
| Glyma03g03470 | | Glyma1 | 3211521 | 3212299 | ID: PF01657 (PFAM) = Domain of unknown function DUF26 |
| Gm_W82_CR03.G18800 | | Gm_W82_CR03 | 3211521 | 3212299 | Average Cons Position = LG06 30.4 cM: Q6NKQ9 Cysteine-rich repeat secretory protein 15 precursor 3E−47 |
| Cf5097d | | Chafa1__1clean | 3225804 | 3226039 | NA |
| Glyma03g03480 | | Glyma1 | 3225520 | 3226992 | ID: PF02519 (PFAM) = Auxin responsive protein |
| TC362898 | | GMGI.042210 | 3225774 | 3226757 | similar to UniRef100__A7PYC4 Chromosome chr15 scaffold_37, whole genome shotgun sequence - *Vitis vinifera* (Grape), partial (51%) |
| BARCSOYSSR_03_0184 | | Wm82_potential_SSR | 3226514 | 3226540 | NA |
| TA61385_3847 | | Glycine_max_release_2 | 3226092 | 3226992 | NA |
| TC399758 | | GMGI.042210 | 3226663 | 3226990 | NA |
| NGMAX006077878 | 19 | | 3232914 | 3233215 | |
| NGMAX006077928 | 4 | | 3238990 | 3239291 | |
| NGMAX006078122 | 29 | | 3253689 | 3253990 | |
| TA13126_34305 | | Lotus_japonicus_release_1 | 3254515 | 3259837 | Golgi SNARE 12 protein [*Arabidopsis thaliana* (Mouse-ear cress)] |
| TC24266 | | LJGI.070108 | 3254515 | 3259837 | homologue to UniRef100__A7PYC3 Cluster: Chromosome chr15 scaffold_37, whole genome shotgun sequence, n = 1, *Vitis vinifera*|Rep: |

Table 2 of the Specification.

| Locus/Display Name (1) | SEQ ID NO: | Source (3) | Start Base (4) | End Base (5) | Additional Locus Information (6) |
|---|---|---|---|---|---|
| TC365000 | | GMGI.042210 | 3254378 | 3260002 | Chromosome chr15 scaffold_37, whole genome shotgun sequence - *Vitis vinifera* (Grape), partial (57%) |
| BM094071 | | Glycine_max_release_2 | 3254443 | 3259972 | similar to UniRef100_A7PYC3 Chromosome chr15 scaffold_37, whole genome shotgun sequence - *Vitis vinifera* (Grape), partial (72%) |
| Cf1646d | | Chafa1_1clean | 3254532 | 3261153 | Golgi SNARE 12 protein [*Arabidopsis thaliana* (Mouse-ear cress)] |
| TC120084 | | MTGI.071708 | 3254540 | 3261190 | NA |
| | | | | | similar to UniRef100_A7PYC3 Cluster: Chromosome chr15 scaffold_37, whole genome shotgun sequence, n = 1, *Vitis vinifera*|Rep: Chromosome chr15 scaffold_37, whole genome shotgun sequence - *Vitis vinifera* (Grape), partial (98%) |
| Pvcon4074 | | Phaseolus_vulgaris | 3254499 | 3261367 | UniRef100_A7PYC3 Chromosome chr15 scaffold_37, whole genome shotgun sequence n = 1 Tax = *Vitis vinifera* RepID = A7PYC3_VITVI 1.00E−112 |
| Glyma03g03490 | | Glyma1 | 3254361 | 3261723 | ID: GO: 0006886 (GO) = intracellular protein transport; ID: GO: 0016020 (GO) = membrane; ID: K08495 (KO)=; ID: KOG3208 (KOG) = SNARE protein GS28; ID: PF05008 (PFAM) = Vesicle transport v-SNARE protein; ID: PTHR21094 (Panther) = FAMILY NOT NAMED |
| Gm_W82_CR03.G19220 | | Gm_W82_CR03 | 3254361 | 3261723 | Average Cons Position = LG06 30.7 cM: O22151 Golgi SNARE 12 protein 1E−101 |
| BP048935 | | Lotus_japonicus_release_1 | 3259926 | 3261261 | Golgi SNARE 12 protein [*Arabidopsis thaliana* (Mouse-ear cress)] |
| DB979241 | | GMGI.042210 | 3260857 | 3261372 | similar to UniRef100_A7PYC3 Chromosome chr15 scaffold_37, whole genome shotgun sequence - *Vitis vinifera* (Grape), partial (29%) |
| CD399194 | | Glycine_max_release_2 | 3260921 | 3261324 | Golgi SNARE 12 protein [*Arabidopsis thaliana* (Mouse-ear cress)] |
| BARCSOYSSR_03_0185 | | Wm82_potential_SSR | 3267129 | 3267172 | NA |
| BARCSOYSSR_03_0186 | | Wm82_potential_SSR | 3269087 | 3269130 | NA |
| BARCSOYSSR_03_0187 | | Wm82_potential_SSR | 3270199 | 3270218 | NA |
| Contig23197 | | cajanus_cajan | 3272203 | 3272416 | NA |
| 415445_2756_2388 | | cajanus_cajan | 3272279 | 3272416 | NA |
| 183101_0466_0966_primers | | cajanus_cajan | 3273791 | 3273999 | NA |
| 183101_0466_0966 | | cajanus_cajan | 3273730 | 3274095 | NA |
| 206423_3853_3891 | | cajanus_cajan | 3273959 | 3274097 | NA |

Table 2 of the Specification.

| Locus/Display Name (1) | SEQ ID NO: | Source (3) | Start Base (4) | End Base (5) | Additional Locus Information (6) |
|---|---|---|---|---|---|
| TC361285 | | GMGI.042210 | 3273414 | 3276514 | similar to UniRef100_Q6SS00 YABBY-like transcription factor GRAMINIFOLIA - Antirrhinum majus (Garden snapdragon), partial (86%) |
| Glyma03g03500 | | Glyma1 | 3273412 | 3276522 | ID: PF04690 (PFAM) = YABBY protein |
| Gm_W82_CR03.G19230 | | Gm_W82_CR03 | 3273412 | 3276522 | Average Cons Position = LG06 30.7 cM: Q6SS00 YABBY-like transcription factor GRAMINIFOLIA 5E-96 |
| TA52412_3847 | | Glycine_max_release_2 | 3273416 | 3276522 | YABBY-like transcription factor GRAMINIFOLIA [Antirrhinum majus (Garden snapdragon)] |
| Cf1177d | | Chafa1_1clean | 3273757 | 3276225 | NA |
| TA3613_3848 | | Glycine_soja_release_2 | 3273754 | 3276461 | YABBY-like transcription factor GRAMINIFOLIA [Antirrhinum majus (Garden snapdragon)] |
| BARCSOYSSR_03_0188 | | Wm82_potential_SSR | 3275263 | 3275282 | NA |
| Cf21553d | | Chafa1_1clean | 3274365 | 3276226 | NA |
| BP041062 | | LJGI.070108 | 3274309 | 3276373 | homologue to UniRef100_Q6SS00 Cluster: YABBY-like transcription factor GRAMINIFOLIA, n = 1, Antirrhinum majus|Rep: YABBY-like transcription factor GRAMINIFOLIA - Antirrhinum majus (Garden snapdragon), partial (46%) |
| CD416578 | | Glycine_max_release_2 | 3274359 | 3276514 | YABBY-like transcription factor GRAMINIFOLIA [Antirrhinum majus (Garden snapdragon)] |
| CD414741 | | Glycine_max_release_2 | 3274379 | 3276514 | YABBY-like transcription factor GRAMINIFOLIA [Antirrhinum majus (Garden snapdragon)] |
| AW311204 | | Glycine_max_release_2 | 3275751 | 3276514 | YABBY-like transcription factor GRAMINIFOLIA [Antirrhinum majus (Garden snapdragon)] |
| CD390542 | | Glycine_max_release_2 | 3276017 | 3276470 | NA |
| BARCSOYSSR_03_0189 | | Wm82_potential_SSR | 3276885 | 3276948 | NA |
| Glyma03g03510 | | Glyma1 | 3282203 | 3283893 | ID: PTHR23258 (Panther) = SERINE-THREONINE PROTEIN KINASE, PLANT-TYPE |
| BM094865 | | Glycine_max_release_2 | 3298597 | 3298959 | NA |
| BI698917 | | Glycine_max_release_2 | 3298949 | 3299117 | Cytochrome P450 monooxygenase CYP83E8 [Glycine max (Soybean)] |
| Pvcon9484 | | Phaseolus_vulgaris | 3298902 | 3299318 | UniRef100_Q2LAL4 Cytochrome P450 monooxygenase CYP83E8 n = 1 Tax = Glycine max RepID = Q2LAL4_SOYBN 2.00E-56 |
| BARC-031833-07221 | | marker_map4 | 3298950 | 3299349 | NA |
| BARC-028619-05977 | | Wm82xPI468916 | 3298952 | 3299501 | NA |
| BM526084 | | Glycine_soja_release_2 | 3299204 | 3299786 | Cytochrome P450 monooxygenase CYP83A [Glycine max (Soybean)] |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| TC373025 | | GMGI.042210 | 3299110 | 3299920 | UniRef100_Q2LAL4 Cytochrome P450 monooxygenase CYP83E8 - *Glycine max* (Soybean), partial (29%) |
| TC371473 | | GMGI.042210 | 3298933 | 3300311 | homologue to UniRef100_Q2LAL4 Cytochrome P450 monooxygenase CYP83E8 - *Glycine max* (Soybean), partial (47%) |
| BE658696 | | Glycine_max_release_2 | 3298946 | 3300315 | Cytochrome P450 monooxygenase CYP83E8 [*Glycine max* (Soybean)] |
| BU080942 | | Glycine_max_release_2 | 3299348 | 3299922 | Cytochrome P450 monooxygenase CYP83E8 [*Glycine max* (Soybean)] |
| CA820617 | | GMGI.042210 | 3299236 | 3300308 | UniRef100_Q2LAL4 Cytochrome P450 monooxygenase CYP83E8 - *Glycine max* (Soybean), partial (30%) |
| Glyma03g03520 | | Glyma1 | 3298597 | 3301147 | ID: GO: 0004497 (GO) = monooxygenase activity; ID: GO: 0005506 (GO) = iron ion binding; ID: GO: 0009055 (GO) = electron carrier activity; ID: GO: 0020037 (GO) = heme binding; ID: K00517 (KO) = E1.14.—.—; [EC: 1.14.—.—] [COG: COG2124]; ID: KOG0156 (KOG) = Cytochrome P450 CYP2 subfamily; ID: PF00067 (PFAM) = Cytochrome P450; ID: PTHR19383 (Panther) = CYTOCHROME P450 |
| Glyma03g03530 | | Glyma1 | 3298597 | 3301147 | NA |
| TA41485_3847 | | Glycine_max_release_2 | 3298610 | 3301147 | Cytochrome P450 monooxygenase CYP83E8 [*Glycine max* (Soybean)] |
| TC349887 | | GMGI.042210 | 3298612 | 3301147 | UniRef100_Q2LAL4 Cytochrome P450 monooxygenase CYP83E8 - *Glycine max* (Soybean), complete |
| BE610066 | | Glycine_max_release_2 | 3299270 | 3300511 | Cytochrome P450 monooxygenase CYP83E8 [*Glycine max* (Soybean)] |
| DQ340234.1 | | GenBank | 3298639 | 3301147 | cytochrome P450 monooxygenase CYP83E8 (CYP83E8) mRNA |
| Gm_W82_CR03.G19650 | | Gm_W82_CR03 | 3298597 | 3301192 | Average Cons Position = LG06 30.7 cM: Q2LAL4 Cytochrome P450 monooxygenase CYP83E8 1E-104; Q2MJ14 Cytochrome P450 monooxygenase CYP83E8 1E-74 |
| Gm_W82_CR03.G19660 | | Gm_W82_CR03 | 3298597 | 3301192 | Average Cons Position = LG06 30.7 cM: Q2LAL4 Cytochrome P450 monooxygenase |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| TA2512_3848 | | Glycine_soja_release_2 | 3298823 | 3301065 | CYP83E8 0; Q2MJ14 Cytochrome P450 monooxygenase CYP83E8 1E-162 Cytochrome P450 monooxygenase CYP83A [*Glycine max* (Soybean)] |
| BQ785233 | | Glycine_max_release_2 | 3299398 | 3301060 | Cytochrome P450 monooxygenase CYP83E8 [*Glycine max* (Soybean)] |
| TA41499_3847 | | Glycine_max_release_2 | 3299888 | 3300578 | Cytochrome P450 monooxygenase CYP83E8 [*Glycine max* (Soybean)] |
| BM177920 | | GMGI.042210 | 3300031 | 3300450 | UniRef100_Q2LAL4 Cytochrome P450 monooxygenase CYP83E8 - *Glycine max* (Soybean), partial (19%) |
| BI892902 | | Glycine_max_release_2 | 3300324 | 3300877 | Cytochrome P450 monooxygenase CYP83E8 [*Glycine max* (Soybean)] |
| BE806353 | | Glycine_max_release_2 | 3300458 | 3300769 | Cytochrome P450 monooxygenase CYP83E8 [*Glycine max* (Soybean)] |
| BF009836 | | Glycine_max_release_2 | 3300695 | 3301046 | Cytochrome P450 monooxygenase CYP83E8 [*Glycine max* (Soybean)] |
| NGMAX006078495 | 30 | | 3302666 | 3302967 | |
| NS0262836 | 31 | | | | |
| Glyma03g03540 | | Glyma1 | 3319774 | 3321759 | ID: GO: 0004497 (GO) = monooxygenase activity; ID: GO: 0005506 (GO) = iron ion binding; ID: GO: 0009055 (GO) = electron carrier activity; ID: GO: 0020037 (GO) = heme binding; ID: KOG0156 (KOG) = Cytochrome P450 CYP2 subfamily; ID: PF00067 (PFAM) = Cytochrome P450; ID: PTHR19383 (Panther) = CYTOCHROME P450 |
| Gm_W82_CR03.G19670 | | Gm_W82_CR03 | 3319774 | 3321759 | Average Cons Position = LG06 30.8 cM: Q2LAL4 Cytochrome P450 monooxygenase CYP83E8 1E-141; Q2MJ14 Cytochrome P450 monooxygenase CYP83E8 1E-109 |
| CV535331 | | Phaseolus_vulgaris | 3321369 | 3321648 | UniRef100_Q2LAL4 Cytochrome P450 monooxygenase CYP83E8 n = 1 Tax = *Glycine max* RepID = Q2LAL4_SOYBN 1.00E-34 |
| 117509_1962_0397 | | cajanus_cajan | 3321863 | 3321957 | NA |
| Contig30301 | | cajanus_cajan | 3321862 | 3321958 | NA |
| Contig5456 | | cajanus_cajan | 3321879 | 3321947 | NA |
| Contig2767 | | cajanus_cajan | 3321862 | 3321990 | NA |
| BARCSOYSSR_03_0190 | | Wm82_potential_SSR | 3325908 | 3325927 | NA |
| Cfl7433d | | Chafa1_1clean | 3328712 | 3328856 | NA |
| Glyma03g03550 | | Glyma1 | 3328724 | 3335906 | ID: GO: 0004497 (GO) = monooxygenase |

| Locus/Display Name (1) | SEQ ID NO: | Source (3) | Start Base (4) | End Base (5) | Additional Locus Information (6) |
|---|---|---|---|---|---|
| | | | | | activity; ID: GO: 0005506 (GO) = iron ion binding; ID: GO: 0009055 (GO) = electron carrier activity; ID: GO: 0020037 (GO) = heme binding; ID: KOG0156 (KOG) = Cytochrome P450 CYP2 subfamily; ID: PF00067 (PFAM) = Cytochrome P450; ID: PTHR19383 (Panther) = CYTOCHROME P450 |
| Gm_W82_CR03.G19680 | | Gm_W82_CR03 | 3328724 | 3335906 | Average Cons Position = LG06 30.8 cM: Q2LAL4 Cytochrome P450 monooxygenase CYP83E8 1E−180; Q2MJ14 Cytochrome P450 monooxygenase CYP83E8 1E−162 |
| TC418102 | | GMGI.042210 | 3298810 | 3366106 | UniRef100_Q2LAL4 Cytochrome P450 monooxygenase CYP83E8 - *Glycine max* (Soybean), partial (32%) |
| ss181360642 | | Wm82xPI468916 | 3333672 | 3333793 | NA |
| NGMAX006078838 | 5 | | 3335895 | 3336196 | |
| BARCSOYSSR_03_0191 | | Wm82_potential_SSR | 3337556 | 3337597 | NA |
| SATT152 | | | 3338479 | 3338729 | |
| Satt152 | | marker_map4 | 3338479 | 3338729 | NA |
| BARCSOYSSR_03_0192 | | Wm82_potential_SSR | 3338620 | 3338682 | NA |
| BARCSOYSSR_03_0193 | | Wm82_potential_SSR | 3338831 | 3338878 | NA |
| BARCSOYSSR_03_0194 | | Wm82_potential_SSR | 3343344 | 3343393 | NA |
| BARCSOYSSR_03_0195 | | Wm82_potential_SSR | 3343831 | 3343884 | NA |
| Gm_W82_CR03.G19690 | | Gm_W82_CR03 | 3344402 | 3346608 | Average Cons Position = LG06 30.9 cM: Q2LAL4 Cytochrome P450 monooxygenase CYP83E8 0; Q2MJ14 Cytochrome P450 monooxygenase CYP83E8 1E−166 |
| Glyma03g03560 | | Glyma1 | 3344405 | 3346608 | ID: GO: 0004497 (GO) = monooxygenase activity; ID: GO: 0005506 (GO) = iron ion binding; ID: GO: 0009055 (GO) = electron carrier activity; ID: GO: 0020037 (GO) = heme binding; ID: KOG0156 (KOG) = Cytochrome P450 CYP2 subfamily; ID: PF00067 (PFAM) = Cytochrome P450; ID: PTHR19383 (Panther) = CYTOCHROME P450 |
| DT083744 | | Glycine_soja_release_2 | 3346117 | 3346593 | Cytochrome P450 monooxygenase CYP83A [*Glycine max* (Soybean)] |
| Glyma03g03570 | | Glyma1 | 3365144 | 3365263 | NA |
| Gm_W82_CR03.G19700 | | Gm_W82_CR03 | 3365144 | 3365263 | Average Cons Position = LG06 31 cM: Q9T0K5 Extensin-like protein 2E−8; Q9SN46 Extensin-like protein 9E−8 |
| BARCSOYSSR_03_0196 | | Wm82_potential_SSR | 3366060 | 3366097 | NA |
| 373244_3126_3343 | | cajanus_cajan | 3372997 | 3373302 | NA |
| BARCSOYSSR_03_0197 | | Wm82_potential_SSR | 3374862 | 3374925 | NA |

Table 2 of the Specification.

| Locus/Display Name (1) | SEQ ID NO: | Source (3) | Start Base (4) | End Base (5) | Additional Locus Information (6) |
|---|---|---|---|---|---|
| BE021801 | | Glycine_max_release_2 | 3375080 | 3375675 | RuBisCO-associated protein [*Glycine max* (Soybean)] |
| Glyma03g03580 | | Glyma1 | 3375014 | 3376090 | NA |
| Gm_W82_CR03.G19710 | | Gm_W82_CR03 | 3375014 | 3376090 | Average Cons Position = LG06 31 cM: P39657 RuBisCO-associated protein 7E−52; Q2HU30 2-S globulin 2E−35 |
| TC379722 | | GMGI.042210 | 3375263 | 3375949 | weakly similar to UniRef100_P39657 RuBisCO-associated protein - *Glycine max* (Soybean), partial (31%) |
| TA65108_3847 | | Glycine_max_release_2 | 3375299 | 3375949 | RuBisCO-associated protein [*Glycine max* (Soybean)] |
| NGMAX006079484 | 6 | | 3389647 | 3389948 | |
| ss181360636 | | Wm82xPI468916 | 3390391 | 3390512 | NA |
| NGMAX006079502 | 7 | | 3390962 | 3391263 | |
| BARCSOYSSR_03_0198 | | Wm82_potential_SSR | 3392252 | 3392297 | NA |
| BARCSOYSSR_03_0199 | | Wm82_potential_SSR | 3397544 | 3397571 | NA |
| TC376705 | | GMGI.042210 | 3399170 | 3399602 | similar to UniRef100_Q2LAL4 Cytochrome P450 monooxygenase CYP83E8 - *Glycine max* (Soybean), partial (26%) |
| TA68858_3847 | | Glycine_max_release_2 | 3399170 | 3399761 | Cytochrome P450 monooxygenase CYP83H2 [*Medicago truncatula* (Barrel medic)] |
| BQ742710 | | GMGI.042210 | 3399724 | 3400146 | weakly similar to UniRef100_Q2LAL4 Cytochrome P450 monooxygenase CYP83E8 - *Glycine max* (Soybean), partial (24%) |
| BQ742710 | | Glycine_max_release_2 | 3399724 | 3400170 | Cytochrome P450 monooxygenase CYP83H2 [*Medicago truncatula* (Barrel medic)] |
| Glyma03g03590 | | Glyma1 | 3399194 | 3401129 | ID: GO: 0004497 (GO) = monooxygenase activity; ID: GO: 0005506 (GO) = iron ion binding; ID: GO: 0009055 (GO) = electron carrier activity; ID: GO: 0020037 (GO) = heme binding; ID: KOG0156 (KOG) = Cytochrome P450 CYP2 subfamily; ID: PF00067 (PFAM) = Cytochrome P450; ID: PTHR19383 (Panther) = CYTOCHROME P450 |
| TC379046 | | GMGI.042210 | 3400601 | 3401037 | similar to UniRef100_Q2LAL4 Cytochrome P450 monooxygenase CYP83E8 - *Glycine max* (Soybean), partial (29%) |
| TA64119_3847 | | Glycine_max_release_2 | 3400601 | 3401129 | Cytochrome P450 monooxygenase CYP83E8 [*Glycine max* (Soybean)] |
| WmFPC_Contig1249 | | Wm82 | 3269223 | 3539380 | NA |
| BARCSOYSSR_03_0200 | | Wm82_potential_SSR | 3411398 | 3411447 | NA |
| Gm_W82_CR03.G19720 | | Gm_W82_CR03 | 3399152 | 3432251 | Average Cons Position = LG06 31.2 cM: Q2LAL4 Cytochrome |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| | | | | | P450 monooxygenase CYP83E8 1E-178; Q2MJ14 Cytochrome P450 monooxygenase CYP83E8 1E-161 |
| BARCSOYSSR_03_0201 | | Wm82_potential_SSR | 3416401 | 3416428 | NA |
| Glyma03g03610 | | Glyma1 | 3417813 | 3418036 | ID: PTHR23354 (Panther) = NUCLEOLAR PROTEIN 7/ESTROGEN RECEPTOR COACTIVATOR-RELATED |
| Glyma03g03620 | | Glyma1 | 3420542 | 3421382 | ID: PTHR11353: SF19 (Panther) = CHAPERONIN CONTAINING T-COMPLEX PROTEIN 1, THETA SUBUNIT, TCPQ |
| Gm_W82_CR03.G19940 | | Gm_W82_CR03 | 3420542 | 3421382 | Average Cons Position = LG06 31.2 cM: Q75HJ3 Putative TCP-1/cpn60 chaperonin family protein 2E-14 |
| BARCSOYSSR_03_0202 | | Wm82_potential_SSR | 3428245 | 3428290 | NA |
| asmbl_1396 | | Vigna_unguiculata | 3430242 | 3431029 | NA |
| Glyma03g03630 | | Glyma1 | 3430214 | 3432112 | ID: GO: 0004497 (GO) = monooxygenase activity; ID: GO: 0005506 (GO) = iron ion binding; ID: GO: 0009055 (GO) = electron carrier activity; ID: GO: 0020037 (GO) = heme binding; ID: KOG0156 (KOG) = Cytochrome P450 CYP2 subfamily; ID: PF00067 (PFAM) = Cytochrome P450; ID: PTHR19383 (Panther) = CYTOCHROME P450 |
| Cf884d | | Chafa1_1clean | 3399773 | 3462808 | NA |
| TC383713 | | GMGI.042210 | 3430945 | 3431920 | similar to UniRef100_Q2LAL4 Cytochrome P450 monooxygenase CYP83E8 - *Glycine max* (Soybean), partial (41%) |
| TA64120_3847 | | Glycine_max_release_2 | 3430945 | 3432088 | Cytochrome P450 monooxygenase CYP83E8 [*Glycine max* (Soybean)] |
| Gm_W82_CR03.G19950 | | Gm_W82_CR03 | 3434392 | 3437069 | Average Cons Position = LG06 31.2 cM: Q2LAL4 Cytochrome P450 monooxygenase CYP83E8 0; Q2MJ14 Cytochrome P450 monooxygenase CYP83E8 1E-168 |
| Glyma03g03640 | | Glyma1 | 3434532 | 3437069 | ID: GO: 0004497 (GO) = monooxygenase activity; ID: GO: 0005506 (GO) = iron ion binding; ID: GO: 0009055 (GO) = electron carrier activity; ID: GO: 0020037 (GO) = heme binding; ID: K00517 (KO) = E1.14.—.—; [EC: 1.14.—.—] [COG: COG2124]; ID: KOG0156 (KOG) = Cytochrome P450 |

Table 2 of the Specification.

| Locus/Display Name (1) | SEQ ID NO: | Source (3) | Start Base (4) | End Base (5) | Additional Locus Information (6) |
|---|---|---|---|---|---|
| | | | | | CYP2 subfamily; ID: PF00067 (PFAM) = Cytochrome P450; ID: PTHR19383 (Panther) = CYTOCHROME P450 |
| BARCSOYSSR_03_0203 | | Wm82_potential_SSR | 3441948 | 3441974 | NA |
| Contig41065 | | cajanus_cajan | 3444039 | 3444288 | NA |
| Cf19649d | | Chafa1_1clean | 3444522 | 3444589 | NA |
| Glyma03g03660 | | Glyma1 | 3453314 | 3454353 | ID: PTHR10641 (Panther) = MYB-RELATED |
| Gm_W82_CR03.G19960 | | Gm_W82_CR03 | 3453314 | 3454353 | Average Cons Position = LG06 31.3 cM: O04498 F21M12.15 protein 1E−13; Q8W149 CDC5 protein 1E−13 |
| CX529111 | | MTGI.071708 | 3454177 | 3454324 | UniRef100_A7QMU6 Cluster: Chromosome chr14 scaffold_128, whole genome shotgun sequence, n = 1, *Vitis vinifera*|Rep: Chromosome chr14 scaffold_128, whole genome shotgun sequence - *Vitis vinifera* (Grape), partial (5%) |
| NGMAX006079911 | 20 | | 3454832 | 3455133 | |
| TA76562_3847 | | Glycine_max_release_2 | 3460426 | 3460986 | Cytochrome P450 monooxygenase CYP83H2 [*Medicago truncatula* (Barrel medic)] |
| TC353924 | | GMGI.042210 | 3460363 | 3462296 | similar to UniRef100_Q2LAL4 Cytochrome P450 monooxygenase CYP83E8 - *Glycine max* (Soybean), partial (55%) |
| Glyma03g03670 | | Glyma1 | 3460363 | 3463031 | ID: GO: 0004497 (GO) = monooxygenase activity; ID: GO: 0005506 (GO) = iron ion binding; ID: GO: 0009055 (GO) = electron carrier activity; ID: GO: 0020037 (GO) = heme binding; ID: KOG0156 (KOG) = Cytochrome P450 CYP2 subfamily; ID: PF00067 (PFAM) = Cytochrome P450; ID: PTHR19383 (Panther) = CYTOCHROME P450 |
| asmbl_1397 | | Vigna_unguiculata | 3461063 | 3462810 | NA |
| BM526518 | | Glycine_soja_release_2 | 3461266 | 3462638 | Cytochrome P450 monooxygenase CYP83A [*Glycine max* (Soybean)] |
| TA74906_3847 | | Glycine_max_release_2 | 3461106 | 3462803 | Cytochrome P450 monooxygenase CYP83H2 [*Medicago truncatula* (Barrel medic)] |
| TC350978 | | GMGI.042210 | 3461205 | 3463031 | similar to UniRef100_Q2MJ14 Cytochrome P450 monooxygenase CYP83E8 - *Medicago truncatula* (Barrel medic), partial (45%) |
| Contig16050 | | cajanus_cajan | 3463437 | 3463904 | NA |
| Glyma03g03680 | | Glyma1 | 3463500 | 3463884 | ID: GO: 0003735 (GO) = structural |

Table 2 of the Specification.

| Locus/Display Name (1) | SEQ ID NO: | Source (3) | Start Base (4) | End Base (5) | Additional Locus Information (6) |
|---|---|---|---|---|---|
| | | | | | constituent of ribosome; ID: GO: 0005622 (GO) = intracellular; ID: GO: 0005840 (GO) = ribosome; ID: GO: 0006412 (GO) = protein biosynthesis; ID: PF00318 (PFAM) = Ribosomal protein S2; ID: PTHR12534 (Panther) = 30S RIBOSOMAL PROTEIN S2 (PROKARYOTIC AND ORGANELLAR) |
| Gm_W82_CR03.G19980 | | Gm_W82_CR03 | 3463500 | 3463884 | Average Cons Position = LG06 31.3 cM: Q2PMT2 Chloroplast 30S ribosomal protein S2 5E−66; A4GGA8 Ribosomal protein S2 3E−60 |
| 282842_2235_0300 | | cajanus_cajan | 3463717 | 3463904 | NA |
| SAT_186 | | | 3465323 | 3465611 | |
| Sat_186 | | marker_map4 | 3465323 | 3465611 | NA |
| BARCSOYSSR_03_0204 | | Wm82_potential_SSR | 3465436 | 3465507 | NA |
| Glyma03g03690 | | Glyma1 | 3466673 | 3467512 | ID: PTHR19383 (Panther) = CYTOCHROME P450 |
| Gm_W82_CR03.G19990 | | Gm_W82_CR03 | 3466673 | 3467512 | Average Cons Position = LG06 31.3 cM: Q2LAL4 Cytochrome P450 monooxygenase CYP83E8 2E−59; Q2MJ14 Cytochrome P450 monooxygenase CYP83E8 6E−53 |
| Gm_W82_CR03.G19970 | | Gm_W82_CR03 | 3460310 | 3482068 | Average Cons Position = LG06 31.4 cM: Q2LAL4 Cytochrome P450 monooxygenase CYP83E8 1E−174; Q2MJ14 Cytochrome P450 monooxygenase CYP83E8 1E−174; Q2LAL4 Cytochrome P450 monooxygenase CYP83E8 1E−174; Q2MJ14 Cytochrome P450 monooxygenase CYP83E8 1E−174 |
| BARCSOYSSR_03_0205 | | Wm82_potential_SSR | 3480208 | 3480258 | NA |
| Glyma03g03700 | | Glyma1 | 3479524 | 3482068 | ID: PTHR19383 (Panther) = CYTOCHROME P450 |
| TA71903_3847 | | Glycine_max_release_2 | 3481704 | 3482068 | Cytochrome P450 monooxygenase CYP83H2 [*Medicago truncatula* (Barrel medic)] |
| Contig35199 | | cajanus_cajan | 3494004 | 3494295 | NA |
| Contig3959 | | cajanus_cajan | 3494076 | 3494316 | NA |
| 048713_3862_0404 | | cajanus_cajan | 3494085 | 3494309 | NA |
| Contig13534 | | cajanus_cajan | 3494085 | 3494316 | NA |
| Contig26881 | | cajanus_cajan | 3494172 | 3494315 | NA |
| Glyma03g03710 | | Glyma1 | 3496238 | 3496656 | ID: PTHR19383 (Panther) = CYTOCHROME P450 |

Table 2 of the Specification.

| Locus/Display Name (1) | SEQ ID NO: | Source (3) | Start Base (4) | End Base (5) | Additional Locus Information (6) |
|---|---|---|---|---|---|
| Gm_W82_CR03.G20000 | | Gm_W82_CR03 | 3496238 | 3496656 | Average Cons Position = LG06 31.5 cM: Q2LAL4 Cytochrome P450 monooxygenase CYP83E8 1E-28; Q2MJ14 Cytochrome P450 monooxygenase CYP83E8 3E-24 |
| AI855899 | | GMGI.042210 | 3498286 | 3498702 | similar to UniRef100_O23451 Retrotransposon like protein - *Arabidopsis thaliana* (Mouse-ear cress), partial (18%) |
| Glyma03g03720 | | Glyma1 | 3496909 | 3507131 | ID: GO: 0004497 (GO) = monooxygenase activity; ID: GO: 0005506 (GO) = iron ion binding; ID: GO: 0009055 (GO) = electron carrier activity; ID: GO: 0020037 (GO) = heme binding; ID: KOG0156 (KOG) = Cytochrome P450 CYP2 subfamily; ID: PF00067 (PFAM) = Cytochrome P450; ID: PTHR19383 (Panther) = CYTOCHROME P450 |
| Gm_W82_CR03.G20010 | | Gm_W82_CR03 | 3496909 | 3507191 | Average Cons Position = LG06 31.5 cM: Q2LAL4 Cytochrome P450 monooxygenase CYP83E8 0; Q2MJ14 Cytochrome P450 monooxygenase CYP83E8 1E-176; Q2LAL4 Cytochrome P450 monooxygenase CYP83E8 1E-173; Q2MJ14 Cytochrome P450 monooxygenase CYP83E8 1E-167 |
| DY577297 | | Glycine_max_release_2 | 3502642 | 3506305 | Cytochrome P450 monooxygenase CYP83H2 [*Medicago truncatula* (Barrel medic)] |
| TC390056 | | GMGI.042210 | 3506393 | 3507131 | similar to UniRef100_Q2LAL4 Cytochrome P450 monooxygenase CYP83E8 - *Glycine max* (Soybean), partial (43%) |
| BU090520 | | Glycine_max_release_2 | 3506586 | 3507131 | Cytochrome P450 monooxygenase CYP83H2 [*Medicago truncatula* (Barrel medic)] |
| BARCSOYSSR_03_0206 | | Wm82_potential_SSR | 3509060 | 3509091 | NA |
| Glyma03g03730 | | Glyma1 | 3519958 | 3523194 | ID: PF07160 (PFAM) = Protein of unknown function (DUF1395) |
| Cf6842d | | Chafa1_1clean | 3519956 | 3523224 | NA |
| NGMAX006080509 | 38 | | 3523345 | 3523646 | |
| BARCSOYSSR_03_0207 | | Wm82_potential_SSR | 3532126 | 3532179 | NA |
| TA57125_3847 | | Glycine_max_release_2 | 3533027 | 3533555 | NA |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| Glyma03g03740 | | Glyma1 | 3533027 | 3534997 | NA |
| TC382189 | | GMGI.042210 | 3533027 | 3534997 | homologue to UniRef100__A4TTL5 Membrane protein - *Magnetospirillum gryphiswaldense*, partial (7%) |
| TA57124__3847 | | Glycine__max__release__2 | 3533481 | 3534997 | NA |
| 186545__1436__2413 | | cajanus__cajan | 3539771 | 3539988 | NA |
| 351424__2925__3351 | | cajanus__cajan | 3539773 | 3539988 | NA |
| Contig20883 | | cajanus__cajan | 3539773 | 3539988 | NA |
| Contig14745 | | cajanus__cajan | 3539774 | 3539988 | NA |
| Contig38065 | | cajanus__cajan | 3539781 | 3539989 | NA |
| Contig6509 | | cajanus__cajan | 3539784 | 3539988 | NA |
| 219748__2942__0753 | | cajanus__cajan | 3539790 | 3539988 | NA |
| 293431__2369__2884 | | cajanus__cajan | 3539793 | 3539988 | NA |
| Contig27022 | | cajanus__cajan | 3539767 | 3540015 | NA |
| Contig42885 | | cajanus__cajan | 3539793 | 3539992 | NA |
| Contig4926 | | cajanus__cajan | 3539802 | 3540002 | NA |
| TC412519 | | GMGI.042210 | 3547628 | 3547947 | similar to UniRef100__A5KCL8 Variable surface protein Vir24-related - *Plasmodium vivax*, partial (5%) |
| 303716__2876__1271 | | cajanus__cajan | 3548384 | 3548512 | NA |
| Cf17931d | | Chafa1__1clean | 3548408 | 3548488 | NA |
| BG046534 | | Glycine__soja__release__2 | 3547861 | 3549153 | Hypothetical protein P0018A03.7 [*Oryza sativa* (*japonica* cultivar-group)] |
| Cf19308d | | Chafa1__1clean | 3548421 | 3549288 | NA |
| 131874__4007__0807 | | cajanus__cajan | 3549054 | 3549310 | NA |
| BQ785172 | | Glycine__max__release__2 | 3548932 | 3549589 | F20B17.3 [*Arabidopsis thaliana* (Mouse-ear cress)] |
| Glyma03g03750 | | Glyma1 | 3547452 | 3551110 | ID: K08869 (KO)=; ID: KOG1235 (KOG) = Predicted unusual protein kinase; ID: PF03109 (PFAM) = ABC1 family; ID: PTHR10566 (Panther) = CHAPERONE-ACTIVITY OF BC1 COMPLEX (CABC1)-RELATED |
| Cf17860d | | Chafa1__1clean | 3549758 | 3550319 | NA |
| Cf14536d | | Chafa1__1clean | 3550122 | 3550244 | NA |
| Cf5190d | | Chafa1__1clean | 3550872 | 3551786 | NA |
| AW736224 | | MTGI.071708 | 3550986 | 3551846 | similar to UniRef100__Q9MA15 Cluster: Uncharacterized aarF domain-containing protein kinase At1g79600, chloroplast precursor, n = 2, *Arabidopsis thaliana*|Rep: Uncharacterized aarF domain-containing protein kinase At1g79600, chloroplast precursor - *Arabidopsis thaliana* (Mouse-ear cress), partial (9%) |
| AW459587 | | GMGI.042210 | 3551428 | 3551782 | similar to UniRef100__Q9MA15 Uncharacterized aarF domain-containing protein kinase At1g79600, chloroplast precursor - *Arabidopsis thaliana* (Mouse-ear cress), partial (6%) |

Table 2 of the Specification.

| Locus/Display Name (1) | SEQ ID NO: | Source (3) | Start Base (4) | End Base (5) | Additional Locus Information (6) |
|---|---|---|---|---|---|
| TA71197_3847 | | Glycine_max_release_2 | 3551413 | 3552423 | NA |
| BI321376 | | GMGI.042210 | 3552012 | 3552423 | similar to UniRef100_A7SRH1 Predicted protein - *Nematostella vectensis* (Starlet sea anemone), partial (3%) |
| NGMAX006080885 | 8 | | 3561914 | 3562215 | |
| BARCSOYSSR_03_0208 | | Wm82_potential_SSR | 3578993 | 3579090 | NA |
| 225723_2718_2863 | | cajanus_cajan | 3581358 | 3581429 | NA |
| Contig36250 | | cajanus_cajan | 3581439 | 3581816 | NA |
| asmbl_1398 | | Vigna_unguiculata | 3581431 | 3582042 | NA |
| TA49427_3847 | | Glycine_max_release_2 | 3581425 | 3582129 | GRAS transcription factor [*Medicago truncatula* (Barrel medic)] |
| Cfl5586d | | Chafa1_1clean | 3581734 | 3581838 | NA |
| BE820512 | | Glycine_max_release_2 | 3581448 | 3582150 | GRAS transcription factor [*Medicago truncatula* (Barrel medic)] |
| TA7292_34305 | | Lotus_japonicus_release_1 | 3581441 | 3582214 | GRAS transcription factor [*Medicago truncatula* (Barrel medic)] |
| TC27537 | | LJGI.070108 | 3581441 | 3582214 | weakly similar to UniRef100_A7PYF4 Cluster: Chromosome chr15 scaffold_37, whole genome shotgun sequence, n = 1, *Vitis vinifera*\|Rep: Chromosome chr15 scaffold_37, whole genome shotgun sequence - *Vitis vinifera* (Grape), partial (21%) |
| TC365523 | | GMGI.042210 | 3581299 | 3582452 | weakly similar to UniRef100_A7PYF4 Chromosome chr15 scaffold_37, whole genome shotgun sequence - *Vitis vinifera* (Grape), partial (23%) |
| TC369657 | | GMGI.042210 | 3581425 | 3582630 | weakly similar to UniRef100_A7PYF4 Chromosome chr15 scaffold_37, whole genome shotgun sequence - *Vitis vinifera* (Grape), partial (30%) |
| Cfl3385d | | Chafa1_1clean | 3581734 | 3582618 | NA |
| TA49425_3847 | | Glycine_max_release_2 | 3581746 | 3582728 | GRAS transcription factor [*Medicago truncatula* (Barrel medic)] |
| TA4094_3848 | | Glycine_soja_release_2 | 3581788 | 3582699 | Scarecrow-like 6 [*Arabidopsis thaliana* (Mouse-ear cress)] |
| TC354455 | | GMGI.042210 | 3581939 | 3582741 | similar to UniRef100_A7PYF4 Chromosome chr15 scaffold_37, whole genome shotgun sequence - *Vitis vinifera* (Grape), partial (22%) |
| Pvcon6489 | | Phaseolus_vulgaris | 3581822 | 3582979 | UniRef100_A7PYF4 Chromosome chr15 scaffold_37, whole genome shotgun sequence n = 1 Tax = *Vitis vinifera* RepID = A7PYF4_VITVI 1.00E−117 |
| TA5736_3885 | | Phaseolus_vulgaris_release_2 | 3581822 | 3582979 | GRAS transcription factor [*Medicago truncatula* (Barrel medic)] |

Table 2 of the Specification.

| Locus/Display Name (1) | SEQ ID NO: | Source (3) | Start Base (4) | End Base (5) | Additional Locus Information (6) |
| --- | --- | --- | --- | --- | --- |
| EX304728 | | Phaseolus_vulgaris | 3582172 | 3582953 | UniRef100_A7PYF4 Chromosome chr15 scaffold_37, whole genome shotgun sequence n = 1 Tax = *Vitis vinifera* RepID = A7PYF4_VITVI 9.00E−62 |
| Cfl4326d | | Chafa1_1clean | 3582263 | 3582870 | NA |
| AV419737 | | Lotus_japonicus_release_1 | 3582457 | 3582866 | GRAS transcription factor [*Medicago truncatula* (Barrel medic)] |
| AV419737 | | LJGI.070108 | 3582470 | 3582866 | similar to UniRef100_A7PYF4 Cluster: Chromosome chr15 scaffold_37, whole genome shotgun sequence, n = 1, *Vitis vinifera*|Rep: Chromosome chr15 scaffold_37, whole genome shotgun sequence - *Vitis vinifera* (Grape), partial (15%) |
| Gm_W82_CR03.G20850 | | Gm_W82_CR03 | 3581403 | 3584467 | Average Cons Position = LG06 31.8 cM: Q8LL10 Hairy meristem 1E−105 |
| Glyma03g03760 | | Glyma1 | 3581425 | 3584467 | ID: PF03514 (PFAM) = GRAS family transcription factor |
| TA49424_3847 | | Glycine_max_release_2 | 3582576 | 3583493 | GRAS transcription factor [*Medicago truncatula* (Barrel medic)] |
| asmbl_1399 | | Vigna_unguiculata | 3582925 | 3583548 | NA |
| TC384787 | | GMGI.042210 | 3582755 | 3583811 | similar to UniRef100_A7PYF4 Chromosome chr15 scaffold_37, whole genome shotgun sequence - *Vitis vinifera* (Grape), partial (8%) |
| Contig33774 | | cajanus_cajan | 3583334 | 3583523 | NA |
| BM107962 | | Glycine_max_release_2 | 3583135 | 3583811 | GRAS transcription factor [*Medicago truncatula* (Barrel medic)] |
| BM526478 | | Glycine_soja_release_2 | 3583674 | 3584202 | NA |
| TC399328 | | GMGI.042210 | 3583626 | 3584467 | similar to UniRef100_A7PYF4 Chromosome chr15 scaffold_37, whole genome shotgun sequence - *Vitis vinifera* (Grape), partial (4%) |
| BARCSOYSSR_03_0209 | | Wm82_potential_SSR | 3585574 | 3585641 | NA |
| BARCSOYSSR_03_0210 | | Wm82_potential_SSR | 3597635 | 3597672 | NA |
| Glyma03g03770 | | Glyma1 | 3600654 | 3600771 | NA |
| BARCSOYSSR_03_0211 | | Wm82_potential_SSR | 3602587 | 3602608 | NA |
| BARCSOYSSR_03_0212 | | Wm82_potential_SSR | 3608155 | 3608176 | NA |
| BARCSOYSSR_03_0213 | | Wm82_potential_SSR | 3608387 | 3608446 | NA |
| AW598654 | | Glycine_max_release_2 | 3613044 | 3613631 | FACT complex subunit SSRP1 [*Vicia faba* (Broad bean)] |
| 183966_2432_1637 | | cajanus_cajan | 3613341 | 3613924 | NA |
| 328630_4036_3779 | | cajanus_cajan | 3614035 | 3614253 | NA |
| Contig39949 | | cajanus_cajan | 3614034 | 3614741 | NA |
| Contig12168 | | cajanus_cajan | 3614710 | 3614977 | NA |
| Gm_W82_CR03.G21470 | | Gm_W82_CR03 | 3612970 | 3619158 | Average Cons Position = LG06 31.9 cM: O04235 FACT complex subunit SSRP1 0 |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| Glyma03g03780 | | Glyma1 | 3613002 | 3619158 | ID: GO: 0003677 (GO) = DNA binding; ID: GO: 0005634 (GO) = nucleus; ID: K09272 (KO)=; ID: KOG0526 (KOG) = Nucleosome-binding factor SPN, POB3 subunit; ID: PF00505 (PFAM) = HMG (high mobility group) box; ID: PTHR13711 (Panther) = SWI/SNF-RELATED CHROMATIN BINDING PROTEIN |
| Cf1771d | | Chafa1_1clean | 3613313 | 3618874 | NA |
| Contig22956_primers | | cajanus_cajan | 3616077 | 3616304 | NA |
| Contig22956 | | cajanus_cajan | 3615797 | 3616789 | NA |
| BG508541 | | Glycine_max_release_2 | 3616283 | 3617889 | FACT complex subunit SSRP1 [*Vicia faba* (Broad bean)] |
| TC394940 | | GMGI.042210 | 3615339 | 3619158 | homologue to UniRef100_O04235 FACT complex subunit SSRP1 - *Vicia faba* (Broad bean), partial (52%) |
| asmbl_1400 | | Vigna_unguiculata | 3616459 | 3618878 | NA |
| Contig45189_primers | | cajanus_cajan | 3617561 | 3617828 | NA |
| Contig45189 | | cajanus_cajan | 3617516 | 3617932 | NA |
| Cf4868d | | Chafa1_1clean | 3629189 | 3629480 | NA |
| Glyma03g03790 | | Glyma1 | 3629021 | 3632958 | ID: PF00036 (PFAM) = EF hand; ID: PTHR10891 (Panther) = CALMODULIN |
| Gm_W82_CR03.G21680 | | Gm_W82_CR03 | 3629021 | 3632958 | Average Cons Position = LG06 32 cM: Q01IH6 OSIGBa0159I10.9 protein 2E−24; Q9FDZ8 At1g73440 1E−22; Q01IH6 OSIGBa0159I10.9 protein 1E−22; Q9FDZ8 At1g73440 3E−22 |
| Cf19325d | | Chafa1_1clean | 3630769 | 3632619 | NA |
| DQ117561 | | Phaseolus_vulgaris_release_2 | 3630860 | 3632639 | Calcium-binding EF-hand; Ubiquitin interacting motif [*Medicago truncatula* (Barrel medic)] |
| BI699366 | | Glycine_max_release_2 | 3632020 | 3632958 | At1g73440 [*Arabidopsis thaliana* (Mouse-ear cress)] |
| BARCSOYSSR_03_0214 | | Wm82_potential_SSR | 3632687 | 3632736 | NA |
| 312855_0711_3271 | | cajanus_cajan | 3633856 | 3634022 | NA |
| 265958_3391_1857_primers | | cajanus_cajan | 3634131 | 3635827 | NA |
| Cf7889d | | Chafa1_1clean | 3634101 | 3635886 | NA |
| 265958_3391_1857 | | cajanus_cajan | 3634130 | 3635954 | NA |
| Contig15510 | | cajanus_cajan | 3633837 | 3636562 | NA |
| asmbl_1401 | | Vigna_unguiculata | 3633846 | 3636561 | NA |
| BE658586 | | Glycine_max_release_2 | 3633896 | 3637470 | Putative VAMP-associated protein [*Arabidopsis thaliana* (Mouse-ear cress)] |
| TC372625 | | GMGI.042210 | 3633896 | 3637470 | similar to UniRef100_A8W459 Vesicle-associated protein - *Medicago truncatula* (Barrel medic), partial (72%) |
| Glyma03g03800 | | Glyma1 | 3633770 | 3638147 | ID: GO: 0005198 (GO) = structural molecule |

Table 2 of the Specification.

| Locus/Display Name (1) | SEQ ID NO: | Source (3) | Start Base (4) | End Base (5) | Additional Locus Information (6) |
|---|---|---|---|---|---|
| | | | | | activity; ID: KOG0439 (KOG) = VAMP-associated protein involved in inositol metabolism; ID: PF00635 (PFAM) = MSP (Major sperm protein) domain; ID: PTHR10809 (Panther) = VESICLE-ASSOCIATED MEMBRANE PROTEIN (VAMP) |
| Gm_W82_CR03.G21690 | | Gm_W82_CR03 | 3633770 | 3638151 | Average Cons Position = LG06 32 cM: A8W459 Vesicle-associated protein 5E−98; Q7XM58 OSJNBb0020O11.15 protein 3E−11 |
| TC356639 | | GMGI.042210 | 3633778 | 3638147 | similar to UniRef100_A8W459 Vesicle-associated protein - *Medicago truncatula* (Barrel medic), partial (98%) |
| TA48856_3847 | | Glycine_max_release_2 | 3633830 | 3638098 | F11M15.13 protein [*Arabidopsis thaliana* (Mouse-ear cress)] |
| Pvcon2313 | | Phaseolus_vulgaris | 3633861 | 3638070 | UniRef100_A8W459 Vesicle-associated protein n = 1 Tax = *Medicago truncatula* RepID = A8W459_MEDTR 1.00E−110 |
| CA801352 | | Glycine_max_release_2 | 3636253 | 3636956 | Putative VAMP-associated protein (At2g45140) (Putative VAMP (Vesicle-associated membrane protein)-associated protein) [*Arabidopsis thaliana* (Mouse-ear cress)] |
| CA801352 | | GMGI.042210 | 3636557 | 3636956 | homologue to UniRef100_A8W459 Vesicle-associated protein - *Medicago truncatula* (Barrel medic), partial (28%) |
| 135152_1291_2482 | | cajanus_cajan | 3636646 | 3636929 | NA |
| CA411541 | | Lupinus_albus_release_2 | 3636648 | 3638013 | F11M15.13 protein [*Arabidopsis thaliana* (Mouse-ear cress)] |
| AW598332 | | Glycine_max_release_2 | 3636682 | 3638032 | Putative VAMP-associated protein [*Arabidopsis thaliana* (Mouse-ear cress)] |
| CK606662 | | Glycine_max_release_2 | 3636684 | 3638114 | F11M15.13 protein [*Arabidopsis thaliana* (Mouse-ear cress)] |
| TA4535_3886 | | Phaseolus_coccineus_release_2 | 3636737 | 3638091 | Putative VAMP-associated protein [*Arabidopsis thaliana* (Mouse-ear cress)] |
| Contig23898 | | cajanus_cajan | 3637449 | 3638104 | NA |
| Contig23898_primers | | cajanus_cajan | 3637768 | 3637969 | NA |
| Contig21922 | | cajanus_cajan | 3644450 | 3644630 | NA |
| Cf16623d | | Chafa1_1clean | 3644762 | 3644875 | NA |
| TC33304 | | LJGI.070108 | 3644744 | 3645015 | similar to UniRef100_A7PYF8 Cluster: Chromosome chr15 scaffold_37, whole genome shotgun |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| | | | | | sequence, n = 1, *Vitis vinifera*\|Rep: Chromosome chr15 scaffold_37, whole genome shotgun sequence - *Vitis vinifera* (Grape), partial (28%) |
| TA13096_34305 | | Lotus_japonicus_release_1 | 3644744 | 3645016 | Hypothetical protein T8B10_250 [*Arabidopsis thaliana* (Mouse-ear cress)] |
| Glyma03g03810 | | Glyma1 | 3644726 | 3645652 | NA |
| asmbl_1402 | | Vigna_unguiculata | 3645125 | 3645437 | NA |
| Pvcon2861 | | Phaseolus_vulgaris | 3645118 | 3645700 | UniRef100_A7PYF8 Chromosome chr15 scaffold_37, whole genome shotgun sequence n = 1 Tax = *Vitis vinifera* RepID = A7PYF8_VITVI 1.00E−131 |
| BARCSOYSSR_03_0215 | | Wm82_potential_SSR | 3648008 | 3648059 | NA |
| BARCSOYSSR_03_0216 | | Wm82_potential_SSR | 3648947 | 3648980 | NA |
| 079763_0879_0568 | | cajanus_cajan | 3659098 | 3659198 | NA |
| Cf19857d | | Chafa1_1clean | 3674397 | 3674718 | NA |
| NGMAX006081942 | 32 | | 3675970 | 3676271 | |
| Gm_W82_CR03.G22310 | | Gm_W82_CR03 | 3674151 | 3678330 | Average Cons Position = LG06 32.1 cM: Q7XJM6 At2g45130 protein 2E−62; UPI000023DC34 hypothetical protein FG01544.1 9E−11 |
| Glyma03g03820 | | Glyma1 | 3674153 | 3678330 | ID: PTHR10783 (Panther) = XENOTROPIC AND POLYTROPIC MURINE LEUKEMIA VIRUS RECEPTOR |
| Cf21636d | | Chafa1_1clean | 3678001 | 3678119 | NA |
| NGMAX006081999 | 33 | | 3688804 | 3689105 | |
| 214701_1085_2819 | | cajanus_cajan | 3696674 | 3696867 | NA |
| TC354431 | | GMGI.042210 | 3696212 | 3698076 | weakly similar to UniRef100_Q40287 Anthocyanidin 3-O-glucosyltransferase - *Manihot esculenta* (Cassava) (Manioc), partial (25%) |
| TA65213_3847 | | Glycine_max_release 2 | 3696212 | 3698092 | Putative flavonol 3-O-glucosyltransferase [*Arabidopsis thaliana* (Mouse-ear cress)] |
| Glyma03g03830 | | Glyma1 | 3696212 | 3698853 | ID: KOG1192 (KOG) = UDP-glucuronosyl and UDP-glucosyl transferase; ID: PTHR11926 (Panther) = GLUCOSYL/GLUCURONOSYL TRANSFERASES |
| Gm_W82_CR03.G22320 | | Gm_W82_CR03 | 3696212 | 3698880 | Average Cons Position = LG06 32.2 cM: Q40287 Anthocyanidin 3-O-glucosyltransferase 1E−100 |
| BARCSOYSSR_03_0217 | | Wm82_potential_SSR | 3697753 | 3697776 | NA |
| 223169_0358_1790 | | cajanus_cajan | 3698268 | 3698529 | NA |
| BI973614 | | Glycine_max_release_2 | 3698266 | 3698839 | NA |
| 222017_1187_2363 | | cajanus_cajan | 3698533 | 3698709 | NA |
| 214701_1085_2819 | | cajanus_cajan | 3718709 | 3718902 | NA |
| Glyma03g03840 | | Glyma1 | 3718497 | 3720038 | ID: PTHR11926 (Panther) = GLUCOSYL/GLUCURONOSYL TRANSFERASES |
| Gm_W82_CR03.G22330 | | Gm_W82_CR03 | 3718497 | 3720038 | Average Cons Position = LG06 32.3 cM: Q9ZU72 Putative flavonol |

Table 2 of the Specification.

| Locus/Display Name (1) | SEQ ID NO: | Source (3) | Start Base (4) | End Base (5) | Additional Locus Information (6) |
|---|---|---|---|---|---|
| | | | | | 3-O-glucosyltransferase 1E−52; Q9ZU71 Putative flavonol 3-O-glucosyltransferase 7E−50 |
| CA936681 | | Glycine_max_release_2 | 3720697 | 3720966 | NA |
| BG045196 | | Glycine_soja_release_2 | 3720668 | 3721159 | AT3g50740/T3A5_120 [*Arabidopsis thaliana* (Mouse-ear cress)] |
| 214701_1085_2819 | | cajanus_cajan | 3720896 | 3721089 | NA |
| Glyma03g03850 | | Glyma1 | 3720509 | 3723198 | ID: KOG1192 (KOG) = UDP-glucuronosyl and UDP-glucosyl transferase; ID: PTHR11926 (Panther) = GLUCOSYL/GLUCURONOSYL TRANSFERASES |
| Gm_W82_CR03.G22340 | | Gm_W82_CR03 | 3720509 | 3723198 | Average Cons Position = LG06 32.3 cM: Q40287 Anthocyanidin 3-O-glucosyltransferase 1E−102 |
| BARCSOYSSR_03_0218 | | Wm82_potential_SSR | 3721975 | 3721994 | NA |
| BG362737 | | Glycine_max_release_2 | 3722227 | 3722623 | NA |
| 223169_0358_1790 | | cajanus_cajan | 3722497 | 3722758 | NA |
| TC377946 | | GMGI.042210 | 3722365 | 3723183 | similar to UniRef100_A7QXH2 Chromosome undetermined scaffold_224, whole genome shotgun sequence - *Vitis vinifera* (Grape), partial (8%) |
| 222017_1187_2363 | | cajanus_cajan | 3722772 | 3722938 | NA |
| NGMAX006082115 | 34 | | 3723411 | 3723712 | |
| Glyma03g03860 | | Glyma1 | 3739483 | 3743064 | ID: PTHR11926 (Panther) = GLUCOSYL/GLUCURONOSYL TRANSFERASES |
| Gm_W82_CR03.G22350 | | Gm_W82_CR03 | 3739483 | 3743064 | Average Cons Position = LG06 32.4 cM: Q9ZU72 Putative flavonol 3-O-glucosyltransferase 3E−30; Q9ZU71 Putative flavonol 3-O-glucosyltransferase 4E−28 |
| 214701_1085_2819 | | cajanus_cajan | 3742136 | 3742309 | NA |
| BARCSOYSSR_03_0219 | | Wm82_potential_SSR | 3743233 | 3743280 | NA |
| WmFPC_Contig2577 | | Wm82 | 3597056 | 3899983 | NA |
| 214701_1085_2819 | | cajanus_cajan | 3767176 | 3767369 | NA |
| Glyma03g03870 | | Glyma1 | 3766840 | 3769211 | ID: KOG1192 (KOG) = UDP-glucuronosyl and UDP-glucosyl transferase; ID: PTHR11926 (Panther) = GLUCOSYL/GLUCURONOSYL TRANSFERASES |
| BARCSOYSSR_03_0220 | | Wm82_potential_SSR | 3768104 | 3768125 | NA |
| Gm_W82_CR03.G22360 | | Gm_W82_CR03 | 3766840 | 3769398 | Average Cons Position = LG06 32.5 cM: Q40287 Anthocyanidin 3-O-glucosyltransferase 1E−100 |
| 223169_0358_1790 | | cajanus_cajan | 3768626 | 3768887 | NA |
| 222017_1187_2363 | | cajanus_cajan | 3768901 | 3769067 | NA |
| BARCSOYSSR_03_0221 | | Wm82_potential_SSR | 3780830 | 3780877 | NA |
| Glyma03g03880 | | Glyma1 | 3780953 | 3782165 | ID: PTHR10110: SF2 (Panther) = SODIUM/HYDROGEN EXCHANGER (NA+/H+ ANTIPORTER NHX) |
| Gm_W82_CR03.G22370 | | Gm_W82_CR03 | 3780953 | 3782165 | Average Cons Position = LG06 32.5 cM: Q5XWR7 Sodium/hydrogen exchanger 6E−41; Q4VT46 |

Table 2 of the Specification.

| Locus/Display Name (1) | SEQ ID NO: | Source (3) | Start Base (4) | End Base (5) | Additional Locus Information (6) |
|---|---|---|---|---|---|
| NGMAX006082688 | 35 | | 3783513 | 3783814 | Sodium/hydrogen exchanger 4E−40 |
| 120013_0199_0726 | | cajanus_cajan | 3795534 | 3795754 | NA |
| Contig10071 | | cajanus_cajan | 3795582 | 3795791 | NA |
| TC404918 | | GMGI.042210 | 3796084 | 3796372 | similar to UniRef100_A7PKJ2 Chromosome chr15 scaffold_19, whole genome shotgun sequence - *Vitis vinifera* (Grape), partial (6%) |
| NS0118425 | 37 | | 3797329 | 3796787 | |
| Glyma03g03890 | | Glyma1 | 3795505 | 3806070 | ID: PF03828 (PFAM) = Poly(A) polymerase; ID: PTHR23092 (Panther) = FAMILY NOT NAMED |
| Gm_W82_CR03.G22380 | | Gm_W82_CR03 | 3795505 | 3806070 | Average Cons Position = LG06 32.6 cM: Q8RX81 AT4g00060/F6N15_10 0 |
| NS0138011 | 9 | | 3800866 | 3801607 | |
| BM309798 | | Glycine_max_release_2 | 3800952 | 3802710 | AT4g00060/F6N15_10 [*Arabidopsis thaliana* (Mouse-ear cress)] |
| TC415453 | | GMGI.042210 | 3800952 | 3802834 | similar to UniRef100_A7PKJ2 Chromosome chr15 scaffold_19, whole genome shotgun sequence - *Vitis vinifera* (Grape), partial (3%) |
| TC415366 | | GMGI.042210 | 3800607 | 3805890 | similar to UniRef100_A7PKJ2 Chromosome chr15 scaffold_19, whole genome shotgun sequence - *Vitis vinifera* (Grape), partial (8%) |
| TA59649_3847 | | Glycine_max_release_2 | 3800607 | 3805959 | AT4g00060/F6N15_10 [*Arabidopsis thaliana* (Mouse-ear cress)] |
| TC398829 | | GMGI.042210 | 3803354 | 3804019 | NA |
| BI469325 | | Glycine_max_release_2 | 3803354 | 3804126 | NA |
| 376070_3692_2835 | | cajanus_cajan | 3803828 | 3804020 | NA |
| TA59648_3847 | | Glycine_max_release_2 | 3804176 | 3806049 | NA |
| TC370427 | | GMGI.042210 | 3804176 | 3806049 | UniRef100_O28156 Uncharacterized protein AF_2124 - *Archaeoglobus fulgidus*, partial (7%) |
| GD950777 | | GMGI.042210 | 3804468 | 3805861 | NA |
| TA59650_3847 | | Glycine_max_release_2 | 3805151 | 3806065 | NA |
| TC349966 | | GMGI.042210 | 3805151 | 3806073 | NA |
| NGMAX006082778 | 36 | | 3806350 | 3806651 | |
| NGMAX006082782 | 25 | | 3808878 | 3809179 | |
| BARCSOYSSR_03_0222 | | Wm82_potential_SSR | 3817624 | 3817665 | NA |
| Glyma03g03910 | | Glyma1 | 3814802 | 3820907 | ID: GO: 0004659 (GO) = prenyltransferase activity; ID: GO: 0016021 (GO) = integral to membrane; ID: PF01040 (PFAM) = UbiA prenyltransferase family; ID: PTHR11048 (Panther) = PRENYLTRANSFERASES |
| Gm_W82_CR03.G22790 | | Gm_W82_CR03 | 3814802 | 3820907 | Average Cons Position = LG06 32.8 cM: Q647J9 Homogentisate phytylprenyltransferase 1E−123; Q58FG4 Homogentisate |

Table 2 of the Specification.

| Locus/Display Name (1) | SEQ ID NO: | Source (3) | Start Base (4) | End Base (5) | Additional Locus Information (6) |
|---|---|---|---|---|---|
| | | | | | phytylprenyltransferase 1E−120 |
| 086263__3714__2178 | | cajanus_cajan | 3820244 | 3820452 | NA |
| TA67363_3847 | | Glycine_max_release_2 | 3825407 | 3826540 | NA |
| TC382671 | | GMGI.042210 | 3825409 | 3826540 | similar to UniRef100__A7PKJ1 Chromosome chr15 scaffold_19, whole genome shotgun sequence - *Vitis vinifera* (Grape), partial (23%) |
| 059050__2801__0639 | | cajanus_cajan | 3826082 | 3826873 | NA |
| Cf8743d | | Chafa1__1clean | 3826817 | 3827351 | NA |
| GD676001 | | GMGI.042210 | 3827061 | 3827202 | NA |
| BARC-064351-18627 | | marker_map4 | 3826875 | 3827418 | NA |
| Glyma03g03920 | | Glyma1 | 3826814 | 3829735 | ID: 3.1.—.—(EC) = Acting on ester bonds.; ID: GO: 0005737 (GO) = cytoplasm; ID: GO: 0006281 (GO) = DNA repair; ID: GO: 0006310 (GO) = DNA recombination; ID: GO: 0006974 (GO) = response to DNA damage stimulus; ID: GO: 0016788 (GO) = hydrolase activity, acting on ester bonds; ID: K07447 (KO) =; ID: PF03652 (PFAM) = Uncharacterised protein family (UPF0081) |
| Cf19457d | | Chafa1__1clean | 3829491 | 3829653 | NA |
| TA60403_3847 | | Glycine_max_release_2 | 3831923 | 3832830 | NA |
| TC406296 | | GMGI.042210 | 3832100 | 3833014 | NA |
| 046766__3073__1326 | | cajanus_cajan | 3832854 | 3833064 | NA |
| BI973221 | | Glycine_max_release_2 | 3832711 | 3833221 | NA |
| BI973221 | | GMGI.042210 | 3832796 | 3833221 | similar to UniRef100__A7U5Z3 Glucan synthase catalytic, partial (0%) |
| Glyma03g03930 | | Glyma1 | 3831954 | 3839129 | ID: PTHR23067 (Panther) = DOUBLE-STRANDED RNA-BINDING ZINC FINGER PROTEIN |
| BU544624 | | Glycine_max_release_2 | 3837285 | 3837804 | NA |
| TC395926 | | GMGI.042210 | 3837285 | 3837973 | similar to UniRef100__A6Q8J9 NADH-quinone oxidoreductase, chain K - *Sulfurovum* sp. (strain NBC37-1), partial (17%) |
| AW201693 | | Glycine_max_release_2 | 3837556 | 3837973 | NA |
| CA785507 | | GMGI.042210 | 3838481 | 3838623 | NA |
| Glyma03g03940 | | Glyma1 | 3845294 | 3846057 | NA |
| NGMAX006083256 | 26 | | 3861274 | 3861575 | |
| 186230__3992__3930 | | cajanus_cajan | 3865200 | 3865357 | NA |
| Gm_W82_CR03.G23030 | | Gm_W82_CR03 | 3865550 | 3866901 | Average Cons Position = LG06 33.2 cM: Q4U316 Cys2/His2 zinc-finger transcription factor 3E−43; O22090 ZPT3-3 6E−43 |
| Glyma03g03950 | | Glyma1 | 3865609 | 3866901 | ID: GO: 0005622 (GO) = intracellular; ID: GO: 0008270 (GO) = zinc ion binding; ID: PF00096 (PFAM) = Zinc finger, |

Table 2 of the Specification.

| Locus/Display Name (1) | SEQ ID NO: | Source (3) | Start Base (4) | End Base (5) | Additional Locus Information (6) |
|---|---|---|---|---|---|
| TC392384 | | GMGI.042210 | 3866249 | 3866901 | C2H2 type; ID: PTHR11389 (Panther) = ZINC FINGER PROTEIN similar to UniRef100_A7PKI9 Chromosome chr15 scaffold_19, whole genome shotgun sequence - *Vitis vinifera* (Grape), partial (26%) |
| TA2788_3848 | | Glycine_soja_release_2 | 3868578 | 3869195 | NA |
| DT084159 | | Glycine_soja_release_2 | 3868668 | 3869195 | NA |
| Glyma03g03960 | | Glyma1 | 3876581 | 3877716 | ID: PTHR23258 (Panther) = SERINE-THREONINE PROTEIN KINASE, PLANT-TYPE |
| NGMAX006083447 | 27 | | 3877288 | 3877589 | |
| Glyma03g03970 | | Glyma1 | 3882286 | 3882732 | NA |
| Gm_W82_CR03.G23450 | | Gm_W82_CR03 | 3882286 | 3882732 | Average Cons Position = LG06 33.3 cM: Q4U314 Cys2/His2 zinc-finger transcription factor 4E-41 |
| BARCSOYSSR_03_0223 | | Wm82_potential_SSR | 3888578 | 3888641 | NA |
| ss181361770 | | Wm82xPI468916 | 3889537 | 3889658 | NA |
| 261825_3183_0830 | | cajanus_cajan | 3889663 | 3889920 | NA |
| 061251_3291_1427 | | cajanus_cajan | 3889901 | 3890022 | NA |
| NGMAX006083554 | 28 | | 3891696 | 3891997 | |
| NGMAX006083631 | 10 | | 3901266 | 3901567 | |
| BARCSOYSSR_03_0224 | | Wm82_potential_SSR | 3906951 | 3907016 | NA |
| Glyma03g03980 | | Glyma1 | 3905784 | 3908385 | ID: PF01357 (PFAM) = Pollen allergen |
| Gm_W82_CR03.G23660 | | Gm_W82_CR03 | 3905784 | 3908385 | Average Cons Position = LG06 33.5 cM: A1X8W4 Beta expansin 1 precursor 2E-79 |
| CA908583 | | Phaseolus_coccineus_release_2 | 3905871 | 3908326 | Putative beta-expansin [*Eucalyptus globulus* (Blue gum)] |
| BARCSOYSSR_03_0225 | | Wm82_potential_SSR | 3908619 | 3908672 | NA |
| SATT009 | | | 3910203 | 3910364 | |
| BARCSOYSSR_03_0226 | | Wm82_potential_SSR | 3910260 | 3910307 | NA |
| Satt009 | | marker_map4 | 3910203 | 3910364 | NA |
| BARCSOYSSR_03_0227 | | Wm82_potential_SSR | 3910269 | 3910307 | NA |
| Contig43957 | | cajanus_cajan | 3911076 | 3911325 | NA |
| Contig33449 | | cajanus_cajan | 3911127 | 3911325 | NA |
| 000154_3576_0278 | | cajanus_cajan | 3911285 | 3911325 | NA |
| 003004_1235_1275 | | cajanus_cajan | 3911285 | 3911325 | NA |
| 006900_1493_1929 | | cajanus_cajan | 3911285 | 3911325 | NA |
| 007460_3338_1291 | | cajanus_cajan | 3911285 | 3911325 | NA |
| 014289_3939_0440 | | cajanus_cajan | 3911285 | 3911325 | NA |
| 025966_0192_2223 | | cajanus_cajan | 3911285 | 3911325 | NA |
| 026227_0909_1005 | | cajanus_cajan | 3911285 | 3911325 | NA |
| 026294_1598_2544 | | cajanus_cajan | 3911285 | 3911325 | NA |
| 028308_3640_0439 | | cajanus_cajan | 3911285 | 3911325 | NA |
| 037852_0303_1097 | | cajanus_cajan | 3911285 | 3911325 | NA |
| 040619_1093_1942 | | cajanus_cajan | 3911285 | 3911325 | NA |
| 043547_3658_3419 | | cajanus_cajan | 3911285 | 3911325 | NA |
| 053059_3470_1958 | | cajanus_cajan | 3911285 | 3911325 | NA |
| 056612_0743_3441 | | cajanus_cajan | 3911285 | 3911325 | NA |
| 059660_2583_1888 | | cajanus_cajan | 3911285 | 3911325 | NA |
| 062864_3768_3193 | | cajanus_cajan | 3911285 | 3911325 | NA |
| 063186_3037_2550 | | cajanus_cajan | 3911285 | 3911325 | NA |
| 066572_1541_3184 | | cajanus_cajan | 3911285 | 3911325 | NA |
| 070863_3199_3682 | | cajanus_cajan | 3911285 | 3911325 | NA |
| 081478_2276_2703 | | cajanus_cajan | 3911285 | 3911325 | NA |
| 095517_3300_2600 | | cajanus_cajan | 3911285 | 3911325 | NA |
| 096113_2367_0176 | | cajanus_cajan | 3911285 | 3911325 | NA |
| 102296_1998_2033 | | cajanus_cajan | 3911285 | 3911325 | NA |
| 102601_2987_3443 | | cajanus_cajan | 3911285 | 3911325 | NA |
| 102878_3507_1146 | | cajanus_cajan | 3911285 | 3911325 | NA |
| 104948_3016_0095 | | cajanus_cajan | 3911285 | 3911325 | NA |

-continued

Table 2 of the Specification.

| Locus/Display Name (1) | SEQ ID NO: | Source (3) | Start Base (4) | End Base (5) | Additional Locus Information (6) |
|---|---|---|---|---|---|
| 110539_3656_2013 | | cajanus_cajan | 3911285 | 3911325 | NA |
| 112098_1843_0592 | | cajanus_cajan | 3911285 | 3911325 | NA |
| 112753_1668_3825 | | cajanus_cajan | 3911285 | 3911325 | NA |
| 125992_3730_1890 | | cajanus_cajan | 3911285 | 3911325 | NA |
| 132002_0047_0182 | | cajanus_cajan | 3911285 | 3911325 | NA |
| 153038_2371_2695 | | cajanus_cajan | 3911285 | 3911325 | NA |
| 153557_3248_2660 | | cajanus_cajan | 3911285 | 3911325 | NA |
| 175695_2245_1739 | | cajanus_cajan | 3911285 | 3911325 | NA |
| 178644_1078_2444 | | cajanus_cajan | 3911285 | 3911325 | NA |
| 208712_2112_3215 | | cajanus_cajan | 3911285 | 3911325 | NA |
| 215158_3041_2690 | | cajanus_cajan | 3911285 | 3911325 | NA |
| 228589_1830_3910 | | cajanus_cajan | 3911285 | 3911325 | NA |
| 248892_2596_3299 | | cajanus_cajan | 3911285 | 3911325 | NA |
| 261459_3344_2358 | | cajanus_cajan | 3911285 | 3911325 | NA |
| 264549_3459_3346 | | cajanus_cajan | 3911285 | 3911325 | NA |
| 288926_0121_3928 | | cajanus_cajan | 3911285 | 3911325 | NA |
| 291320_3644_1895 | | cajanus_cajan | 3911285 | 3911325 | NA |
| 303787_1960_3525 | | cajanus_cajan | 3911285 | 3911325 | NA |
| Contig18363 | | cajanus_cajan | 3911285 | 3911325 | NA |
| Contig254 | | cajanus_cajan | 3911285 | 3911325 | NA |
| Contig29855 | | cajanus_cajan | 3911285 | 3911325 | NA |
| Contig38972 | | cajanus_cajan | 3911285 | 3911325 | NA |
| Contig4328 | | cajanus_cajan | 3911285 | 3911325 | NA |
| Contig6579 | | cajanus_cajan | 3911285 | 3911325 | NA |
| Contig6979 | | cajanus_cajan | 3911285 | 3911325 | NA |
| Contig911 | | cajanus_cajan | 3911285 | 3911325 | NA |
| Contig9432 | | cajanus_cajan | 3911285 | 3911325 | NA |
| 036604_1796_3446 | | cajanus_cajan | 3911285 | 3911331 | NA |
| 082281_3494_1612 | | cajanus_cajan | 3911285 | 3911331 | NA |
| 222096_3093_3876 | | cajanus_cajan | 3911285 | 3911331 | NA |
| BARCSOYSSR_03_0228 | | Wm82_potential_SSR | 3915417 | 3915468 | NA |
| 397302_2219_2548 | | cajanus_cajan | 3931040 | 3931321 | NA |
| 230041_2755_2778 | | cajanus_cajan | 3931097 | 3931329 | NA |
| Cf7593d | | Chafa1_1clean | 3931207 | 3931427 | NA |
| 039239_1483_0258 | | cajanus_cajan | 3931282 | 3931499 | NA |
| 320914_3315_2468 | | cajanus_cajan | 3931330 | 3931491 | NA |
| 039239_1483_0258_primers | | cajanus_cajan | 3931429 | 3932086 | NA |
| Glyma03g03990 | | Glyma1 | 3930986 | 3932577 | ID: KOG1674 (KOG) = Cyclin; ID: PF00134 (PFAM) = Cyclin, N-terminal domain; ID: PTHR15615 (Panther) = FAMILY NOT NAMED |
| Gm_W82_CR03.G23670 | | Gm_W82_CR03 | 3930986 | 3932577 | Average Cons Position = LG06 33.7 cM: Q9SHD3 Cyclin-U2-1 1E−79 |
| ss181361769 | | Wm82xPI468916 | 3934845 | 3934966 | NA |
| BARCSOYSSR_03_0229 | | Wm82_potential_SSR | 3935235 | 3935256 | NA |
| BARCSOYSSR_03_0230 | | Wm82_potential_SSR | 3938921 | 3938980 | NA |
| ss181361768 | | Wm82xPI468916 | 3944184 | 3944305 | NA |
| TA56046_3847 | | Glycine_max_release_2 | 3950098 | 3952011 | NA |
| TC352554 | | GMGI.042210 | 3950098 | 3952011 | similar to UniRef100_A7PKI5 Chromosome chr15 scaffold_19, whole genome shotgun sequence - *Vitis vinifera* (Grape), partial (30%) |
| Gm_W82_CR03.G23680 | | Gm_W82_CR03 | 3950090 | 3953935 | Average Cons Position = LG06 33.8 cM: Q8GZ38 Putative bHLH transcription factor bHLH016 1E−38 |
| Glyma03g04000 | | Glyma1 | 3950104 | 3953935 | ID: GO: 0030528 (GO) = transcription regulator activity; ID: GO: 0045449 (GO) = regulation of transcription; ID: PF00010 (PFAM) = Helix-loop-helix DNA-binding domain; |

Table 2 of the Specification.

| Locus/Display Name (1) | SEQ ID NO: | Source (3) | Start Base (4) | End Base (5) | Additional Locus Information (6) |
|---|---|---|---|---|---|
| | | | | | ID: PTHR23042 (Panther) = CIRCADIAN PROTEIN CLOCK/ARNT/BMAL/PAS |
| TA56045_3847 | | Glycine_max_release_2 | 3950331 | 3953930 | NA |
| TC375851 | | GMGI.042210 | 3950914 | 3953930 | similar to UniRef100_O81306 F6N15.11 protein - *Arabidopsis thaliana* (Mouse-ear cress), partial (25%) |
| BF715766 | | Glycine_soja_release_2 | 3951913 | 3953143 | Putative bHLH transcription factor [*Arabidopsis thaliana* (Mouse-ear cress)] |
| BG043888 | | Glycine_soja_release_2 | 3953326 | 3953902 | NA |
| Contig34254_primers | | cajanus_cajan | 3963399 | 3964485 | NA |
| Contig34254 | | cajanus_cajan | 3963346 | 3964851 | NA |
| CD404584 | | Glycine_max_release_2 | 3963347 | 3964851 | Sec61beta [*Medicago truncatula* (Barrel medic)] |
| TC374606 | | GMGI.042210 | 3963320 | 3965078 | NA |
| Glyma03g04010 | | Glyma1 | 3963336 | 3965289 | ID: KOG3457 (KOG) = Sec61 protein translocation complex, beta subunit; ID: PF03911 (PFAM) = Sec61beta family; ID: PTHR13509 (Panther) = FAMILY NOT NAMED |
| Gm_W82_CR03.G23690 | | Gm_W82_CR03 | 3963336 | 3965289 | Average Cons Position = LG06 33.9 cM: Q9M206 Transport protein subunit-like 9E−15 |
| BM085010 | | Glycine_max_release_2 | 3964232 | 3964709 | Sec61beta [*Medicago truncatula* (Barrel medic)] |
| TC400303 | | GMGI.042210 | 3964232 | 3964775 | NA |
| Cf14447d | | Chafa1_1clean | 3964462 | 3964710 | NA |
| Cf2942d | | Chafa1_1clean | 3964462 | 3964710 | NA |
| NS0202926 | 11 | | 3964906 | 3964512 | |
| Contig38009 | | cajanus_cajan | 3964588 | 3964869 | NA |
| Glyma03g04020 | | Glyma1 | 3968405 | 3971501 | ID: GO: 0004713 (GO) = protein-tyrosine kinase activity; ID: GO: 0005524 (GO) = ATP binding; ID: GO: 0006468 (GO) = protein amino acid phosphorylation; ID: KOG1187 (KOG) = Serine/threonine protein kinase; ID: PF07714 (PFAM) = Protein tyrosine kinase; ID: PTHR23258 (Panther) = SERINE-THREONINE PROTEIN KINASE, PLANT-TYPE |
| 296480_1060_0054 | | cajanus_cajan | 3970036 | 3970281 | NA |
| Contig33933 | | cajanus_cajan | 3971440 | 3971708 | NA |
| BARCSOYSSR_03_0231 | | Wm82_potential_SSR | 3972030 | 3972069 | NA |
| 127767_0193_0529 | | cajanus_cajan | 3972578 | 3972652 | NA |
| 086083_3139_0733 | | cajanus_cajan | 3972567 | 3972678 | NA |
| 107263_3116_1889 | | cajanus_cajan | 3972567 | 3972745 | NA |
| Contig3427 | | cajanus_cajan | 3972567 | 3972745 | NA |
| Contig8717 | | cajanus_cajan | 3972566 | 3972746 | NA |
| 339396_1511_0863 | | cajanus_cajan | 3972612 | 3972746 | NA |
| NGMAX006084289 | 12 | | 3979463 | 3979764 | |
| BARCSOYSSR_03_0232 | | Wm82_potential_SSR | 3982356 | 3982407 | NA |
| Gm_W82_CR03.G24110 | | Gm_W82_CR03 | 3992073 | 3996230 | Average Cons Position = LG06 34.2 cM: Q2YE87 NBS-LRR type disease resistance protein Rps1-k-2 0; Q2YE88 |

Table 2 of the Specification.

| Locus/Display Name (1) | SEQ ID NO: | Source (3) | Start Base (4) | End Base (5) | Additional Locus Information (6) |
|---|---|---|---|---|---|
| Glyma03g04030 | | Glyma1 | 3992594 | 3996230 | NBS-LRR type disease resistance protein Rps1-k-1 0 ID: GO: 0005515 (GO) = protein binding; ID: KOG4658 (KOG) = Apoptotic ATPase; ID: PF00560 (PFAM) = Leucine Rich Repeat; ID: PTHR23155 (Panther) = LEUCINE-RICH REPEAT-CONTAINING PROTEIN |
| BARCSOYSSR_03_0233 | | Wm82_potential_SSR | 4001862 | 4001917 | NA |
| Glyma03g04040 | | Glyma1 | 4017654 | 4019180 | NA |
| Gm_W82_CR03.G24720 | | Gm_W82_CR03 | 4017654 | 4019180 | Average Cons Position = LG06 34.3 cM: Q2YE87 NBS-LRR type disease resistance protein Rps1-k-2 0; Q2YE88 NBS-LRR type disease resistance protein Rps1-k-1 0 |
| Glyma03g04050 | | Glyma1 | 4027661 | 4027913 | ID: PTHR23346 (Panther) = TRANSLATIONAL ACTIVATOR GCN1-RELATED |
| Gm_W82_CR03.G24730 | | Gm_W82_CR03 | 4027661 | 4027913 | Average Cons Position = LG06 34.4 cM: Q53K35 HEAT repeat, putative 2E−14 |
| Glyma03g04060 | | Glyma1 | 4029392 | 4031456 | ID: PTHR11875: SF9 (Panther) = SET |
| Gm_W82_CR03.G24740 | | Gm_W82_CR03 | 4029392 | 4031456 | Average Cons Position = LG06 34.4 cM: Q9M9V0 F6A14.10 protein 2E−11; A9RDJ7 Nucleosome assembly protein family 8E−11 |
| Glyma03g04070 | | Glyma1 | 4032514 | 4033581 | ID: PTHR11043 (Panther) = ZETA-COAT PROTEIN |
| Gm_W82_CR03.G24750 | | Gm_W82_CR03 | 4032514 | 4033581 | Average Cons Position = LG06 34.5 cM: Q9MAZ9 Nonclathrin coat protein zeta1-COP 1E−13; A2Q5T5 Longin-like 7E−12 |
| 147515_0361_0524 | | cajanus_cajan | 4037444 | 4037666 | NA |
| AI443099 | | Glycine_max_release_2 | 4037901 | 4038186 | NBS-LRR type disease resistance protein Rps1-k-1 [*Glycine max* (Soybean)] |
| Glyma03g04080 | | Glyma1 | 4037251 | 4041010 | ID: GO: 0005515 (GO) = protein binding; ID: KOG4658 (KOG) = Apoptotic ATPase; ID: PF00560 (PFAM) = Leucine Rich Repeat; ID: PTHR23155 (Panther) = LEUCINE-RICH REPEAT-CONTAINING PROTEIN |
| Gm_W82_CR03.G24760 | | Gm_W82_CR03 | 4037251 | 4041010 | Average Cons Position = LG06 34.5 cM: Q2YE87 NBS-LRR type disease resistance protein Rps1-k-2 0; Q2YE88 NBS-LRR type disease resistance protein Rps1-k-1 0 |

Table 2 of the Specification.

| Locus/Display Name (1) | SEQ ID NO: | Source (3) | Start Base (4) | End Base (5) | Additional Locus Information (6) |
|---|---|---|---|---|---|
| BARCSOYSSR_03_0234 | | Wm82_potential_SSR | 4050233 | 4050272 | NA |
| 146317_0436_0220 | | cajanus_cajan | 4052175 | 4052344 | NA |
| 069073_0816_0074 | | cajanus_cajan | 4052178 | 4052368 | NA |
| Glyma03g04090 | | Glyma1 | 4065369 | 4065479 | ID: PTHR11550 (Panther) = CTP SYNTHASE |
| Gm_W82_CR03.G24770 | | Gm_W82_CR03 | 4065369 | 4065479 | Average Cons Position = LG06 34.5 cM: Q8L6Z9 CTP synthase-like protein 3E−9 |
| DT082886 | | Glycine_soja_release_2 | 4075130 | 4075437 | NA |

Sequences for the genes provided above can be obtained from the World Wide Web (or Internet) using the identifiers provided in Column 1 (Locus/Display Name) or Column 5 (ADDITIONAL LOCUS INFORMATION) from the following internet locations:

"soybase.org" (described in Grant et al., Nucleic Acids Research, 2010, Vol. 38, Database issue D843-D846) or soybase.org/gbrowse/cgi-bin/gbrowse/gmax1.01/ (see Hyten D L, Choi I-Y, Song Q, Specht J E, Carter T E et al. (2010) A high density integrated genetic linkage map of soybean and the development of a 1,536 Universal Soy Linkage Panel for QTL mapping. Crop Science 50:960-968. (Crop Science); and Hyten D L, Cannon S B, Song Q, Weeks N, Fickus E W et al. (2010) High-throughput SNP discovery through deep resequencing of a reduced representation library to anchor and orient scaffolds in the soybean whole genome sequence. BMC Genomics 11(1): 38);

"phytozome.net" or "phytozome.net/cgi-bin/gbrowse/soybeannname=Gm09";

"www.plantgdb.org" or "plantgdb.org/GmGDB/ (Assembly version Glyma1.170 (April 2009)"; and, "ncbi.nlm.nih.gov/sites/entrez" and subsites "ncbi.nlm.nih.gov/nucest", "ncbi.nlm.nih.gov/dbEST", "ncbi.nlm.nih.gov/genbank/", ".ncbi.nlm.nih.gov/sites/genome", "ncbi.nlm.nih.gov/unigene", and "ncbi.nlm.nih.gov/UniGene/UGOrg.cgi?TAXID=3847".

We claim:

1. A method for obtaining a soybean plant comprising in its genome at least one metribuzin tolerance locus, comprising the steps of:
   (a) genotyping a plurality of soybean plants with respect to at least one polymorphic genetic locus in a linkage group N genomic region with a nucleic acid marker located within NGMAX006079484 (SEQ ID NO: 6) or NGMAX006079502 (SEQ ID NO:7) or located between NGMAX006079484 (SEQ ID NO: 6) and NGMAX006080885 (SEQ ID NO:8);
   (b) identifying within the plurality of soybean plants a soybean plant having a genotype associated with metribuzin tolerance wherein the genotype comprises a TT allele located at nucleotide 201 of NGMAX006079502 (SEQ ID NO: 7) with the nucleic acid marker of step (a); and
   (c) isolating from the plurality of soybean plants the identified soybean plant of step (b) comprising in its genome the at least one genetic locus comprising the genotype associated with metribuzin tolerance.

2. The method of claim 1, wherein said nucleic acid marker is located within NGMAX006079484 (SEQ ID NO: 6) or NGMAX006079502 (SEQ ID NO:7).

3. The method of claim 1, wherein said nucleic acid marker comprises the TT allele located at nucleotide 201 of NGMAX006079502 (SEQ ID NO:7).

4. The method of claim 1, wherein said plurality of soybean plants comprises a population that is obtained by: i) crossing a parent plant comprising at least one metribuzin tolerance locus with a parent plant comprising at least one metribuzin sensitivity locus; or, ii) obtaining seed or progeny from a parental plant segregating for at least one metribuzin tolerance locus.

5. The method of claim 1, wherein said plurality of soybean plants contains plants that contain a transgene that confers resistance to dicamba and/or a transgene that confers resistance to glyphosate.

6. The method of claim 1, further comprising the step of assaying for the presence of at least one additional marker, wherein said additional marker is either linked or unlinked to said linkage group N genomic region.

7. The method of claim 1, wherein said method further comprises exposing the isolated soybean plant or progeny thereof to a metribuzin formulation to identify a metribuzin-tolerant soybean variety that exhibits an absence or reduction of leaf chlorosis, leaf necrosis, or plant death in comparison to a metribuzin-sensitive soybean variety exposed to the metribuzin.

8. The method of claim 7, wherein the progeny are exposed to the metribuzin formulation at a dosage of about 0.25 pounds per acre to about 0.75 pounds per acre.

9. A method for producing a soybean plant comprising in its genome at least one introgressed metribuzin tolerance locus comprising the steps of:
(a) crossing a first soybean plant with a metribuzin tolerance locus in a linkage group N genomic region flanked by loci NGMAX006077640 (SEQ ID NO: 3) and NS0138011 (SEQ ID NO: 9) with a second soybean plant comprising a metribuzin sensitivity locus in the linkage group N genomic region and at least one polymorphic locus that is linked to the linkage group N genomic region and that is not present in said first soybean plant to obtain a population segregating for the metribuzin tolerance loci and said polymorphic locus;
(b) detecting at least two polymorphic nucleic acids in at least one soybean plant from said population, wherein at least one of said polymorphic nucleic acids is detected with a first nucleic acid marker located within NGMAX006079484 (SEQ ID NO: 6) or NGMAX006079502 (SEQ ID NO:7) or located between NGMAX006079484 (SEQ ID NO: 6) and NGMAX006080885 (SEQ ID NO:8); in said linkage group N region and wherein at least one of said polymorphic nucleic acids is said polymorphic locus that is not present in said first soybean plant and that is detected with a second nucleic acid marker; and
(c) selecting a soybean plant comprising a genotype associated with metribuzin tolerance wherein the genotype comprises a TT allele located at nucleotide 201 of NGMAX00679502 (SEQ ID NO: 7) based on detection with the first nucleic acid marker of step (b) and at least one linked marker found in said second soybean plant comprising a metribuzin sensitivity locus but not found in said first soybean plant, thereby obtaining a soybean plant comprising in its genome an introgressed metribuzin tolerance locus.

10. The method of claim 9, wherein at least one of said first or said second soybean plants comprises a transgene that confers resistance to dicamba and/or a transgene that confers resistance to glyphosate.

11. The method of claim 9, wherein said population, said selected soybean plant and/or progeny of said selected soybean plant is exposed to a metribuzin formulation to identify a metribuzin tolerant soybean plant or progeny plant that exhibits an absence or reduction of leaf chlorosis, leaf necrosis, or plant death in comparison to a metribuzin-sensitive soybean variety exposed to the metribuzin formulation.

12. The method of claim 9, wherein said first nucleic acid marker is located within NGMAX006079484 (SEQ ID NO: 6) or NGMAX006079502 (SEQ ID NO: 7).

13. The method of claim 9, wherein said polymorphic nucleic acid detected in step (b) with the first nucleic acid marker comprises the TT allele located at nucleotide 201 of NGMAX006079502 (SEQ ID NO: 7).

14. The method of claim 9, wherein said linked polymorphic locus is detected with a genotypic marker, a phenotypic marker, or both.

15. The method of claim 14, wherein said linked polymorphic locus is detected with a marker that is located within about 1000, 500, 100, 40, 20, 10, or 5 kilobases (Kb) of said metribuzin tolerance locus.

16. The method of claim 15, wherein said linked polymorphic locus is detected with at least one marker selected from the group consisting of NGMAX006083631 (SEQ ID NO: 10), NS0202926 (SEQ ID NO: 11), NGMAX006084289 (SEQ ID NO: 12), and NGMAX006088354 (SEQ ID NO: 13).

17. A method for obtaining a soybean plant seed comprising in its genome at least one metribuzin tolerance locus, comprising the steps of:
(a) genotyping a plurality of soybean plants with respect to at least one polymorphic genetic locus in a linkage group N genomic region with a nucleic acid marker located within located within NGMAX006079484 (SEQ ID NO: 6) or NGMAX006079502 (SEQ ID NO:7) or located between NGMAX006079484 (SEQ ID NO: 6) and NGMAX006080885 (SEQ ID NO:8);
(b) identifying within the plurality of soybean plants a soybean plant having a genotype associated with metribuzin tolerance wherein the genotype comprises a TT allele located at nucleotide 201 of NGMAX00679502 (SEQ ID NO: 7) with the nucleic acid marker of step (a); and
(c) collecting a seed from the identified soybean plant of step (b) or from a cross with the identified soybean plant of step (b), wherein the seed comprises in its genome at least one genetic locus comprising the genotype associated with metribuzin tolerance.

18. The method of claim 17, wherein the nucleic acid marker is located within NGMAX006079484 (SEQ ID NO: 6) or NGMAX006079502 (SEQ ID NO:7).

19. The method of claim 18, wherein said nucleic acid marker comprises the TT allele located at nucleotide 201 of NGMAX006079502 (SEQ ID NO:7).

20. The method of claim 17, further comprising exposing progeny grown from the seed of the identified plant or from the seed of the cross to a metribuzin formulation to identify a metribuzin-tolerant soybean variety that exhibits an absence or reduction of leaf chlorosis, leaf necrosis, or plant death in comparison to a metribuzin-sensitive soybean variety exposed to the metribuzin formulation.

21. The method of claim 20, wherein the progeny grown from the seed of the identified plant or from the seed of the cross are exposed to the metribuzin formulation at a rate of about 0.25 pounds per acre to about 0.75 pounds per acre.

* * * * *

SEQUENCE LISTING

```
<160> NUMBER OF SEQ ID NOS: 42

<210> SEQ ID NO 1
<211> LENGTH: 333
<212> TYPE: DNA
<213> ORGANISM: Glycine max

<400> SEQUENCE: 1
atcggtgtta gagaacacgg aatgggagct atctgcaacg gcattgctct tcacagccct      60
ggactgattc catattgtgc aaccttcttt gtattcactg actacatgag aggtgccata     120
aggctttctg cgctgtctga ggctggggtt atttatgtca tgacccatga ttcaatagga     180
cttggagaag atgggccaac ccaccagcca attgagcacc tagcaagctt ccgggcaatg     240
ccaaacattt tgatgcttcg tcccgccgac ggtaacgaaa cagccggagc atacaaagtg     300
gccgtgctca acaggaagag accctccatt ctt                                  333

<210> SEQ ID NO 2
<211> LENGTH: 301
<212> TYPE: DNA
<213> ORGANISM: Glycine max
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t

<400> SEQUENCE: 2
```

```
gaaaaataat ttttatagta taatgttatt ttggatagtt caactttat tttnantttt      60 tttaaaattt gaagtatgaa tttattaatc aaattttgtt atatatatat atatataatt    120
attttaatat atattaggtt aaatcgggtt aattagtgac caccggttcg atgattgact    180
cacttattta ctacttcaat agggttggtg agtgggctga ttttcacaac aatgttcact    240
tcgatttgat ttttcggttg atgtctcttg cagtcgagtt gcaggatagt ttgggaaaaa    300
a                                                                    301
```

```
<210> SEQ ID NO 3
<211> LENGTH: 301
<212> TYPE: DNA
<213> ORGANISM: Glycine max
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t

<400> SEQUENCE: 3
```

```
cattttaaat gggaacaaaa ttgggatttc accccettga taaggaacca gaacacaaga     60
acaaaatgga tagggaccac ctttgatttc agacacagaa gggccggaac tatattatag    120
cccataaaaa aagtctncag tatagaattt gacaattgct aaggacacct ttcttgtttg    180
ctaaacgtac atccccgtgt atttttagtt taacttttaa aaaaatactg ctttttgaaa    240
agtgttaaaa tcttaacacc gtcaaaatta aaatttcgaa agtattatna cactttcag    300 a                                                                    301
```

```
<210> SEQ ID NO 4
<211> LENGTH: 301
<212> TYPE: DNA
<213> ORGANISM: Glycine max
<220> FEATURE:
<221> NAME/KEY: misc_feature
<222> LOCATION: (253)..(253)
<223> OTHER INFORMATION: n is a, c, g, or t

<400> SEQUENCE: 4
```

```
tgagttcaca accgttcctt atttatattt attcatttat tttcctactt ttttctggag     60
ttctactttt aagttgtttt aaatccacat ctaacattta ttccctggtt caccataaat    120
gaacgtaatc caatagtgct tttgatatat ataaagtttt tgcccctct aatctagcag    180 cagtgtgctt taattgacca aatcagattt cttctttt tttatttag ttttattaat     240 aagtaataac tgnctgtatt tgtagaaaaa aaatatataa ccagtaatct tggggtattg    300
a                                                                    301
```

```
<210> SEQ ID NO 5
<211> LENGTH: 301
<212> TYPE: DNA
<213> ORGANISM: Glycine max
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
```

<400> SEQUENCE: 5

```
tgaagggaga atagaggccc gtatttcttt naaagctgcc atagttgcag atgaagagct    60
gaattattca actgatgaag attccctatt atgggaaggc ctctaggacc aggtggaaag   120
ggtggcttct tgattgttct gctgttttgg aagaagaata gcaaaagcaa gggaagagta   180
aggcatataa ttagaagtgg tagtgacacc attgtggcct agctataacc aagaggtgga   240
agaaaagagt tataccaccc tatataggga catatntttt ttggtcttga gtgaaagatg   300
g                                                                  301
```

<210> SEQ ID NO 6
<211> LENGTH: 301
<212> TYPE: DNA
<213> ORGANISM: Glycine max
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 6

```
cttagcatcg attatgcncc aagcccacat gtcatttcca ttttctataa gccttttttg    60
tcttcttata catgggctta gtgccaacta cgcgctaatc cccaatgacc ttttccttc    120 ccgtgcatgg cttagtgcat cccacacgct aagccaaacc atcaataaat tttgtatcac   180
ttgggcttag cacncaccct ttctctaagc cactattccc ctaggacatt ttttgtgaat   240
tgtttgggct tagcacatcc cacttgctaa gcccaatttg tctaatgatt gggctaagcc   300
c                                                                  301
```

<210> SEQ ID NO 7
<211> LENGTH: 301
<212> TYPE: DNA
<213> ORGANISM: Glycine max
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (275)..(275)
<223> OTHER INFORMATION: n is a, c, g, or t

<400> SEQUENCE: 7

```
tcaagggaat ttcctcatac accttgacct ttgagtccnt gagccccatc atcaaccttg    60
cttatattca ataattgtt ggaatccagc agatacttnc gtagtttttt cggggccagg    120
gaaggctcag gctcntgtcg ttcntgatgc tnccccgacc acaccactag tcatccttcc   180
```

```
tctagtcccc actcctccaa tccttctctt tactcctcca aatcagctta ttcacatgat    240
gatgagtctt catcatggaa aacacctact tatgnagagt cttcataagc tctccttcca    300
t                                                                   301
```

```
<210> SEQ ID NO 8
<211> LENGTH: 301
<212> TYPE: DNA
<213> ORGANISM: Glycine max
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t

<400> SEQUENCE: 8
ttgatgcaaa nagtgtggtg taaattaaag gaaggggggng tgcttcttta ttctatagaa    60
ancatgtagg tttgttgtgt ccagattgca tancangaaa ggcacattga agtaaacatt    120
ttggaagtag ctaactagag agttgaacat gttatgtatg tagtggaagt ggaagtagag    180
gtgtgtgtgg atgtggaagg ttctgtttgg gtccatgcca aattcggcat tgcngaaggc    240
attttgctgc acttgctttc ctttctattc acctcatcct catggttttt ggtttacatt    300
c                                                                   301
```

```
<210> SEQ ID NO 9
<211> LENGTH: 742
<212> TYPE: DNA
<213> ORGANISM: Glycine max

<400> SEQUENCE: 9
gcgatatgat tccttttctt ccagctaaat gataattacc ttctttacag cattgatcca    60
attcacatag atgatcctct ttttccaaca aataatgtgg gaaggaattg cttccgaata   120
catcaatgta ttaaggtatt gattaccaac atgttttcca tatttcagtt ctcatacttg   180
gcctttgcta tgccatgatg acaggaaaaa gaaacctgtg gttgatatta ccacaagct    240 gttaaactat ctgtaattca aaccaataaa aaagaaaatc tttcgtttaa ttttggcagt   300
aaagcagctt ctaatgtctt tattaactga tcaaggtgtc tataactttt tatgcaataa   360
tgtgcctgaa attcctgtga atgaaaaatc tactttgaat aacaatgtgg catgtgtcag   420
cttgatattt tgagaggaaa tgtgttcttg aaagttgtag aggatggaca aattttgttg   480
gaagtctggc aagccttgtt aacttactgt tagaatttag gcttaggacc taattcaacc   540
ccagaaaact gaattgtaag gtgaggatta tccaagcttc ataagcttta tttaagccac   600
```

```
attccttgtc atgtgggact aaacacaccc tcaatgctgg aattaaggca gcccaaagat    660
gccacaacta aggtgctcta tgggtgacag caattaaggt ggttttccaa cacttatagc    720
ataattgact ctaaaagatt aa                                              742
```

```
<210> SEQ ID NO 10
<211> LENGTH: 301
<212> TYPE: DNA
<213> ORGANISM: Glycine max
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t

<400> SEQUENCE: 10
```

```
atttttanag atattttcaa tatattttta ttattaaaaa taactcatat ttagcagtta     60
ttacagggtt acattattca aaaggttgtt ancncattac attcaattac tataaattgt    120
agacataaac cccaaaattc tacaagcata tgttattgcc aatgaaaaat agtactcaat    180
tttaacagac aaaagttagt taaggggagg gagcattgga tataactctc gttgataagt    240
gataactgct aaataatagt gaattaatag tgaaaaatcg gtctaaaatt aacttagaat    300
t                                                                    301
```

```
<210> SEQ ID NO 11
<211> LENGTH: 395
<212> TYPE: DNA
<213> ORGANISM: Glycine max

<400> SEQUENCE: 11
```

```
actaaaacat atttccaccaa ctgcaaaaac aagaagatgc aacagaaaga tatttcaaca    60
gtttacctta aaaatagca gtaccaaaaa acaaaaagca aaggaagggt tggttccagc    120
aacaaaaaaa tctaaatttc ataacagagg tgtattgaaa atccaaaaaa ttggacctaa    180
catcttgatc tattctctaa gcctccctac gcacaaagta cagcttgccc atcacatgaa    240
ggatggcaac aaatgctatg aagccaatgc tcattacaag aacaacattt ggggagatct    300
tgagtccagg ggcatcatct gtgtaaaatt ggagcatagt tccagctgct cctccagagg    360
ccgcaccacc ggttgttctc cttctcctca tgctt                              395
```

```
<210> SEQ ID NO 12
<211> LENGTH: 301
<212> TYPE: DNA
<213> ORGANISM: Glycine max
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
```

<222> LOCATION: (120)..(120)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (127)..(128)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (272)..(272)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t

<400> SEQUENCE: 12

| | | | | | |
|---|---|---|---|---|---|
| tgtgactctn | ttgtaattgt | tataataagt | attataaatt | ntttatatt | atttttttat | 60 |
| ttttactgat | aaaanaacta | ataagatgta | caactagatt | aaactaaact | cacaacttan | 120 |
| aanaaannga | tcaaatantc | aaatcaacct | aagtggtcca | atttgcccac | tctaatgcaa | 180 |
| atagagggcg | caaagaagca | atgcggctta | ttgttttcat | ggagctatag | ctagagcttt | 240 |
| tttcnttgat | ttgatgtcat | ngagttaaac | antgcaattt | ggaaaaggtc | natatttgac | 300 |
| t | | | | | | 301 |

<210> SEQ ID NO 13
<211> LENGTH: 301
<212> TYPE: DNA
<213> ORGANISM: Glycine max
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t

<400> SEQUENCE: 13

| | | | | | |
|---|---|---|---|---|---|
| ttattttaaa | ttttaaaaca | attaatttaa | tataataaca | actaaaaatt | attactatac | 60 |
| ataatagaaa | tttttagtag | ccacattctt | tttacatttg | tcaatgtaat | ttggatttat | 120 |
| tatcctcgta | ttctctttat | tnttgcatta | ctttaccctc | cctgacctaa | tggtgttaac | 180 |
| tattgttcac | atttttatgt | agacccttat | gttcttccct | taattccaaa | cccttcagat | 240 |
| ctagcaccac | cacccacgaa | ctaatcccct | atcttccttc | ctcaccgtcg | ccaccnttac | 300 |
| c | | | | | | 301 |

<210> SEQ ID NO 14
<211> LENGTH: 26
<212> TYPE: DNA
<213> ORGANISM: Glycine max

```
<400> SEQUENCE: 14
tttatgcaat aatgtgcctg aaattc                                           26

<210> SEQ ID NO 15
<211> LENGTH: 24
<212> TYPE: DNA
<213> ORGANISM: Glycine max

<400> SEQUENCE: 15
gacacatgcc acattgttat tcaa                                             24

<210> SEQ ID NO 16
<211> LENGTH: 20
<212> TYPE: DNA
<213> ORGANISM: Glycine max

<400> SEQUENCE: 16
agtagatttt tcattcacag                                                  20

<210> SEQ ID NO 17
<211> LENGTH: 17
<212> TYPE: DNA
<213> ORGANISM: Glycine max

<400> SEQUENCE: 17
agatttgtca ttcacag                                                     17

<210> SEQ ID NO 18
<211> LENGTH: 301
<212> TYPE: DNA
<213> ORGANISM: Glycine max

<400> SEQUENCE: 18
agcatcaagg agaatgaatg tgagaaaaag gacgagcatt acatttcatc tatacaagaa      60
aatcttgtca atgccctaac atatgggtaa atgaaatttc agaaccagtg caagtttgat     120
tggcacctgt ttccttctca agggaaaatg tgatttctaa ataacctgat acgttttgat    180
cccttaatta gtaccataga accoctaaag tccacttctt cctcatattg agtgggaaag    240
gtaaaatgta aaaactaaca ttaaaacagc ccaaccacaa gacactatat tcatgtaaat    300
t                                                                    301

<210> SEQ ID NO 19
<211> LENGTH: 301
<212> TYPE: DNA
<213> ORGANISM: Glycine max
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
```

```
<220> FEATURE:
<221> NAME/KEY: misc_feature
<222> LOCATION: (294)..(294)
<223> OTHER INFORMATION: n is a, c, g, or t

<400> SEQUENCE: 19
cattggtgaa agagttctac acaaacattt acgattcgaa ggatggctcc ntggagcagt      60
gtagggtncg gggaaagctc atcaagttcg atgaacaaac nttgaatgtt ttcctagaga    120
ccctcgtcat cattccagag ggggagagcc tgaccacctt ctctcagttc atgcacacct    180
accctaatgc ccaaaccatt atggcaaagt tgtgcatgtc gggtggtcat tttgttctga    240
atgttgagtg agctctgtgn aagatcntat ggaaagacct aactacactt gcanaaacat    300
g                                                                   301

<210> SEQ ID NO 20
<211> LENGTH: 301
<212> TYPE: DNA
<213> ORGANISM: Glycine max
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t

<400> SEQUENCE: 20
cccgatcgac accaaaccac ngtgagtggt atgtgtccaa cacttncgaa tccattcgtt      60
catggcatgc ttgcatggat ctgtaacttt tcccctcctt atcgcccat ataaaagact     120 tggagatcct atccaaatca tcataagtag atctaggaat gaaagaagat tgcatggtat    180
aggaaggaaa agcaaaagga taacttttgt ccaggttatt ctcccaacaa aggagagtgt    240 gttttcttc caagcattaa atttggatca agctatatcc acaattgtag agttccaagc    300
c                                                                   301

<210> SEQ ID NO 21
<211> LENGTH: 121
<212> TYPE: DNA
<213> ORGANISM: Glycine max

<400> SEQUENCE: 21
caactccact ggcaacaagc ctgatgtcat tttgatcgga actggttcgg aattggaaat      60
tgctgccaaa gctgctgatg acctaaggaa ggaagggaag gctgttagag ttgtttccct    120
t                                                                   121

<210> SEQ ID NO 22
<211> LENGTH: 301
<212> TYPE: DNA
<213> ORGANISM: Glycine max
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t
```

<400> SEQUENCE: 22

```
ttagttttga tgtcaccggt caggaagcng tcgagtttcc tctgcatgga agagtcacat    60
ctttcatgtt gtacaacagt tccatattta cagcaaaaag gttcatagtt ccacatcaat   120
gtataccatg atcacacaag tcaacctctc tatgttccaa tttgtctgaa cgccccaaca   180
aagtgaatac cagcaattcc actactagca aggatctcat gccaagacag atggaagtat   240
gtgaagcata ggaataaggg accnaaggag tgaaatgttg ttcagtgagg tgcttgaana   300
g                                                                   301
```

<210> SEQ ID NO 23
<211> LENGTH: 301
<212> TYPE: DNA
<213> ORGANISM: Glycine max
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t

<400> SEQUENCE: 23

```
atttaaaaat atgtttaaca aaatatggat aaaaatgtat ttaaaaatat gttttttttc    60
caaaagccat gtatttaaaa ttatgtttaa acaatatgg ataacatttt tctttacccc   120
aaatacaacc ntaattgcca aaaccaaaac gactctaaat aaatttattt tcctcatcta   180
cagtgaccat gcaggttcgc tttggcagct gggtagtcca ggacttcaga attttaatct   240
aggaattgct attctcaacc ccttttggt tacaaatntt taaaattcca aaaatacttt   300
t                                                                  301
```

<210> SEQ ID NO 24
<211> LENGTH: 301
<212> TYPE: DNA
<213> ORGANISM: Glycine max
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t

<400> SEQUENCE: 24

```
aataataana atttattctt taaatttaaa ttatattttt aaattatgcc tatgaaaata    60
aataaaatat gaaataatt atatttatac tgtacatttt ttatattcta acaatgaaac   120
tcataanttt tgctggncca gccagtggct gcagctcatg gtaaacattt caagggacaa   180
gtctagaggc taggacttca agaaccagc tccctccaat tattcgttcc ataaattgaa   240
gatgcaaaac taatgttgtt tgtctactct ataaattcaa cagagaaata ttagcttaac   300
a                                                                  301
```

<210> SEQ ID NO 25
<211> LENGTH: 301
<212> TYPE: DNA
<213> ORGANISM: Glycine max
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (273)..(274)
<223> OTHER INFORMATION: n is a, c, g, or t

<400> SEQUENCE: 25

```
ttgttgtcta gtttatataa agttggacgt tcaaaaacat ataaagacta agaatataca      60
agagcatttg ctcacatgta ataatttaag cagttttaca aattttatg atttagacta     120
ctagattcct tttcatattt tgatttatca agcctaccta attagcatag ccttcaatat     180
ggtcgaaaaa acatacaacc atttatagct tagaaacttt tcggtggaaa agcaccattt     240
atctcacgag aaaaaaggg ttataatntt atnntgtaaa ttaaaataat tattttaaag     300
t                                                                    301
```

<210> SEQ ID NO 26
<211> LENGTH: 301
<212> TYPE: DNA
<213> ORGANISM: Glycine max
<220> FEATURE:
<221> NAME/KEY: misc_feature
<222> LOCATION: (223)..(223)
<223> OTHER INFORMATION: n is a, c, g, or t

<400> SEQUENCE: 26

```
ggaatcgtgg atattgtacc caaaaaaact gggatatcgt ccatagacat ctctttttt      60
ggcttaacca tgtgtgagtg gtttcaaaac tgttgaggga atatatattg gtatggtaca    120
gaccacagag aatgagaata tttgtatcat aaatttgacc aagtctacga gaaggttcat    180
ggctgacatg gatgatatgt aaagaataat aaactaatgc ggnttttaa tggatttaat    240
atttttttat aaaactatta acagtattta tatatacccca tgtactgcat atacgagaga    300
g                                                                    301
```

<210> SEQ ID NO 27
<211> LENGTH: 301
<212> TYPE: DNA
<213> ORGANISM: Glycine max
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (157)..(157)
<223> OTHER INFORMATION: n is a, c, g, or t

<400> SEQUENCE: 27

```
gtggtggaat tccattgtca ttctttggaa actggaaagc aatgatagct gataaaaatn     60
atgggagctt gtccaagtca gatcatcttc aatttnaaat cctaaaattn gntcaagttt   120
```

```
attaccagga cagagttaca gttacaagca aacagcnaca aatggagtta gtaaaaatcc    180
taactatctt cactgccatt aacttgtcat gcaataaatt tgagggacaa ataccagaag    240
ggcttggaga actaaatgct ctctacattc ttaatctatc acacaatgct ttctcaggcc    300
g                                                                    301
```

<210> SEQ ID NO 28
<211> LENGTH: 301
<212> TYPE: DNA
<213> ORGANISM: Glycine max

<400> SEQUENCE: 28

```
aatgttttttt aatcagtgga taaagagtaa aattttgatt agttattttt tttggtttgt    60
tgatatgttt taaaaaattg tattaatttg aatattttta aatatatatt aatgcatttg    120
ataaaagtaa ttgttggtat ttcatattaa taatcaaatg ttcactattg gtgcaggtgg    180
ttgtctggag ctaagtcacg agatgattat agatcccttg tttagaaaga aaaacaaata    240
aaatgatgtg atgatgagac acattatcag agaatcctgt gcgtatagta gctttatgac    300
a                                                                    301
```

<210> SEQ ID NO 29
<211> LENGTH: 301
<212> TYPE: DNA
<213> ORGANISM: Glycine max
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t

<400> SEQUENCE: 29

```
atccttacca gttagaccaa catttgtttg gctgcatgac aataagttgt taaacggttt    60
ttttgttttt ggtcatcaga atagttgaat cttgaatgtg aatatatntt caacaatcaa    120
cactaataca gtgatataag cgtcttgggt cttactaaga ccaatataga ttatggacct    180
aggatttnat tgctggatgg actttgcttt taaaatctcc tcattgctat ttacccccct    240
cccctccacc aagttgtttt tctacattaa taaaaatgcc cctctaccan ttnttttca    300 t                                                                    301
```

<210> SEQ ID NO 30
<211> LENGTH: 301
<212> TYPE: DNA
<213> ORGANISM: Glycine max
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature

```
<222> LOCATION: (121)..(121)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t

<400> SEQUENCE: 30
tcattattgt tatcgtttta ttgtatcaca attattatga tcattctatt attattgtca      60
ttgtcattat ntgttgcctt ctcaccacac catcatcact actaccacca tcgtaccctng    120 nctttactgc nttcaccacc accatcattc caccactttt atcaccatta caattgtcat    180
catngccgnc aacaatacta tattgtcgtc gttgccacca tttctccatc gcaactatcg    240
ctatcatttg tcacctncat tgtcgtgtct ctttcattgt cactatccca cccactatca    300
c                                                                    301

<210> SEQ ID NO 31
<211> LENGTH: 121
<212> TYPE: DNA
<213> ORGANISM: Glycine max

<400> SEQUENCE: 31
gaatggaata aactcaaaat cttgtccata aagatctatg tcgcaattta aaaacctctc     60
aggtataaac tcttctggat ctttccaagc cttaggatct ctatgaattg cccaagcatt    120
c                                                                    121

<210> SEQ ID NO 32
<211> LENGTH: 301
<212> TYPE: DNA
<213> ORGANISM: Glycine max
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t
<220> FEATURE:
<221> NAME/KEY: misc_feature
<222> LOCATION: (190)..(190)
<223> OTHER INFORMATION: n is a, c, g, or t

<400> SEQUENCE: 32
aacttggggt aacaaattaa tgggaagtgt gggacaaaac gtgcttgtaa gggncccaaa     60
agtaatgctc ctcccttgaa ttgtttgaac aattgaagtg catntttaat gcatgatgtt   120 tccattttc aaaattgata gggaaattcg agaaatttaa ggctaaaaca aacacatggt   180
gacggtgttn cacatgaaaa accatcatag tcccctacta ttttcttcct tctgacccat    240
atacatatgt gtattgtgta ggatcctcct gtggatgagg gaaaaccacg attcccttaa    300
a                                                                    301
```

<210> SEQ ID NO 33
<211> LENGTH: 301
<212> TYPE: DNA
<213> ORGANISM: Glycine max
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t

<400> SEQUENCE: 33

```
atagcatctt cataaaaaca ttatgtagat caatcttcag aaaactttcc atcattcaaa      60
ttcaaagatc acaagaaagt actaagacca tacaactaag cacacaatag acacaattca     120
aatttgaaat gtncaagtta tnataatgat ggggaagagt agagttgaag gaagtagctc     180
aagaagagtt gncaaagatt aggaggataa gtgttttgca gagcaagaag ttgcatgaac     240
atggataact catgcaacaa tttgaatttc aaattttacc tccaacgacc ataaacatat     300
a                                                                    301
```

<210> SEQ ID NO 34
<211> LENGTH: 301
<212> TYPE: DNA
<213> ORGANISM: Glycine max

<400> SEQUENCE: 34

```
aggaatggtg tgcattattg gaggaatgat gcttatttgc tcgtgttatt tatttttttgg     60 tttttttat cttttcagct ttttcacaat aatttgtaga cattgatcgt gacttcacgt      120
atttttttgt agcaagaagt cagatgggga tgatgagggg tctaaaaggt ggcaagacat     180
gaatgtgatg tgtcagaggt tggagtgggg atgatggatc aataatcgct tagatgcaga     240
gtgtgtgtta agagaaagca aaggcgtgag ttttatcaaa tggggtattt ttattttga     300 t                                                                    301
```

<210> SEQ ID NO 35
<211> LENGTH: 301
<212> TYPE: DNA
<213> ORGANISM: Glycine max
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t
<220> FEATURE:
<221> NAME/KEY: misc_feature
<222> LOCATION: (104)..(104)
<223> OTHER INFORMATION: n is a, c, g, or t

<400> SEQUENCE: 35

```
gggcacaata ggaatttcat tggtcttctc ttttattata tagtaaatag atataagtgt      60
tggagagatg gaatcatgga gcatgtttan gtagtgagtt nggnattgtc ccatgaaata     120
agtgaaacat actagaaggg aggttgagta atatgtatgt gtaacttata aatttctttg     180
aaatcttttt gcaaatataa cttacaaagc aagttcacaa atgactcatc caaagactaa     240
```
aacgggagga aaagataaaa gcataaggtc aagaataatc attttttatac taattcttaa    300 g                                                                    301

<210> SEQ ID NO 36
<211> LENGTH: 301
<212> TYPE: DNA
<213> ORGANISM: Glycine max
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t

<400> SEQUENCE: 36
ggtttgagtt tcgacaatat agcagagaat anccattatt tgacttgtag acaagtagga    60
attaactctt aaaatttata aatatggcca ctaataaaat gatagatttc ggaagttccg    120
ttatgtggaa ggaatgaata ctcaaaggga ctcgagtagc agaaaacgng cagttgataa    180
tggcttcgtt aactagtcca taatctggtg actcgaacaa acatgcaaca cttgaagctg    240
tttggaagtg actagatcac gcacaaaatg ttagtctatt gcaaggtgcc tcatcctaga    300
a                                                                    301

<210> SEQ ID NO 37
<211> LENGTH: 543
<212> TYPE: DNA
<213> ORGANISM: Glycine max

<400> SEQUENCE: 37
cctggagtcc attataataa ttataagtaa catgattagg tttcgggtga tgatatcaag    60
aaatataagg tttctacaga ttcaatagca attctatttg gaaagatttt aaacaaagga    120
ctggaatgct gataagaaac aatgatgaaa atataaggat aaagatacta aaacaaccta    180
tgtaaagttc aaatgtggat cattcaggga aaaaattaga atggacggga tgttatccac    240
tagcttgcaa aggagtatgt gagaagtgtg caagtatgtt ttttaagtat aacaaataag    300
ccctgtacct gtttacagaa agagtcaatc tcatcatgta gaatgccatg catcaaagtt    360
aaagatgcac tctgtgcaga acagctttgt aagtctggag gttgcaaggg gaaggtgaca    420
tctggctgta taattcaaaa cccacaatga acaccaacat atacacaaaa agtaagactt    480
gagtaaggat ctttcttacg tgttcctggt cacgtgctat ctgtgacaat gcaatcaggc    540
ggt                                                                  543

<210> SEQ ID NO 38
<211> LENGTH: 301
<212> TYPE: DNA
<213> ORGANISM: Glycine max
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (293)..(294)
<223> OTHER INFORMATION: n is a, c, g, or t

```
<400> SEQUENCE: 38
gcaatgacga gctcctgaag ctgcgttatg cgagcgttga aggaagacat caaggaatcc      60
aacgatgctc aggctttgtt cttgttcatc tttctctgcg ttcgtgaatg aagcaaatcc     120
ttttgatttc aaatgttgcc agtttcggcg gcaatgtttc cagttgcgta tttataatta     180
tttttcagtt tacatctttt atgggacttg gtttcgtaat agtaactaag caggaaaaat     240
ataccatgca ggtaaagaca tggtgagaga aagaaaataa atanaaaaaa nanntagata     300
t                                                                     301

<210> SEQ ID NO 39
<211> LENGTH: 28
<212> TYPE: DNA
<213> ORGANISM: Glycine max

<400> SEQUENCE: 39
gtgagaagtg tgcaagtatg tttttttaa                                        28

<210> SEQ ID NO 40
<211> LENGTH: 27
<212> TYPE: DNA
<213> ORGANISM: Glycine max

<400> SEQUENCE: 40
gcattctaca tgatgagatt gactctt                                          27

<210> SEQ ID NO 41
<211> LENGTH: 16
<212> TYPE: DNA
<213> ORGANISM: Glycine max

<400> SEQUENCE: 41
aggtacatgg cttatt                                                      16

<210> SEQ ID NO 42
<211> LENGTH: 15
<212> TYPE: DNA
<213> ORGANISM: Glycine max

<400> SEQUENCE: 42
aggtacaggg cttat                                                       15
```